(12) United States Patent
Afar et al.

(10) Patent No.: US 6,602,501 B1
(45) Date of Patent: Aug. 5, 2003

(54) C-TYPE LECTIN TRANSMEMBRANE ANTIGEN EXPRESSED IN HUMAN PROSTATE CANCER AND USES THEREOF

(75) Inventors: Daniel E. H. Afar, Pacific Palisades, CA (US); Rene S. Hubert, Los Angeles, CA (US); Aya Jakobovits, Beverly Hills, CA (US); Arthur B. Raitano, Los Angeles, CA (US)

(73) Assignee: Agensys, Inc., Santa Monica, CA (US)

( * ) Notice: Subject to any disclaimer, the term of this patent is extended or adjusted under 35 U.S.C. 154(b) by 0 days.

(21) Appl. No.: 09/638,203

(22) Filed: Aug. 11, 2000

Related U.S. Application Data

(60) Provisional application No. 60/148,935, filed on Aug. 12, 1999.

(51) Int. Cl.$^7$ .................. A61K 39/395; C07K 16/00; C07K 16/18; C07K 16/30
(52) U.S. Cl. .................. 424/130.1; 424/133.1; 424/135.1; 424/138.1; 424/139.1; 424/141.1; 424/142.1; 530/387.7; 530/388.1; 530/388.15; 530/388.8; 530/388.85; 530/389.1; 530/389.7
(58) Field of Search .................. 530/387.7, 388.1, 530/388.15, 388.8, 388.85, 389.1, 389.7; 424/130.1, 133.1, 135.1, 138.1, 139.1, 141.1, 142.1

(56) References Cited

U.S. PATENT DOCUMENTS 5,681,923 A * 10/1997 Platt

FOREIGN PATENT DOCUMENTS

| EP | 1074617 | 2/2001 |
| WO | WO 00/06698 | 2/2000 |
| WO | WO 00/39296 | 7/2000 |
| WO | WO 00/56889 | 9/2000 |

OTHER PUBLICATIONS

Ellerhorst et al. Proc Amer Assoc Cancer Res, 1993, vol. 34, p. 95 (abs).*
Schlom, Molecular Foundations of Oncology, 1991, pp. 95–134.*
Idikio, International Journal of Oncology, 1998, vol. 12, pp. 1287–1290. (abs).*
Kierszenbaum et al, Molecular Biology of the Cell, 1999, vol. 10, Suppl., p. 217a. (abs.*
Shilayama et al, Med Journal Kinki Univ., 1992, vol. 17, pp. 265–272. (abs).*
Kierszenbaum et al, Prostate, 2000, vol. 43, pp. 175–183. (abs).*
Mark L. Borowsky et al., "Layilin, A Novel Talin–binding . . . Ruffles," The Journal of Cell Biology, 1998, 143:429–442.
S. Gokudan et al., "Horseshoe crab acetyl . . . fibrinogen," Proc. Natl. Acad. Sci. USA, 1999, 96:10086–10091.
A.L. Kierszenbaum et al., "Galactosyl Receptor, a Cell . . . Cells," The Prostate, 43:175–183, 2000.
A. Kobayashi et al., "Cloning and in vitro transcription . . . gene," Biochimica et Biophysica Act, 1989, 1009:244–250.
M. Matsui et al, "Purification and characterization . . . gene," Eur. J. Biochem., 219:449–454, 1994.
G. Nordsiek et al., "Homo sapiens chromosome 21 PAC RPCIP704H2137," EMBL No. H5H2137, 1999, 60 pgs.
O. Spertini et al., "Regulation of Leukocyte Adhesion . . . Cells," Leukemia, 5(4):300–308, 1991.
H. Takahashi et al., "Cloning and Sequencing of cDNA . . . Wall," The Journal of Biological Chemistry, 1985, 260(22):12228–12233.
T.F. Tedder, "Cell–surface Receptor . . . Function," Am. J. Respir. Cell Mol. Biol., 1991, 5:305–306.

* cited by examiner

*Primary Examiner*—Anthony C. Caputa
*Assistant Examiner*—Karen A. Canella
(74) *Attorney, Agent, or Firm*—Morrison & Foerster LLP

(57) ABSTRACT

A novel gene (designated PC-LECTIN) that is highly overexpressed in prostate cancer and its encoded protein is described. PC-LECTIN in normal human tissues is restricted to testis, but is highly expressed in prostate cancer. Consequently, PC-LECTIN provides a diagnostic and/or therapeutic target for prostate cancer.

13 Claims, 19 Drawing Sheets

FIG. 1A

```
              10           19           28           37           46           55
5' TCC AGG ACC AGG GCG CAC CGG CTC AGC CTC TCA CTT GTC AGA GGC CGG GGA AGA
   --- --- --- --- --- --- --- --- --- --- --- --- --- --- --- --- --- ---

64           73           82           91          100          109
   GAA GCA AAG CGC AAC GGT GTG GTC CAA GCC GGG GCT TCT GCT TCG CCT CTA GGA
   --- --- --- --- --- --- --- --- --- --- --- --- --- --- --- --- --- ---

118          127          136          145          154          163
   CAT ACA CGG GAC CCC CTA ACT TCA GTC CCC CAA ACG CGC ACC CTC GAA GTC TTG
   --- --- --- --- --- --- --- --- --- --- --- --- --- --- --- --- --- ---

172          181          190          199          208          217
   AAC TCC AGC CCC GCA CAT CCA CGC GCG GCA CAG GCG CGG CAG GCG GCA GGT CCC
   --- --- --- --- --- --- --- --- --- --- --- --- --- --- --- --- --- ---

226          235          244          253          262          271
   GGC CGA AGG CGA TGC GCG CAG GGG GTC GGG CAG CTG GGC TCG GGC GGC GGG AGT
   --- --- --- --- --- --- --- --- --- --- --- --- --- --- --- --- --- ---

280          289          298          307          316          325
   AGG GCC CGG CAG GGA GGC AGG GAG GCT GCA GAG TCA GAG TCG CGG GCT GCG CCC
   --- --- --- --- --- --- --- --- --- --- --- --- --- --- --- --- --- ---

334          343          352          361          370          379
   TGG GCA GAG GCC GCC CTC GCT CCA CGC AAC ACC TGC TGC TGC CAC CGC GCC GCG
   --- --- --- --- --- --- --- --- --- --- --- --- --- --- --- --- --- ---

388          397          406          415          424          433
   ATG AGC CGC GTG GTC TCG CTG CTG CTG GGC GCC GCG CTG CTC TGC GGC CAC GGA
    M   S   R   V   V   S   L   L   L   G   A   A   L   L   C   G   H   G 442          451          460          469          478          487
   GCC TTC TGC CGC CGC GTG GTC AGC GGC CAA AAG GTG TGT TTT GCT GAC TTC AAG
    A   F   C   R   R   V   V   S   G   Q   K   V   C   F   A   D   F   K 496          505          514          523          532          541
   CAT CCC TGC TAC AAA ATG GCC TAC TTC CAT GAA CTG TCC AGC CGA GTG AGC TTT
    H   P   C   Y   K   M   A   Y   F   H   E   L   S   S   R   V   S   F 550          559          568          577          586          595
   CAG GAG GCA CGC CTG GCT TGT GAG AGT GAG GGA GGA GTC CTC CTC AGC CTT GAG
    Q   E   A   R   L   A   C   E   S   E   G   G   V   L   L   S   L   E 604          613          622          631          640          649
   AAT GAA GCA GAA CAG AAG TTA ATA GAG AGC ATG TTG CAA AAC CTG ACA AAA CCC
    N   E   A   E   Q   K   L   I   E   S   M   L   Q   N   L   T   K   P
```

FIG. 1B

```
        658             667             676             685             694             703
GGG ACA GGG ATT TCT GAT GGT GAT TTC TGG ATA GGG CTT TGG AGG AAT GGA GAT
---  ---  ---  ---  ---  ---  ---  ---  ---  ---  ---  ---  ---  ---  ---  ---
 G   T   G   I   S   D   G   D   F   W   I   G   L   W   R   N   G   D 712             721             730             739             748             757
GGG CAA ACA TCT GGT GCC TGC CCA GAT CTC TAC CAG TGG TCT GAT GGA AGC AAT
---  ---  ---  ---  ---  ---  ---  ---  ---  ---  ---  ---  ---  ---  ---  ---
 G   Q   T   S   G   A   C   P   D   L   Y   Q   W   S   D   G   S   N 766             775             784             793             802             811
TCC CAG TAC CGA AAC TGG TAC ACA GAT GAA CCT TCC TGC GGA AGT GAA AAG TGT
---  ---  ---  ---  ---  ---  ---  ---  ---  ---  ---  ---  ---  ---  ---  ---
 S   Q   Y   R   N   W   Y   T   D   E   P   S   C   G   S   E   K   C 820             829             838             847             856             865
GTT GTG ATG TAT CAC CAA CCA ACT GCC AAT CCT GGC CTT GGG GGT CCC TAC CTT
---  ---  ---  ---  ---  ---  ---  ---  ---  ---  ---  ---  ---  ---  ---  ---
 V   V   M   Y   H   Q   P   T   A   N   P   G   L   G   G   P   Y   L 874             883             892             901             910             919
TAC CAG TGG AAT GAT GAC AGG TGT AAC ATG AAG CAC AAT TAT ATT TGC AAG TAT
---  ---  ---  ---  ---  ---  ---  ---  ---  ---  ---  ---  ---  ---  ---  ---
 Y   Q   W   N   D   D   R   C   N   M   K   H   N   Y   I   C   K   Y 928             937             946             955             964             973
GAA CCA GAG ATT AAT CCA ACA GCC CCT GTA GAA AAG CCT TAT CTT ACA AAT CAA
---  ---  ---  ---  ---  ---  ---  ---  ---  ---  ---  ---  ---  ---  ---  ---
 E   P   E   I   N   P   T   A   P   V   E   K   P   Y   L   T   N   Q 982             991            1000            1009            1018            1027
CCA GGA GAC ACC CAT CAG AAT GTG GTT GTT ACT GAA GCA GGT ATA ATT CCC AAT
---  ---  ---  ---  ---  ---  ---  ---  ---  ---  ---  ---  ---  ---  ---  ---
 P   G   D   T   H   Q   N   V   V   V   T   E   A   G   I   I   P   N 1036            1045            1054            1063            1072            1081
CTA ATT TAT GTT GTT ATA CCA ACA ATA CCC CTG CTC TTA CTG ATA CTG GTT GCT
---  ---  ---  ---  ---  ---  ---  ---  ---  ---  ---  ---  ---  ---  ---  ---
 L   I   Y   V   V   I   P   T   I   P   L   L   L   L   I   L   V   A 1090            1099            1108            1117            1126            1135
TTT GGA ACC TGT TGT TTC CAG ATG CTG CAT AAA AGT AAA GGA AGA ACA AAA ACT
---  ---  ---  ---  ---  ---  ---  ---  ---  ---  ---  ---  ---  ---  ---  ---
 F   G   T   C   C   F   Q   M   L   H   K   S   K   G   R   T   K   T 1144            1153            1162            1171            1180            1189
AGT CCA AAC CAG TCT ACA CTG TGG ATT TCA AAG AGT ACC AGA AAA GAA AGT GGC
---  ---  ---  ---  ---  ---  ---  ---  ---  ---  ---  ---  ---  ---  ---  ---
 S   P   N   Q   S   T   L   W   I   S   K   S   T   R   K   E   S   G 1198            1207            1216            1225            1234            1243
ATG GAA GTA TAA TAA CTC ATT GAC TTG GTT CCA GAA TTT TGT AAT TCT GGA TCT
---  ---  ---  ---  ---  ---  ---  ---  ---  ---  ---  ---  ---  ---  ---  ---
 M   E   V   *   *
```

FIG. 1C

```
          1252        1261        1270        1279        1288        1297
    GTA TAA GGA ATG GCA TCA GAA CAA TAG CTT GGA ATG GCT TGA AAT CAC AAA GGA
    --- --- --- --- --- --- --- --- --- --- --- --- --- --- --- --- --- ---
              1306        1315        1324        1333        1342        1351
        TCT GCA AGA TGA ACT GTA AGC TCC CCC TTG AGG CAA ATA TTA AAG TAA TTT TTA
        --- --- --- --- --- --- --- --- --- --- --- --- --- --- --- --- --- ---
              1360        1369        1378        1387        1396        1405
    TAT GTC TAT TAT TTC ATT TAA AGA ATA TGC TGT GCT AAT AAT GGA GTG AGA CAT
    --- --- --- --- --- --- --- --- --- --- --- --- --- --- --- --- --- ---
              1414        1423        1432        1441        1450        1459
    GCT TAT TTT GCT AAA GGA TGC ACC CAA ACT TCA AAC TTC AAG CAA ATG AAA TGG
    --- --- --- --- --- --- --- --- --- --- --- --- --- --- --- --- --- ---
              1468        1477        1486        1495        1504        1513
    ACA ATG CAG ATA AAG TTG TTA TCA ACA CGT CGG GAG TAT GTG TGT TAG AAG CAA
    --- --- --- --- --- --- --- --- --- --- --- --- --- --- --- --- --- ---
              1522        1531        1540        1549        1558        1567
    TTC CTT TTA TTT CTT TCA CCT TTC ATA AGT TGT TAT CTA GTC AAT GTA ATG TAT
    --- --- --- --- --- --- --- --- --- --- --- --- --- --- --- --- --- ---
              1576        1585        1594        1603        1612        1621
    ATT GTA TTG AAA TTT ACA GTG TGC AAA AGT ATT TTA CCT TTG CAT AAG TGT TTG
    --- --- --- --- --- --- --- --- --- --- --- --- --- --- --- --- --- ---
              1630        1639        1648        1657        1666        1675
    ATA AAA ATG AAC TGT TCT AAT ATT TAT TTT TAT GGC ATC TCA TTT TTC AAT ACA
    --- --- --- --- --- --- --- --- --- --- --- --- --- --- --- --- --- ---
              1684        1693        1702        1711        1720        1729
    TGC TCT TTT GAT TAA AGA AAC TTA TTA CTG TTG TCA ACT GAA TTC ACA CAC ACA
    --- --- --- --- --- --- --- --- --- --- --- --- --- --- --- --- --- ---
              1738        1747        1756        1765        1774        1783
    CAA ATA TAG TAC CAT AGA AAA AGT TTG TTT TCT CGA AAT AAT TCA TCT TTC AGC
    --- --- --- --- --- --- --- --- --- --- --- --- --- --- --- --- --- ---
              1792        1801        1810        1819        1828        1837
    TTC TCT GCT TTT GGT CAA TGT CTA GGA AAT CTC TTC AGA AAT AAG AAG CTA TTT
    --- --- --- --- --- --- --- --- --- --- --- --- --- --- --- --- --- ---
              1846        1855        1864        1873        1882        1891
    CAT TAA GTG TGA TAT AAA CCT CCT CAA ACA TTT TAC TTA GAG GCA AGG ATT GTC
    --- --- --- --- --- --- --- --- --- --- --- --- --- --- --- --- --- ---
              1900        1909        1918        1927        1936        1945
    TAA TTT CAA TTG TGC AAG ACA TGT GCC TTA TAA TTA TTT TTA GCT TAA AAT TAA
    --- --- --- --- --- --- --- --- --- --- --- --- --- --- --- --- --- ---
              1954        1963        1972        1981        1990        1999
    ACA GAT TTT GTA ATA ATG TAA CTT TGT TAA TAG GTG CAT AAA CAC TAA TGC AGT
    --- --- --- --- --- --- --- --- --- --- --- --- --- --- --- --- --- ---
              2008        2017        2026        2035        2044        2053
    CAA TTT GAA CAA AAG AAG TGA CAT ACA CAA TAT AAA TCA TAT GTC TTC ACA CGT
    --- --- --- --- --- --- --- --- --- --- --- --- --- --- --- --- --- ---
              2062        2071        2080        2089        2098        2107
    TGC CTA TAT AAT GAG AAG CAG CTC TCT GAG GGT TCT GAA ATC AAT GTG GTC CCT
    --- --- --- --- --- --- --- --- --- --- --- --- --- --- --- --- --- ---
              2116        2125        2134        2143        2152        2161
    CTC TTG CCC ACT AAA CAA AGA TGG TTG TTC GGG GTT TGG GAT TGA CAC TGG AGG
    --- --- --- --- --- --- --- --- --- --- --- --- --- --- --- --- --- ---
              2170        2179        2188        2197        2206        2215
    CAG ATA GTT GCA AAG TTA GTC TAA GGT TTC CCT AGC TGT ATT TAG CCT CTG ACT
    --- --- --- --- --- --- --- --- --- --- --- --- --- --- --- --- --- ---
              2224        2233        2242        2251        2260        2269
    ATA TTA GTA TAC AAA GAG GTC ATG TGG TTG AGA CCA GGT GAA TAG TCA CTA TCA
    --- --- --- --- --- --- --- --- --- --- --- --- --- --- --- --- --- ---
              2278        2287        2296        2305        2314        2323
    GTG TGG AGA CAA GCA CAG CAC ACA GAC ATT TTA GGA AGG AAA GGA ACT ACG AAA
    --- --- --- --- --- --- --- --- --- --- --- --- --- --- --- --- --- ---
```

FIG. 1D

```
         2332            2341            2350            2359            2368            2377
TCG TGT GAA AAT GGG TTG GAA CCC ATC AGT GAT CGC ATA TTC ATT GAT GAG GGT
--- --- --- --- --- --- --- --- --- --- --- --- --- --- --- --- --- ---
         2386            2395            2404            2413            2422            2431
TTG CTT GAG ATA GAA AAT GGT GGC TCC TTT CTG TCT TAT CTC CTA GTT TCT TCA
--- --- --- --- --- --- --- --- --- --- --- --- --- --- --- --- --- ---
         2440            2449            2458            2467            2476            2485
ATG CTT ACG CCT TGT TCT TCT CAA GAG AAA GTT GTA ACT CTC TGG TCT TCA TAT
--- --- --- --- --- --- --- --- --- --- --- --- --- --- --- --- --- ---
         2494            2503            2512            2521            2530            2539
GTC CCT GTG CTC CTT TTA ACC AAA TAA AGA GTT CTT GTT TCT GAA GAA AAA AAA
--- --- --- --- --- --- --- --- --- --- --- --- --- --- --- --- --- ---
         2548
AAA AAA AAA AA 3'
--- --- --- --
```

FIG. 2A

```
58P1D12    23 RVVSGQKVCFADFKHPCYKMAYFHELSSRVSFQEARLACESEGGVLLSLENEAEQKLIES
Layilin    25 RLLSGQLVCRGGTRRPCYKVIYFHDAFQRLNFEEAKEACRRDGGQLVSIETEDEQRLIEK
              *  *** **       **** ***   *  * **  **   ** * * *  ** ***

58P1D12    83 MLQNLTKPGTGISDGDFWIGLWRNGDGQTSG-ACPDLYQWSDGSNSQYRNWYTDEPSCGS
Layilin    85 FIENLLA-----SDGDFWIGLRRLEVKQVNNTACQDLYAWTDGSTSQFRNWYVDEPSCGS
              **       ********* *   *    ** *** * *** **  *** ******

58P1D12   142 EKCVVMYHQPTANPGLGGPYLYQWNDDRCNMKHNYICKYE-------PEINPTAPVEKPY
Layilin   140 EVCVVMYHQPSAPPGIGGSYMFQWNDDRCNMKNNFICKYADEKPSTTPSIRPGGEATEPP
              * ********  * ** **  * ********** * ****         *  *     *

58P1D12   195 LTNQPGDTHQN----VVVTEAGIIPNLIYVVIPTIPLLLLILVAFGTCCFQMLHKSKGRT
Layilin   200 TPVLPEETQKEDTKETFKESREAALNLAYILIPSIPLFLLLVVTSAACWVWICRRRKQEQ
                 *   *          *  *   ** *  ** *** ***  *      *      *

58P1D12   251 K--TSPNQSTLWISKSTRKESGMEV
Layilin   260 PDPTTKEQHTIWPTPHQENSPNLDV
                  *   * **        *
```

FIG. 2B

[60.9% identity in 591 nt overlap; score: 613]

```
           380       390       400       410       420       430
     GCCGCGATGAGCCGCGTGGTCTCGCTGCTGCTGGGCGCCGCGCTGCTCTGCGG-CCACGG
     :: ::    :: : :::::  : :  ::  ::  ::     ::  : :::::: : :  ::::::
     GCAGCCGGGACCAGCGTTG-CAGGCCG-TGTTGCTGGCGGTGCTGCTGTCAGAACCACGG
         150       160       170       180       190       200

440       450       460       470       480       490
     AGCCTTCTGCCGCCGCGTGGTCAGCGGCCAAAAGGTGTGTTTTGCTGACTTCAAGCATCC
     :: :     : ::   :: :  :::::  ::   ::: ::    :  :       :   ::
     AGT-TCGAAGGGTCGGCTGCTGAGCGGGCAGCTGGTCTGCCGGGGAGGGACTCGGAGGCC
        210       220       230       240       250

500       510       520       530       540       550
     CTGCTACAAAATGGCCTACTTCCATGAACTGTCCAGCCGAGTGAGCTTTCAGGAGGCACG
     ::::: ::: :    ::::::::::::   :      ::  ::: :::: :::: ::
     TTGCTATAAAGTCATTTACTTCCATGATGCTTTTCAAAGACTGAACTTTGAGGAAGCCAA
  260       270       280       290       300       310

560       570       580       590       600       610
     CCTGGCTTGTGAGAGTGAGGGAGGAGTCCTCCTCAGCCTTGAGAATGAAGCAGAACAGAA
     ::  ::    ::: :: ::  :::      ::: ::::    :::: :    ::  ::::
     AGAAGCCTGCAGGAGGGATGGGGGACAGCTCGTCAGTATTGAAACAGAAGATGAGCAGAG
  320       330       340       350       360       370

620       630       640       650       660       670
     GTTAATAGAGAGCATGTTGCAAAACCTGACAAAACCCGGGACAGGGATTTCTGATGGTGA
      : ::::: :    :    :   :::::::::        :  ::  :    :::::::::::
     ACTGATAGAAAAATTCATTGAAAACCT-------CTTGGCA--------TCTGATGGTGA
  380       390       400              410              420

680       690       700       710       720
     TTTCTGGATAGGGCTTTGGAGGAATGGAGATG-----GGCAAACATCTGGTGCCTGCCCA
     :::::::::: :: ::   ::::: ::::: ::    ::  ::::  :     ::::::::
     TTTCTGGATTGGCCTCAGGAGGC-TGGAGGTGAAGCAGGTCAACAACACA-GCCTGCCAG
        430       440       450       460       470       480

730       740       750       760       770       780
     GATCTCTACCAGTGGTCTGATGGAAGCAATTCCCAGTACCGAAACTGGTACACAGATGAA
     :: :: ::       ::: : :::::  ::::  ::  ::  :  : :::::::::    ::::: 
     GACCTTTATGCTTGGACAGATGGGAGCACATCACAATTTAGGAACTGGTATGTGGATGAG
        490       500       510       520       530       540

790       800       810       820       830       840
     CCTTCCTGCGGAAGTGAAAAGTGTGTTGTGATGTATCACCAACCAACTGCCAATCCTGGC
     ::::: :: ::  :::::      :: ::  :::::::::  :: ::  ::: : ::    ::::::
     CCTTCTTGTGGCAGTGAGGTCTGCGTGGTGATGTACCATCAGCCATCGGCACCACCTGGC
        550       560       570       580       590       600
```

FIG. 2C

```
        850       860       870       880       890       900
     CTTGGGGGTCCCTACCTTTACCAGTGGAATGATGACAGGTGTAACATGAAGCACAATTAT
      : :::::   :  :::  :  :  ::::::::::::::  :::   ::::  :::::::::   ::::::
     ATCGGGGGCTCATACATGTTCCAGTGGAATGACGACCGGTGCAACATGAAGAACAATTTC
        610       620       630       640       650       660

910       920       930       940       950
     ATTTGCAAGTATGAACCAGAGATTAATCCAACAGCCCCTGTAGAAAAGCCT
     ::::::::: ::::    ::::       ::: : :::       :: ::::
     ATTTGCAAATATGCTGACGAGAAGCCAAGTACAACACCTTCTATAAGGCCT
        670       680       690       700       710
```

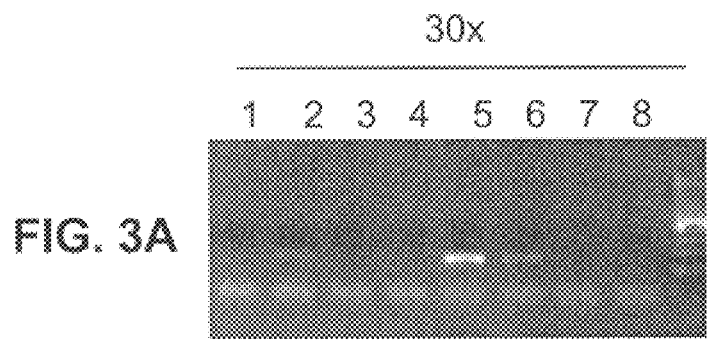
FIG. 3A
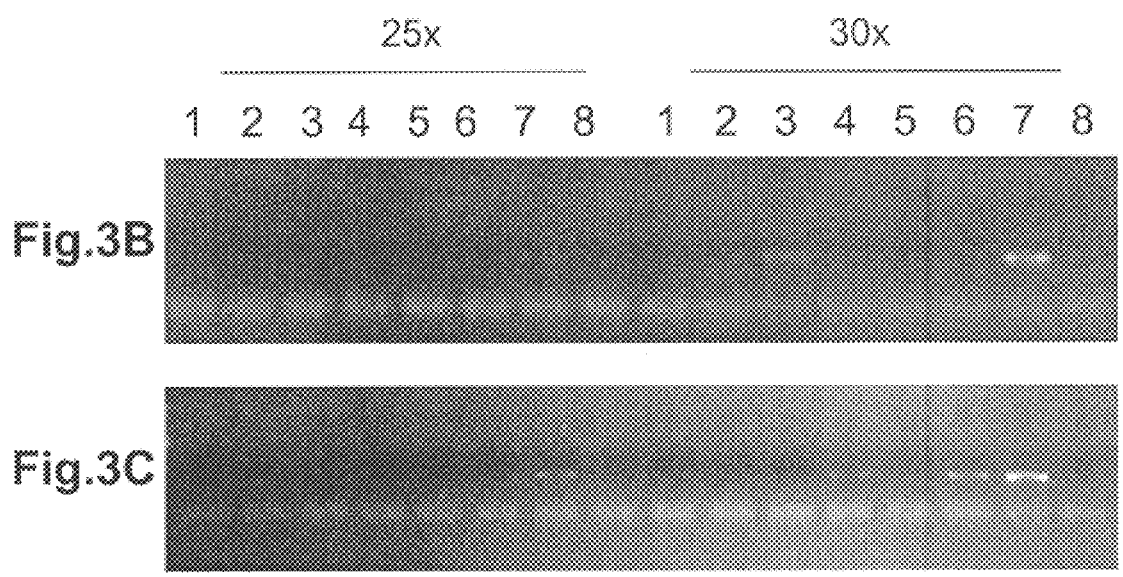
Fig. 3B
Fig. 3C

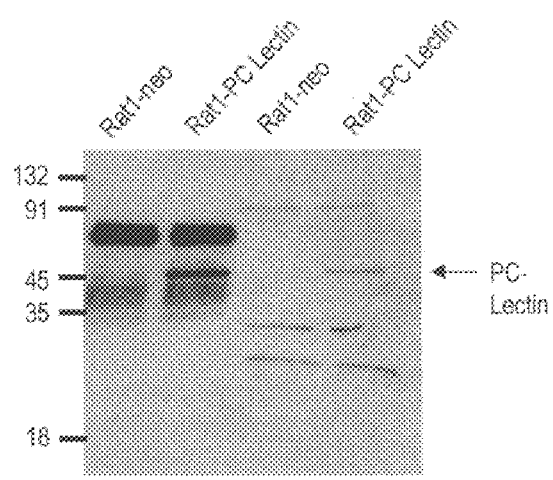 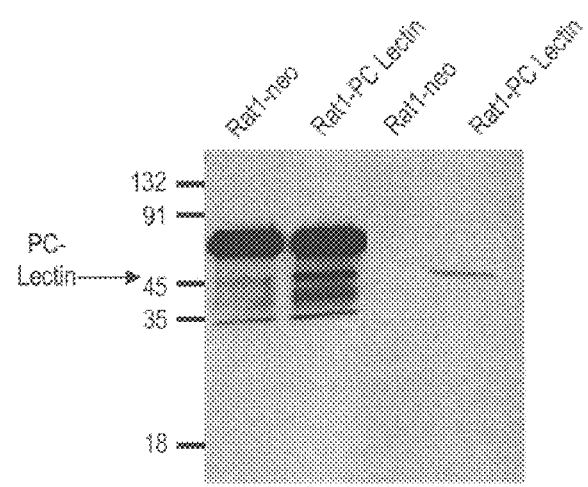
FIG. 10A
FIG. 10B

SEQUENCE LISTING

```
<160> NUMBER OF SEQ ID NOS:  47

<210> SEQ ID NO 1
<211> LENGTH: 2549
<212> TYPE: DNA
<213> ORGANISM: Homo Sapiens
<220> FEATURE:
<221> NAME/KEY: CDS
<222> LOCATION: (379)...(1200)

<400> SEQUENCE: 1
tccaggacca gggcgcaccg gctcagcctc tcacttgtca gaggccgggg aagagaagca      60
```

```
aagcgcaacg gtgtggtcca agccggggct tctgcttcgc ctctaggaca tacacgggac        120 ccccctaactt cagtccccca aacgcgcacc ctcgaagtct tgaactccag ccccgcacat        180
ccacgcgcgg cacaggcgcg gcaggcggca ggtcccggcc gaaggcgatg cgcgcagggg        240
gtcgggcagc tgggctcggg cggcgggagt agggcccggc agggaggcag ggaggctgca        300
gagtcagagt cgcgggctgc gccctgggca gaggccgccc tcgctccacg caacacctgc        360
tgctgccacc gcgccgcg atg agc cgc gtg gtc tcg ctg ctg ctg ggc gcc          411
                    Met Ser Arg Val Val Ser Leu Leu Leu Gly Ala
                     1               5                  10 gcg ctg ctc tgc ggc cac gga gcc ttc tgc cgc cgt gtc gtc agc ggc          459
Ala Leu Leu Cys Gly His Gly Ala Phe Cys Arg Arg Val Val Ser Gly
         15                  20                  25 caa aag gtg tgt ttt gct gac ttc aag cat ccc tgc tac aaa atg gcc          507
Gln Lys Val Cys Phe Ala Asp Phe Lys His Pro Cys Tyr Lys Met Ala
     30                  35                  40 tac ttc cat gaa ctg tcc agc cga gtg agc ttt cag gag gca cgc ctg          555
Tyr Phe His Glu Leu Ser Ser Arg Val Ser Phe Gln Glu Ala Arg Leu
 45                  50                  55 gct tgt gag agt gag gga gga gtc ctc ctc agc ctt gag aat gaa gca          603
Ala Cys Glu Ser Glu Gly Gly Val Leu Leu Ser Leu Glu Asn Glu Ala
 60                  65                  70                  75 gaa cag aag tta ata gag agc atg ttg caa aac ctg aca aaa ccc ggg          651
Glu Gln Lys Leu Ile Glu Ser Met Leu Gln Asn Leu Thr Lys Pro Gly
                 80                  85                  90 aca ggg att tct gat ggt gat ttc tgg ata ggg ctt tgg agg aat gga          699
Thr Gly Ile Ser Asp Gly Asp Phe Trp Ile Gly Leu Trp Arg Asn Gly
             95                  100                 105 gat ggg caa aca tct ggt gcc tgc cca gat ctc tac cag tgg tct gat          747
Asp Gly Gln Thr Ser Gly Ala Cys Pro Asp Leu Tyr Gln Trp Ser Asp
         110                 115                 120 gga agc aat tcc cag tac cga aac tgg tac aca gat gaa cct tcc tgc          795
Gly Ser Asn Ser Gln Tyr Arg Asn Trp Tyr Thr Asp Glu Pro Ser Cys
     125                 130                 135 gga agt gaa aag tgt gtt gtg atg tat cac caa cca act gcc aat cct          843
Gly Ser Glu Lys Cys Val Val Met Tyr His Gln Pro Thr Ala Asn Pro
140                 145                 150                 155 ggc ctt ggg ggt ccc tac ctt tac cag tgg aat gat gac agg tgt aac          891
Gly Leu Gly Gly Pro Tyr Leu Tyr Gln Trp Asn Asp Asp Arg Cys Asn
                 160                 165                 170 atg aag cac aat tat att tgc aag tat gaa cca gag att aat cca aca          939
Met Lys His Asn Tyr Ile Cys Lys Tyr Glu Pro Glu Ile Asn Pro Thr
             175                 180                 185 gcc cct gta gaa aag cct tat ctt aca aat caa cca gga gac acc cat          987
Ala Pro Val Glu Lys Pro Tyr Leu Thr Asn Gln Pro Gly Asp Thr His
         190                 195                 200 cag aat gtg gtt gtt act gaa gca ggt ata att ccc aat cta att tat          1035
Gln Asn Val Val Val Thr Glu Ala Gly Ile Ile Pro Asn Leu Ile Tyr
     205                 210                 215 gtt gtt ata cca aca ata ccc ctg ctc tta ctg ata ctg gtt gct ttt          1083
Val Val Ile Pro Thr Ile Pro Leu Leu Leu Leu Ile Leu Val Ala Phe
220                 225                 230                 235 gga acc tgt tgt ttc cag atg ctg cat aaa agt aaa gga aga aca aaa          1131
Gly Thr Cys Cys Phe Gln Met Leu His Lys Ser Lys Gly Arg Thr Lys
                 240                 245                 250 act agt cca aac cag tct aca ctg tgg att tca aag agt acc aga aaa          1179
Thr Ser Pro Asn Gln Ser Thr Leu Trp Ile Ser Lys Ser Thr Arg Lys
             255                 260                 265
```

```
gaa agt ggc atg gaa gta taa taactcattg acttggttcc agaattttgt      1230
Glu Ser Gly Met Glu Val  *
        270 aattctggat ctgtataagg aatggcatca gaacaatagc ttggaatggc ttgaaatcac   1290 aaaggatctg caagatgaac tgtaagctcc cccttgaggc aaatattaaa gtaatttta   1350 tatgtctatt atttcattta agaaatatgc tgtgctaata atggagtgag acatgcttat   1410 tttgctaaag gatgcaccca aacttcaaac ttcaagcaaa tgaaatggac aatgcagata   1470 aagttgttat caacacgtcg ggagtatgtg tgttagaagc aattcctttt atttctttca   1530 cctttcataa gttgttatct agtcaatgta atgtatattg tattgaaatt tacagtgtgc   1590 aaaagtattt tacctttgca taagtgtttg ataaaaatga actgttctaa tatttatttt   1650 tatggcatct cattttcaa tacatgctct tttgattaaa gaaacttatt actgttgtca    1710 actgaattca cacacacaca aatatagtac catagaaaaa gtttgttttc tcgaaataat   1770 tcatctttca gcttctctgc ttttggtcaa tgtctaggaa atctcttcag aaataagaag   1830 ctatttcatt aagtgtgata taaacctcct caaacatttt acttagaggc aaggattgtc   1890 taatttcaat tgtgcaagac atgtgcctta taattatttt tagcttaaaa ttaaacagat   1950 tttgtaataa tgtaactttg ttaataggtg cataaacact aatgcagtca atttgaacaa   2010 aagaagtgac atacacaata taaatcatat gtcttcacac gttgcctata taatgagaag   2070 cagctctctg agggttctga aatcaatgtg gtccctctct tgcccactaa acaaagatgg   2130 ttgttcgggg tttgggattg acactggagg cagatagttg caaagttagt ctaaggtttc   2190 cctagctgta tttagcctct gactatatta gtatacaaag aggtcatgtg gttgagacca   2250 ggtgaatagt cactatcagt gtggagacaa gcacagcaca cagacatttt aggaaggaaa   2310 ggaactacga aatcgtgtga aaatggggttg gaacccatca gtgatcgcat attcattgat   2370 gagggtttgc ttgagataga aaatggtggc tcctttctgt cttatctcct agtttcttca   2430 atgcttacgc cttgttcttc tcaagagaaa gttgtaactc tctggtcttc atatgtccct   2490 gtgctccttt taaccaaata aagagttctt gtttctgaag aaaaaaaaaa aaaaaaaaa    2549
```

<210> SEQ ID NO 2
<211> LENGTH: 273
<212> TYPE: PRT
<213> ORGANISM: Homo Sapiens

<400> SEQUENCE: 2

```
Met Ser Arg Val Val Ser Leu Leu Leu Gly Ala Ala Leu Leu Cys Gly
 1               5                  10                  15

His Gly Ala Phe Cys Arg Arg Val Ser Gly Gln Lys Val Cys Phe
            20                  25                  30

Ala Asp Phe Lys His Pro Cys Tyr Lys Met Ala Tyr Phe His Glu Leu
        35                  40                  45

Ser Ser Arg Val Ser Phe Gln Glu Ala Arg Leu Ala Cys Glu Ser Glu
    50                  55                  60

Gly Gly Val Leu Leu Ser Leu Glu Asn Glu Ala Glu Gln Lys Leu Ile
65                  70                  75                  80

Glu Ser Met Leu Gln Asn Leu Thr Lys Pro Gly Thr Gly Ile Ser Asp
                85                  90                  95

Gly Asp Phe Trp Ile Gly Leu Trp Arg Asn Gly Asp Gly Gln Thr Ser
                100                 105                 110

Gly Ala Cys Pro Asp Leu Tyr Gln Trp Ser Asp Gly Ser Asn Ser Gln
            115                 120                 125
```

-continued

```
Tyr Arg Asn Trp Tyr Thr Asp Glu Pro Ser Cys Gly Ser Glu Lys Cys
    130                 135                 140
Val Val Met Tyr His Gln Pro Thr Ala Asn Pro Gly Leu Gly Gly Pro
145                 150                 155                 160
Tyr Leu Tyr Gln Trp Asn Asp Asp Arg Cys Asn Met Lys His Asn Tyr
                165                 170                 175
Ile Cys Lys Tyr Glu Pro Glu Ile Asn Pro Thr Ala Pro Val Glu Lys
            180                 185                 190
Pro Tyr Leu Thr Asn Gln Pro Gly Asp Thr His Gln Asn Val Val Val
        195                 200                 205
Thr Glu Ala Gly Ile Ile Pro Asn Leu Ile Tyr Val Val Ile Pro Thr
    210                 215                 220
Ile Pro Leu Leu Leu Leu Ile Leu Val Ala Phe Gly Thr Cys Cys Phe
225                 230                 235                 240
Gln Met Leu His Lys Ser Lys Gly Arg Thr Lys Thr Ser Pro Asn Gln
                245                 250                 255
Ser Thr Leu Trp Ile Ser Lys Ser Thr Arg Lys Glu Ser Gly Met Glu
            260                 265                 270
Val
```

<210> SEQ ID NO 3
<211> LENGTH: 260
<212> TYPE: PRT
<213> ORGANISM: Hamster

<400> SEQUENCE: 3

```
Arg Leu Leu Ser Gly Gln Leu Val Cys Arg Gly Gly Thr Arg Arg Pro
1               5                   10                  15
Cys Tyr Lys Val Ile Tyr Phe His Asp Ala Phe Gln Arg Leu Asn Phe
            20                  25                  30
Glu Glu Ala Lys Glu Ala Cys Arg Arg Asp Gly Gly Gln Leu Val Ser
        35                  40                  45
Ile Glu Thr Glu Asp Glu Gln Arg Leu Ile Glu Lys Phe Ile Glu Asn
    50                  55                  60
Leu Leu Ala Ser Asp Gly Asp Phe Trp Ile Gly Leu Arg Arg Leu Glu
65                  70                  75                  80
Val Lys Gln Val Asn Asn Thr Ala Cys Gln Asp Leu Tyr Ala Trp Thr
                85                  90                  95
Asp Gly Ser Thr Ser Gln Phe Arg Asn Trp Tyr Val Asp Glu Pro Ser
            100                 105                 110
Cys Gly Ser Glu Val Cys Val Val Met Tyr His Gln Pro Ser Ala Pro
        115                 120                 125
Pro Gly Ile Gly Gly Ser Tyr Met Phe Gln Trp Asn Asp Asp Arg Cys
    130                 135                 140
Asn Met Lys Asn Asn Phe Ile Cys Lys Tyr Ala Asp Glu Lys Pro Ser
145                 150                 155                 160
Thr Thr Pro Ser Ile Arg Pro Gly Gly Glu Ala Thr Glu Pro Pro Thr
                165                 170                 175
Pro Val Leu Pro Glu Glu Thr Gln Lys Glu Asp Thr Lys Glu Thr Phe
            180                 185                 190
Lys Glu Ser Arg Glu Ala Ala Leu Asn Leu Ala Tyr Ile Leu Ile Pro
        195                 200                 205
Ser Ile Pro Leu Phe Leu Leu Leu Val Val Thr Ser Ala Ala Cys Trp
    210                 215                 220
```

Val Trp Ile Cys Arg Arg Arg Lys Gln Glu Gln Pro Asp Pro Thr Thr
225                 230                 235                 240

Lys Glu Gln His Thr Ile Trp Pro Thr Pro His Gln Glu Asn Ser Pro
                245                 250                 255

Asn Leu Asp Val
            260

<210> SEQ ID NO 4
<211> LENGTH: 585
<212> TYPE: DNA
<213> ORGANISM: Homo Sapiens

<400> SEQUENCE: 4

```
gccgcgatga gccgcgtggt ctcgctgctg ctgggcgccg cgctgctctg cggccacgga     60
gccttctgcc gccgcgtggt cagcggccaa aaggtgtgtt ttgctgactt caagcatccc    120
tgctacaaaa tggcctactt ccatgaactg tccagccgag tgagctttca ggaggcacgc    180
ctggcttgtg agagtgaggg aggagtcctc ctcagccttg agaatgaagc agaacagaag    240
ttaatagaga gcatgttgca aaacctgaca aaacccggga cagggatttc tgatggtgat    300
ttctggatag ggcttttggag gaatggagat gggcaaacat ctggtgcctg cccagatctc    360
taccagtggt ctgatggaag caattcccag taccgaaact ggtacacaga tgaaccttcc    420
tgcggaagtg aaaagtgtgt tgtgatgtat caccaaccaa ctgccaatcc tggccttggg    480
ggtccctacc tttaccagtg gaatgatgac aggtgtaaca tgaagcacaa ttatatttgc    540
aagtatgaac cagagattaa tccaacagcc cctgtagaaa agcct              585
```

<210> SEQ ID NO 5
<211> LENGTH: 571
<212> TYPE: DNA
<213> ORGANISM: Hamster

<400> SEQUENCE: 5

```
gcagccggga ccagcgttgc aggccgtgtt gctggcggtg ctgctgtcag aaccacggag     60
ttcgaagggt cggctgctga gcgggcagct ggtctgccgg ggagggactc ggaggccttg    120
ctataaagtc atttacttcc atgatgcttt tcaaagactg aactttgagg aagccaaaga    180
agcctgcagg agggatgggg gacagctcgt cagtattgaa acagaagatg agcagagact    240
gatagaaaaa tcattgaaa acctcttggc atctgatggt gatttctgga ttggcctcag    300
gaggctggag gtgaagcagg tcaacaacac agcctgccag gacctttatg cttggacaga    360
tgggagcaca tcacaattta ggaactggta tgtggatgag ccttcttgtg gcagtgaggt    420
ctgcgtggtg atgtaccatc agccatcggc accacctggc atcggggct catacatgtt    480
ccagtggaat gacgaccggt gcaacatgaa gaacaatttc atttgcaaat atgctgacga    540
gaagccaagt acaacaccctt ctataaggcc t                          571
```

<210> SEQ ID NO 6
<211> LENGTH: 9
<212> TYPE: PRT
<213> ORGANISM: Homo Sapiens

<400> SEQUENCE: 6

Trp Ile Gly Phe Thr Tyr Lys Thr Ala
 1               5

<210> SEQ ID NO 7

-continued

```
<211> LENGTH: 9
<212> TYPE: PRT
<213> ORGANISM: Homo Sapiens

<400> SEQUENCE: 7

Ala Thr Gly Glu His Gln Ala Phe Thr
 1               5

<210> SEQ ID NO 8
<211> LENGTH: 9
<212> TYPE: PRT
<213> ORGANISM: Homo Sapiens

<400> SEQUENCE: 8

Phe Gly Asn Cys Val Glu Leu Gln Ala
 1               5

<210> SEQ ID NO 9
<211> LENGTH: 9
<212> TYPE: PRT
<213> ORGANISM: Homo Sapiens

<400> SEQUENCE: 9

Asn Cys Val Glu Leu Gln Ala Ser Ala
 1               5

<210> SEQ ID NO 10
<211> LENGTH: 9
<212> TYPE: PRT
<213> ORGANISM: Homo Sapiens

<400> SEQUENCE: 10

Asp Asn His Gly Phe Gly Asn Cys Val
 1               5

<210> SEQ ID NO 11
<211> LENGTH: 14
<212> TYPE: DNA
<213> ORGANISM: Homo Sapiens

<400> SEQUENCE: 11
ttttgatcaa gctt                                                      14

<210> SEQ ID NO 12
<211> LENGTH: 42
<212> TYPE: DNA
<213> ORGANISM: Homo Sapiens

<400> SEQUENCE: 12
ctaatacgac tcactatagg gctcgagcgg ccgcccgggc ag                        42

<210> SEQ ID NO 13
<211> LENGTH: 12
<212> TYPE: DNA
<213> ORGANISM: Homo Sapiens

<400> SEQUENCE: 13
ggcccgtcct ag                                                        12

<210> SEQ ID NO 14
<211> LENGTH: 40
<212> TYPE: DNA
<213> ORGANISM: Homo Sapiens

<400> SEQUENCE: 14
```

```
gtaatacgac tcactatagg gcagcgtggt cgcggccgag                               40
```

<210> SEQ ID NO 15
<211> LENGTH: 10
<212> TYPE: DNA
<213> ORGANISM: Homo Sapiens

<400> SEQUENCE: 15

```
cggctcctag                                                               10
```

<210> SEQ ID NO 16
<211> LENGTH: 22
<212> TYPE: DNA
<213> ORGANISM: Homo Sapiens

<400> SEQUENCE: 16

```
ctaatacgac tcactatagg gc                                                 22
```

<210> SEQ ID NO 17
<211> LENGTH: 22
<212> TYPE: DNA
<213> ORGANISM: Homo Sapiens

<400> SEQUENCE: 17

```
tcgagcggcc gcccgggcag ga                                                 22
```

<210> SEQ ID NO 18
<211> LENGTH: 20
<212> TYPE: DNA
<213> ORGANISM: Homo Sapiens

<400> SEQUENCE: 18

```
agcgtggtcg cggccgagga                                                    20
```

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19

```
atatcgccgc gctcgtcgtc gacaa                                              25
```

<210> SEQ ID NO 20
<211> LENGTH: 26
<212> TYPE: DNA
<213> ORGANISM: Artificial Sequence
<220> FEATURE:
<223> OTHER INFORMATION: Primer

<400> SEQUENCE: 20

```
agccacacgc agctcattgt agaagg                                             26
```

<210> SEQ ID NO 21
<211> LENGTH: 25
<212> TYPE: DNA
<213> ORGANISM: Artificial Sequence
<220> FEATURE:
<223> OTHER INFORMATION: Primer

<400> SEQUENCE: 21

```
cctgcttcag taacaaccac attct                                              25
```

-continued

```
<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22
ctttaccagt ggaatgatga cagg                                          24

<210> SEQ ID NO 23
<211> LENGTH: 30
<212> TYPE: DNA
<213> ORGANISM: Artificial Sequence
<220> FEATURE:
<223> OTHER INFORMATION: Primer

<400> SEQUENCE: 23
gtgtaagctt cccgccgcgt ggtcagcggc                                    30

<210> SEQ ID NO 24
<211> LENGTH: 28
<212> TYPE: DNA
<213> ORGANISM: Artificial Sequence
<220> FEATURE:
<223> OTHER INFORMATION: Primer

<400> SEQUENCE: 24
cacaggatcc tatacctgct tcagtaac                                      28

<210> SEQ ID NO 25
<211> LENGTH: 14
<212> TYPE: PRT
<213> ORGANISM: Homo Sapiens

<400> SEQUENCE: 25

Gly Leu Trp Arg Asn Gly Asp Gly Gln Thr Ser Gly Ala Cys
 1               5                  10

<210> SEQ ID NO 26
<211> LENGTH: 15
<212> TYPE: PRT
<213> ORGANISM: Homo Sapiens

<400> SEQUENCE: 26

Gly Gly Pro Tyr Leu Tyr Gln Trp Asn Asp Asp Arg Cys Asn Met
 1               5                  10                  15

<210> SEQ ID NO 27
<211> LENGTH: 14
<212> TYPE: PRT
<213> ORGANISM: Homo Sapiens

<400> SEQUENCE: 27

Glu Ala Arg Leu Ala Cys Glu Ser Glu Gly Gly Val Leu Leu
 1               5                  10

<210> SEQ ID NO 28
<211> LENGTH: 9
<212> TYPE: PRT
<213> ORGANISM: Homo Sapiens

<400> SEQUENCE: 28

Trp Ile Gly Phe Thr Tyr Lys Thr Ala
 1               5
```

```
<210> SEQ ID NO 29
<211> LENGTH: 9
<212> TYPE: PRT
<213> ORGANISM: Homo Sapiens

<400> SEQUENCE: 29

Ala Thr Gly Glu His Gln Ala Phe Thr
 1               5

<210> SEQ ID NO 30
<211> LENGTH: 9
<212> TYPE: PRT
<213> ORGANISM: Homo Sapiens

<400> SEQUENCE: 30

Phe Gly Asn Cys Val Glu Leu Gln Ala
 1               5

<210> SEQ ID NO 31
<211> LENGTH: 9
<212> TYPE: PRT
<213> ORGANISM: Homo Sapiens

<400> SEQUENCE: 31

Asn Cys Val Glu Leu Gln Ala Ser Ala
 1               5

<210> SEQ ID NO 32
<211> LENGTH: 9
<212> TYPE: PRT
<213> ORGANISM: Homo Sapiens

<400> SEQUENCE: 32

Asp Asn His Gly Phe Gly Asn Cys Val
 1               5

<210> SEQ ID NO 33
<211> LENGTH: 4
<212> TYPE: PRT
<213> ORGANISM: Homo Sapiens

<400> SEQUENCE: 33

Asn Leu Thr Lys
 1

<210> SEQ ID NO 34
<211> LENGTH: 4
<212> TYPE: PRT
<213> ORGANISM: Homo Sapiens

<400> SEQUENCE: 34

Asn Gln Ser Thr
 1

<210> SEQ ID NO 35
<211> LENGTH: 4
<212> TYPE: PRT
<213> ORGANISM: Homo Sapiens

<400> SEQUENCE: 35

Arg Lys Glu Ser
 1
```

```
<210> SEQ ID NO 36
<211> LENGTH: 4
<212> TYPE: PRT
<213> ORGANISM: Homo Sapiens

<400> SEQUENCE: 36

Ser Phe Gln Glu
 1

<210> SEQ ID NO 37
<211> LENGTH: 4
<212> TYPE: PRT
<213> ORGANISM: Homo Sapiens

<400> SEQUENCE: 37

Ser Asp Gly Asp
 1

<210> SEQ ID NO 38
<211> LENGTH: 4
<212> TYPE: PRT
<213> ORGANISM: Homo Sapiens

<400> SEQUENCE: 38

Thr Arg Lys Glu
 1

<210> SEQ ID NO 39
<211> LENGTH: 4
<212> TYPE: PRT
<213> ORGANISM: Homo Sapiens

<400> SEQUENCE: 39

Ser Gly Met Glu
 1

<210> SEQ ID NO 40
<211> LENGTH: 6
<212> TYPE: PRT
<213> ORGANISM: Homo Sapiens

<400> SEQUENCE: 40

Gly Gln Lys Val Cys Phe
 1               5

<210> SEQ ID NO 41
<211> LENGTH: 6
<212> TYPE: PRT
<213> ORGANISM: Homo Sapiens

<400> SEQUENCE: 41

Gly Val Leu Leu Ser Leu
 1               5

<210> SEQ ID NO 42
<211> LENGTH: 6
<212> TYPE: PRT
<213> ORGANISM: Homo Sapiens

<400> SEQUENCE: 42

Gly Thr Gly Ile Ser Asp
 1               5

<210> SEQ ID NO 43
<211> LENGTH: 6
```

-continued

```
<212> TYPE: PRT
<213> ORGANISM: Homo Sapiens

<400> SEQUENCE: 43

Gly Ile Ser Asp Gly Asp
1               5

<210> SEQ ID NO 44
<211> LENGTH: 6
<212> TYPE: PRT
<213> ORGANISM: Homo Sapiens

<400> SEQUENCE: 44

Gly Leu Trp Arg Asn Gly
1               5

<210> SEQ ID NO 45
<211> LENGTH: 6
<212> TYPE: PRT
<213> ORGANISM: Homo Sapiens

<400> SEQUENCE: 45

Gly Gln Thr Ser Gly Ala
1               5

<210> SEQ ID NO 46
<211> LENGTH: 6
<212> TYPE: PRT
<213> ORGANISM: Homo Sapiens

<400> SEQUENCE: 46

Gly Ser Glu Lys Cys Val
1               5

<210> SEQ ID NO 47
<211> LENGTH: 6
<212> TYPE: PRT
<213> ORGANISM: Homo Sapiens

<400> SEQUENCE: 47

Gly Ile Ile Pro Asn Leu
1               5
```

C-TYPE LECTIN TRANSMEMBRANE ANTIGEN EXPRESSED IN HUMAN PROSTATE CANCER AND USES THEREOF

This application claims the benefit of U.S. provisional patent application No. 60/148,935, filed Aug. 12, 1999, the entire contents of which are incorporated herein by reference.

FIELD OF THE INVENTION

The invention described herein relates to a novel gene and its encoded protein, termed PC-LECTIN, and to diagnostic and therapeutic methods and compositions useful in the management of various cancers that express PC-LECTIN, particularly prostate cancers.

BACKGROUND OF THE INVENTION

Cancer is the second leading cause of human death next to coronary disease. Worldwide, millions of people die from cancer every year. In the United States alone, cancer causes the death of well over a half-million people annually, with some 1.4 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Many cancer patients experience a recurrence.

Worldwide, prostate cancer is the fourth most prevalent cancer in men. In North America and Northern Europe, it is by far the most common male cancer and is the second leading cause of cancer death in men. In the United States alone, well over 40,000 men die annually of this disease— second only to lung cancer. Despite the magnitude of these figures, there is still no effective treatment for metastatic prostate cancer. Surgical prostatectomy, radiation therapy, hormone ablation therapy, and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the management of this disease. Although the serum PSA assay has been a very useful tool, its specificity and general utility is widely regarded as lacking in several important respects.

Progress in identifying additional specific markers for prostate cancer has been improved by the generation of prostate cancer xenografts that can recapitulate different stages of the disease in mice. The LAPC Los Angeles Prostate Cancer) xenografts are prostate cancer xenografts that have survived passage in severe combined immune deficient (SCID) mice and have exhibited the capacity to mimic disease progression, including the transition from androgen dependence to androgen independence and the development of metastatic lesions (Klein et al., 1997, Nat. Med.3:402). More recently identified prostate cancer markers include PCTA-1 (Su et al., 1996, Proc. Natl. Acad. Sci. USA 93: 7252), prostate stem cell antigen (PSCA) (Reiter et al., 1998, Proc. Natl. Acad. Sci. USA 95: 1735), and STEAP (Hubert et al., 1999, Proc. Natl. Acad. Sci. USA 96: 14523).

While previously identified markers such as PSA, PSM, PCTA and PSCA have facilitated efforts to diagnose and treat prostate cancer, there is need for the identification of additional markers and therapeutic targets for prostate and related cancers in order to further improve diagnosis and therapy.

SUMMARY OF THE INVENTION

The present invention generally relates to a novel transmembrane antigen overexpressed in human prostate cancer, designated PC-LECTIN. The PC-LECTIN antigen is structurally related to hamster layilin (Borowsky and Hynes, J. Cell Biol. 143:429–42, 1998), a member of the C-type lectin proteins. However, PC-LECTIN does not contain the functional talin association domain found in layilin, and therefore is likely to have a different or modified function. The structural features of PC-LECTIN identify it as a type la transmembrane protein with an extracellular N-terminus and intracellular C-terminus. In addition, the PCLECTIN gene product contains an N-terminal signal sequence. The transmembrane topology of the PC-LECTIN protein has also been established experimentally.

The distribution of PC-LECTIN gene expression in normal human tissues is highly restricted to normal testis. In human prostate cancer, the PC-LECTIN gene is highly overexpressed, as no detectable expression of this gene occurs in normal prostate. The PC-LECTIN gene therefore encodes a prostate tumor antigen, which is useful as a diagnostic and/or prognostic marker, and/or may serve as an excellent target for various therapeutic approaches such as antibody, vaccine and small molecule therapies.

Functionally, PC-LECTIN may be involved in invasion, adhesion or migration. The PC-LECTIN antigen, like Lectin, binds to sugar moieties, opening a further possibility for therapeutic approaches. In one approach, carbohydrate molecules may be used to inhibit PC-LECTIN biological activity. The limited expression of PC-LECTIN in the immune privileged tissue of the testis (where a blood-testis barrier exists) suggests that negative background effects of immunological and other PC-LECTIN specific therapeutic strategies (e.g., carbohydrate inhibition) will be minimal. Given the high level expression observed in prostate cancer, it is possible that PC-LECTIN is also expressed in other human cancers, and to that extent, may similarly be useful as diagnostic and/or prognostic marker of such other cancers, and/or may serve as a tumor antigen target for the treatment of such other cancers. PC-LECTIN may also be shed into serum following ligand binding or activation, as has been observed for several known receptors, including L-Selectin (for review, see: Tedder et al., 1991, Am. J. Respir. Cell. Mol. Biol. 5: 305–306), thereby opening the possibility for serum detection and related diagnostic methods. Background levels of PC-LECTIN would be expected to be low or absent in view of the blood-testis barrier and absence of expression in other normal tissues, suggesting that detection of PC-LECTIN in serum would specifically correlate with the presence of a tumor.

The invention provides polynucleotides corresponding or complementary to all or part of the PC-LECTIN genes, mRNAs, and/or coding sequences, preferably in isolated form, including polynucleotides encoding PC-LECTIN proteins and fragments thereof, DNA, RNA, DNA/RNA hybrid, and related molecules, polynucleotides or oligonucleotides complementary to the PC-LECTIN genes or mRNA sequences or parts thereof, and polynucleotides or oligonucleotides which hybridize to the PC-LECTIN genes, mRNAs, or to PC-LECTIN-encoding polynucleotides. Also provided are means for isolating cDNAs and the genes encoding PC-LECTIN. Recombinant DNA molecules containing PC-LECTIN polynucleotides, cells transformed or transduced with such molecules, and host vector systems for the expression of PC-LECTIN gene products are also provided.

The invention further provides PC-LECTIN proteins and polypeptide fragments thereof, as well as antibodies that bind to PC-LECTIN proteins and polypeptide fragments thereof. The antibodies of the invention include polyclonal and monoclonal antibodies, murine and other mammalian antibodies, chimeric antibodies, humanized and fully human antibodies, antibodies labeled with a detectable marker, and antibodies conjugated to radionuclides, toxins or other therapeutic compositions.

The invention further provides methods for detecting the presence of PC-LECTIN polynucleotides and proteins in various biological samples, as well as methods for identifying cells that express a PC-LECTIN. The invention further provides various therapeutic compositions and strategies for treating prostate cancer, including particularly, antibody, vaccine and small molecule therapy.

BRIEF DESCRIPTION OF THE FIGURES

FIGS. 1A–1D. Nucleotide (SEQ ID NO: 1) and deduced amino acid (SEQ ID NO: 2) sequences of a full-length cDNA encoding the PC-LECTIN gene. The start methionine and putative Kozak sequence are indicated in bold, N-terminal signal sequence is boxed, type-C lectin domains are boxed and shaded transmembrane domain is underlined.

FIG. 2A. Amino acid sequence alignment of human PC-LECTIN (SEQ ID NO: 2) with the reported sequence of hamster layilin (SEQ ID NO: 3; Borowsky and Hynes, J. Cell Biol: 143:42–42,1998).

FIGS. 2B–2C. Nucleotide sequence alignment of human PC-LECTIN cDNA (SEQ ID NO: 4) with reported cDNA sequence of hamster layilin (SEQ ID NO: 5; Borowsky and Hynes, J. Cell Biol:143:42–42,1998) (using LALIGN from the BCM Search Launcher).

FIG. 3A. RT-PCR analysis of PC-LECTIN gene expression in prostate cancer xenografts, normal prostate, and other tissues and cell lines, showing expression in prostate cancer xenografts. Lane 1 is brain; lane 2 is prostate; lane 3 is LAPC-4 AD; lane 4 is LAPC-4 AI; lane 5 is LAPC-9 AD; lane 6 is LAPC-9 AI; lane 7 is HeLa cells; and lane 8 is a negative control.

FIG. 3B. RT-PCR analysis of PC-LECTIN gene expression in various tissues, showing low level expression in placenta at 30 cycles. Lane 1 is brain; lane 2 is heart; lane 3 is kidney; lane 4 is liver; lane 5 is lung; lane 6 is pancreas; lane 7 is placenta; and lane 8 is skeletal muscle.

FIG. 3C. RT-PCR analysis of PC-LECTIN gene expression in normal prostate and other tissues, showing expression in normal testis only at 25 cycles of amplification, and low level expression in prostate and spleen at 30 cycles. Lane 1 is colon; lane 2 is ovary; lane 3 is leukocytes; lane 4 is prostate; lane 5 is small intestine; lane 6 is spleen; lane 7 is testis; and lane 8 is thymus.

FIG. 10A. Immunoprecipitation of PC-LECTIN from Rat1-PC-LECTIN cells. Rat1 cells stably infected with either neo control virus or virus encoding PC-LECTIN were subjected to immunoprecipitation with serum from mice immunized with purified Tag5-PC-LECTIN protein. Western blot analysis was carried out with an affinity purified rabbit anti-PC-LECTIN peptide pAb.

FIG. 10B. Immunoprecipitation of PC-LECTIN from Rat1-PC-LECTIN cells, as described for FIG. 10A, except that western blot analysis was carried out with a 1:1000 dilution of immunized mouse serum.

DETAILED DESCRIPTION OF THE INVENTION

Figure 4A:
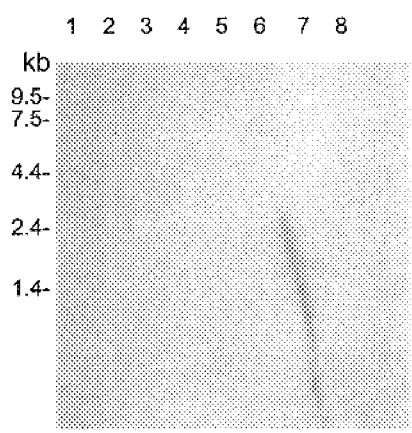
FIG. 4A. Northern blot analyses of PC-LECTIN expression in various normal human tissues, showing no expression of PC-LECTIN in these normal tissues. Lane 1 is heart; lane 2 is brain; lane 3 is placenta; lane 4 is lung; lane 5 is liver; lane 6 is skeletal muscle; lane 7 is kidney; and lane 8 is pancreas.

The invention provides a novel transmembrane antigen, designated PC-LECTIN, that is overexpressed in prostate cancer and is a member of the C-type lectin family of proteins. Expression in normal adult tissues is limited to the testis. Expression was found in prostate cancer xenografts, with higher levels in the androgen-dependent prostate cancer xenografts and lower levels in the androgen-independent xenografts. This expression pattern suggests that PC-LECTIN expression in prostate tumors is dependent on the presence of androgen. PC-LECTIN also shows a carbohydrate binding specificity similar to that observed for the lectin Concanavalin A.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the terms "advanced prostate cancer", "locally advanced prostate cancer", "advanced disease" and "locally advanced disease" mean prostate cancers that have extended through the prostate capsule, and are meant to include stage C disease under the American Urological Association (AUA) system, stage C1–C2 disease under the Whitmore-Jewett system, and stage T3–T4 and N+ disease under the TNM (tumor, node, metastasis) system. In general, surgery is not recommended for patients with locally advanced disease, and these patients have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostatic capsule, extends into the surgical margin, or invades the seminal vesicles.

As used herein, the terms "metastatic prostate cancer" and "metastatic disease" mean prostate cancers that have spread to regional lymph nodes or to distant sites, and are meant to include stage D disease under the AUA system and stage TxNxM+ under the TNM system. As is the case with locally advanced prostate cancer, surgery is generally not indicated for patients with metastatic disease, and hormonal (androgen ablation) therapy is the preferred treatment modality. Patients with metastatic prostate cancer eventually develop an androgen-refractory state within 12 to 18 months of treatment initiation, and approximately half of these patients die within 6 months thereafter. The most common site for prostate cancer metastasis is bone. Prostate cancer bone metastases are, on balance, characteristically osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA.

As used herein, the term "polypeptide" means a polymer of at least 10 amino acids. Throughout the specification, standard three letter or single letter designations for amino acids are used.

As used herein, the terms "hybridize", "hybridizing", "hybridizes" and the like, used in the context of polynucleotides, are meant to refer to conventional hybridization conditions, preferably such as hybridization in 50% formamide/6×SSC/0.1% SDS/100 µg/ml ssDNA, in which temperatures for hybridization are above 37° C. and temperatures for washing in 0.1×SSC/0.1% SDS are above 55° C., and most preferably to stringent hybridization conditions. "Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC (sodium chloride/sodium. citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and %SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

In the context of amino acid sequence comparisons, the term "identity" is used to express the percentage of amino acid residues at the same relative positions that are the same. Also in this context, the term "homology" is used to express the percentage of amino acid residues at the same relative positions that are either identical or are similar, using the conserved amino acid criteria of BLAST analysis, as is generally understood in the art. For example, % identity values may be generated by WU-BLAST-2 (Altschul et al., Methods in Enzymology, 266: 460–480 (1996): http://blast.wustl/edu/blast/README.html). Further details regarding amino acid substitutions, which are considered conservative under such criteria, are provided below.

Additional definitions are provided throughout the subsections that follow.

PC-LECTIN Polynucleotides

One aspect of the invention provides polynucleotides corresponding or complementary to all or part of a PC-LECTIN gene, mRNA, and/or coding sequence, preferably in isolated form, including polynucleotides encoding a PC-LECTIN protein and fragments thereof, DNA, RNA, DNA/RNA hybrid, and related molecules, polynucleotides or oligonucleotides complementary to a PC-LECTIN gene or mRNA sequence or a part thereof, and polynucleotides or oligonucleotides that hybridize to a PC-LECTIN gene, mRNA, or to a PC-LECTIN encoding polynucleotide (collectively, "PC-LECTIN polynucleotides"). As used herein, the PC-LECTIN gene and protein is meant to include the PC-LECTIN genes and proteins specifically described herein and the genes and proteins corresponding to other PC-LECTIN proteins and structurally similar variants of the foregoing. Such other PC-LECTIN proteins and variants will generally have coding sequences that are highly homologous to the PC-LECTIN coding sequence, and preferably will share at least about 50% amino acid identity and at least about 60% amino acid homology (using BLAST criteria), more preferably sharing 70% or greater homology (using BLAST criteria).

One embodiment of a PC-LECTIN polynucleotide is a PC-LECTIN polynucleotide having the sequence shown in FIG. 1A–D (SEQ ID NO: 1). A PC-LECTIN polynucleotide may comprise a polynucleotide having the nucleotide sequence of human PC-LECTIN as shown in FIG. 1A–D (SEQ ID NO: 1), wherein T can also be U; a polynucleotide that encodes all or part of the PC-LECTIN protein; a sequence complementary to the foregoing; or a polynucleotide fragment of any of the foregoing. Another embodiment comprises a polynucleotide having the sequence as shown in FIG. 1A–D (SEQ ID NO: 1), from nucleotide residue number 380 through nucleotide residue number 1201, from nucleotide residue number 443 through nucleotide residue number 1018, or from nucleotide residue number 443 through nucleotide residue number 1201, wherein T can also be U. Another embodiment comprises a polynucleotide encoding a PC-LECTIN polypeptide whose sequence is encoded by the cDNA contained in the plasmid P58P1D12-2 as deposited with American Type Culture Collection on Mar. 10, 1999 as Accession No. 207152. Another embodiment comprises a polynucleotide that is capable of hybridizing under stringent hybridization conditions to the human PC-LECTIN cDNA shown in FIG. 1A–D (SEQ ID NO: 1) or to a polynucleotide fragment thereof.

Typical embodiments of the invention disclosed herein include PC-LECTIN polynucleotides encoding specific portions of the PC-LECTIN mRNA sequence such as those that encode the protein and fragments thereof. For example, representative embodiments of the invention disclosed herein include: polynucleotides encoding about amino acid 1 to about amino acid 10 of the PC-LECTIN protein shown in FIG. 1A–D (SEQ ID NO: 2), polynucleotides encoding about amino acid 20 to about amino acid 30 of the PC-LECTIN protein shown in FIG. 1A–D (SEQ ID NO: 2), polynucleotides encoding about amino acid 30 to about amino acid 40 of the PC-LECTIN protein shown in FIG. 1A–D (SEQ ID NO: 2), polynucleotides encoding about amino acid 40 to about amino acid 50 of the PC-LECTIN protein shown in FIG. 1A–D (SEQ ID NO: 2), polynucleotides encoding about amino acid 50 to about amino acid 60 of the PC-LECTIN protein shown in FIG. 1A–D (SEQ ID NO: 2), polynucleotides encoding about amino acid 60 to about amino acid 70 of the PC-LECTIN protein shown in FIG. 1A–D (SEQ ID NO: 2), polynucleotides encoding about amino acid 70 to about amino acid 80 of the PC-LECTIN protein shown in FIG. 1A–D (SEQ ID NO: 2), polynucleotides encoding about amino acid 80 to about amino acid 90 of the PC-LECTIN protein shown in FIG. 1A–D (SEQ ID NO: 2) and polynucleotides encoding about amino acid 90 to about amino acid 100 of the PC-LECTIN protein shown in FIG. 1A–D (SEQ ID NO: 2), etc. Following this scheme, polynucleotides (of at least 10 amino acids) encoding portions of the amino acid sequence of amino acids 100–273 of the PC-LECTIN protein shown in FIG. 1A–D (SEQ ID NO: 2) are typical embodiments of the invention. Polynucleotides encoding larger portions of the PC-LECTIN protein are also contemplated. For example polynucleotides encoding from about amino acid 1 (or 20 or 30 or 40 etc.) to about amino acid 20, (or 30, or 40 or 50 etc.) of the PC-LECTIN protein shown in FIG. 1A–D (SEQ ID NO: 2) may be generated by a variety of techniques well known in the art.

Additional illustrative embodiments of the invention disclosed herein include PC-LECTIN polynucleotide fragments encoding one or more of the biological motifs contained within the PC-LECTIN protein sequence. In one embodiment, typical polynucleotide fragments of the invention can encode one or more of the regions of PC-LECTIN that exhibit homology to hamster layilin. In another embodiment of the invention, typical polynucleotide fragments can encode one or more of the PC-LECTIN type-C lectin domains or the transmembrane domain, as disclosed in greater detail in the text discussing the PC-LECTIN protein and polypeptides below. In yet another embodiment of the invention, typical polynucleotide fragments can encode sequences that are unique to one or more PC-LECTIN alternative splicing variants.

The polynucleotides of the preceding paragraphs have a number of different specific uses. As PC-LECTIN is shown to be overexpressed in prostate cancers, these polynucleotides may be used in methods assessing the status of PC-LECTIN gene products in normal versus cancerous tissues. Typically, polynucleotides encoding specific regions of the PC-LECTIN protein may be used to assess the presence of perturbations (such as deletions, insertions, point mutations etc.) in specific regions (such regions containing a transmembrane domain) of the PC-LECTIN gene products. Exemplary assays include both RT-PCR assays as well as single-strand conformation polymorphism (SSCP) analysis (see e.g. Marrogi et al., J. Cutan. Pathol. 26(8): 369–378 (1999), both of which utilize polynucleotides encoding specific regions of a protein to examine these regions within the protein.

Other specifically contemplated embodiments of the invention disclosed herein are genomic DNA, cDNAs, ribozymes, and antisense molecules, as well as nucleic acid molecules based on an alternative backbone or including alternative bases, whether derived from natural sources or synthesized. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the PC-LECTIN polynucleotides and polynucleotide sequences disclosed herein.

Antisense technology entails the administration of exogenous oligonucleotides that bind to a target polynucleotide located within the cells. The term "antisense" refers to the fact that such oligonucleotides are complementary to their intracellular targets, e.g., PC-LECTIN. See for example, Jack Cohen, OLIGODEOXYNUCLEOTIDES, Antisense Inhibitors of Gene Expression, CRC Press, 1989; and Synthesis 1:1–5 (1988). The PC-LECTIN antisense oligonucleotides of the present invention include derivatives such as S-oligonucleotides (phosphorothioate derivatives or S-oligos, see, Jack Cohen, supra), which exhibit enhanced cancer cell growth inhibitory action. S-oligos (nucleoside phosphorothioates) are isoelectronic analogs of an oligonucleotide (O-oligo) in which a nonbridging oxygen atom of the phosphate group is replaced by a sulfur atom. The S-oligos of the present invention may be prepared by treatment of the corresponding O-oligos with 3H-1,2-benzodithiol-3-one-1,1-dioxide, which is a sulfur transfer reagent. See Iyer, R. P. et al, J. Org. Chem. 55:4693–4698 (1990); and Iyer, R. P. et al., J. Am. Chem. Soc. 112:1253–1254 (1990), the disclosures of which are fully incorporated by reference herein. Additional PC-LECTIN antisense oligonucleotides of the present invention include morpholino antisense oligonucleotides known in the art (see e.g. Partridge et al., 1996, Antisense & Nucleic Acid Drug Development 6: 169–175).

The PC-LECTIN antisense oligonucleotides of the present invention typically may be RNA or DNA that is complementary to and stably hybridizes with the first 100 N-terminal codons or last 100 C-terminal codons of the PC-LECTIN genome or the corresponding mRNA. While absolute complementarity is not required, high degrees of complementarity are preferred. Use of an oligonucleotide complementary to this region allows for the selective hybridization to PC-LECTIN mRNA and not to mRNA specifying other regulatory subunits of protein kinase. Preferably, the PC-LECTIN antisense oligonucleotides of the present invention are a 15 to 30-mer fragment of the antisense DNA molecule having a sequence that hybridizes to PC-LECTIN mRNA. Optionally, PC-LECTIN antisense oligonucleotide is a 30-mer oligonucleotide that is complementary to a region in the first 10 N-terminal codons and last 10 C-terminal codons of PC-LECTIN. Alternatively, the antisense molecules are modified to employ ribozymes in the inhibition of PC-LECTIN expression. L. A. Couture & D. T. Stinchcomb; *Trends Genet* 12: 510–515 (1996).

Further specific embodiments of this aspect of the invention include primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of a PC-LECTIN polynucleotide in a sample and as a means for detecting a cell expressing a PC-LECTIN protein.

Examples of such probes include polypeptides comprising all or part of the human PC-LECTIN cDNA sequence shown in FIG. 1A–D (SEQ ID NO: 1). Examples of primer pairs capable of specifically amplifying PC-LECTIN mRNAs are also described in the Examples that follow. As will be understood by the skilled artisan, a great many different primers and probes may be prepared based on the sequences provided herein and used effectively to amplify and/or detect a PC-LECTIN mRNA.

As used herein, a polynucleotide is said to be "isolated" when it is substantially separated from contaminant polynucleotides that correspond or are complementary to genes other than the PC-LECTIN gene or that encode polypeptides other than PC-LECTIN gene product or fragments thereof. A skilled artisan can readily employ nucleic acid isolation procedures to obtain an isolated PC-LECTIN polynucleotide.

The PC-LECTIN polynucleotides of the invention are useful for a variety of purposes, including but not limited to their use as probes and primers for the amplification and/or detection of the PC-LECTIN gene(s), mRNA(s), or fragments thereof; as reagents for the diagnosis and/or prognosis of prostate cancer and other cancers; as tools for identifying molecules that inhibit calcium entry specifically into prostate cells; as coding sequences capable of directing the expression of PC-LECTIN polypeptides; as tools for modulating or inhibiting the expression of the PC-LECTIN gene (s) and/or translation of the. PC-LECTIN transcript(s); and as therapeutic agents.

Molecular and Biochemical Features of PC-LECTIN

As is described further in the Examples that follow, the PC-LECTIN gene and protein have been characterized in a variety of ways. For example, analyses of nucleotide coding and amino acid sequences were conducted in order to identify conserved structural elements within the PC-LECTIN sequence, topological features, and potentially related molecules. RT-PCR and northern blot analyses of PC-LECTIN mRNA expression were conducted in order to establish the range of normal and cancerous tissues expressing the various PC-LECTIN messages. Western blot analyses of PC LECTIN protein expression in experimentally transfected cells was conducted to determine cell surface localization.

The PC-LECTIN protein is a type 1a transmembrane cell surface protein of approximately 252 amino acids (initially expressed as a 273 amino acid signal sequence-containing precursor protein) with homology to a hamster protein termed "layilin", which in turn shares homology with the C-type lectins (Borowsky and Hynes, J. C II Bio:1143:429–42, 1998). PC-LECTIN also shows homology to the lectin domains of galactose-binding protein that was initially purified from the hemolymph of Sarcophaga peregrina larvae following body wall injury, termed Sarcophaga lectin (Komano et al., 1980, J. Biol. Chem. 255: 2919–2924), and subsequently cloned (Takahashi et al., 1885 J. Biol. Chem. 22: 12228–12233; Kobayashi et al., 1989, Biochimica et Biophysica Acta 009: 244–250). The cell surface location of the PC-LECTIN protein has been confirmed experimentally, as further described in the Examples sections that follow.

The cDNA nucleotide and deduced amino acid sequences of human PC-LECTIN are shown in FIG. 1A–D (SEQ ID NO: 1,2). An alignment of the amino acid sequence of the PC-LECTIN antigen (SEQ ID NO: 2) with the reported sequence for hamster layilin (SEQ ID NO: 3) is shown in FIG. 2. Although PC-LECTIN bears close homology to hamster layilin (approximately 44.9% identity, over a 265-residue overlap,), it diverges significantly in a key functional domain proposed for the layilin protein. Specifically, the PC-LECTIN protein does not have an approximately 10 amino acid sequence found in the layilin structure which represents a domain believed to be responsible for the layilin protein's association with the cytoskeletal protein talin at cell membrane ruffles (Borowsky and Hynes, J. Cell Bio:1143:429–42, 1998; Critchley et al., Biochem Soc Symp 65:79–99, 1999). At the gene level, alignment of the 2550 bp PC LECTIN cDNA with the 1747 bp cDNA of hamster layilin cDNA shows homology over a 591 bp region. The rest of the PC-LECTIN region is significantly different from layilin, which is reflected in the differences in the amino acid sequence of the c-terminal half of the extracellular domain and the entire cytoplasmic domain. This suggests that while PC LECTIN and layilin are related and probably constitute a sub-family of lectins, PC-LECTIN is unlikely to be the human form of layilin.

Layilin's association with talin is hypothesized to function in cell motility. The absence of the talin association domain in the PC-LECTIN structure suggests that PC-LECTIN may not interact with talin or the cytoskeleton in the same manner as layilin, if at all. In addition to the absence of the talin association domain, the PC-LECTIN structure contains inserted and deleted sequence stretches relative to the layilin structure. The PC-LECTIN expression profile also diverges from that reported for layilin. Although layilin is reported to be expressed in multiple mouse tissues (e.g., ovary, lung, spleen, heart, liver, bladder, lymph node, mammary gland, brain, thyroid and kidney) and cell lines, PC-LECTIN seems very specific to testis among normal human tissues and is up regulated in prostate cancer. This suggests that PC-LECTIN could function as a cell adhesion molecule in metastasis and invasion in prostate cancer arid potentially other cancers. Given its structural relationship with layilin and other C-type lectins, PC-LECTIN is expected to bind to carbohydrate moieties, as has been confirmed. Accordingly, therapeutic strategies utilizing PC-LECTIN-binding carbohydrate molecules to interfere with PC-LECTIN activity may be therapeutically useful in the treatment of cancers expressing PC-LECTIN.

PC-LECTIN expression is essentially testis-specific in normal human tissues, as determined by both RT-PCR and northern blot analysis. In cancer, PC-LECTIN mRNA is overexpressed in human prostate tumor xenografts propagated in SCID mice, and in some cases, very high level expression is seen. Therefore, given its cell surface localization and its high level expression in prostate cancer, PC-LECTIN has all of the hallmark characteristics of an excellent therapeutic target for the treatment of prostate cancer. For these same reasons, PC-LECTIN may also represent an ideal diagnostic marker, particularly in relation to diagnostic imaging. Additionally, it is possible that PC-LECTIN expression increases along with progression of the disease and/or in connection with the emergence of highly aggressive tumors. In this regard, the LAPC-9 prostate tumor xenograft in which very high level expression of PC-LECTIN has been detected was derived from a highly aggressive osteoblastic bone metastasis of prostate cancer.

Isolation of PC-LECTIN-Encoding Nucleic Acid Molecules

The PC-LECTIN cDNA sequences described herein enable the isolation of other polynucleotides encoding PC-LECTIN gene product(s), as well as the isolation of polynucleotides encoding PC-LECTIN gene product homologues, alternatively spliced isoforms, allelic variants, and mutant forms of the PC-LECTIN gene product. Various molecular cloning methods that can be employed to isolate full length cDNAs encoding a PC-LECTIN gene are well known (See, for example, Sambrook, J. et al. Molecular Cloning: A Laboratory Manual, 2d edition., Cold Spring Harbor Press, New York, 1989; Current Protocols in Molecular Biology. Ausubel et al., Eds., Wiley and Sons, 995). For example, lambda phage cloning methodologies may be conveniently employed, using commercially available cloning systems (e.g., Lambda ZAP Express, Stratagene). Phage clones containing PC-LECTIN gene cDNAs may be identified by probing with labeled PC-LECTIN cDNA or a fragment thereof. For example, in one embodiment, the PC-LECTIN cDNA (FIG. 1A–D; SEQ ID NO: 1) or a portion thereof can be synthesized and used as a probe to retrieve overlapping and full length cDNAs corresponding to a PC-LECTIN gene. The PC-LECTIN gene itself may be isolated by screening genomic DNA libraries, bacterial artificial chromosome libraries (BACs), yeast artificial chromosome libraries (YACs), and the like, with PC-LECTIN DNA probes or primers.

Recombinant DNA Molecules and Host-Vector Systems

The invention also provides recombinant DNA or RNA molecules con fining a PC-LECTIN polynucleotide, including but not limited to phages, plasmids, phagemids, cosmids, YACs, BACs, as well as various viral and non-viral vectors well known in the art, and cells transformed or transfected with such recombinant DNA or RNA molecules. As used herein, a recombinant DNA or RNA molecule is a DNA or RNA molecule that ha been subjected to molecular manipulation in vitro. Methods for generating such molecules are well known (see, for example, Sambrook et al, 1989, supra).

The invention further provides a host-vector system comprising a recombinant DNA molecule containing a PC-LECTIN polynucleotide within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 cell). Examples of suitable mammalian cells include various prostate cancer cell lines such LnCaP, PC-3, DU145, LAPC-4, TsuPr1, other transfectable or transducible prostate cancer cell lines, as well as a number of mammalian cells routinely used for the expression of recombinant proteins (e.g., COS, CHO, 293, 293T cells). More particularly, a polynucleotide comprising the coding sequence of a PC-LECTIN may be used to generate PC-LECTIN proteins or fragments thereof using any number of host vector systems routinely used and widely known in the art.

A wide range of host vector systems suitable for the expression of PC LECTIN proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB 11:1785). Using these expression vectors, PC LECTIN may be preferably expressed in several prostate cancer and non-prostate cell lines, including for example 293, 293T, rat-1, 3T3, PC-3, LNCaP and TsuPr1. The host vector systems of the invention are useful for the production of a PC-LECTIN protein or fragment thereof. Such host-vector systems may be employed to study the functional properties of PC-LECTIN and PC-LECTIN mutations.

Proteins encoded by the PC-LECTIN genes, or by fragments thereof, will have a variety of uses, including but not limited to generating antibodies and in methods for identifying ligands and other agents and cellular constituents that bind to a PC-LECTIN gene product. Antibodies raised against a PC-LECTIN protein or fragment thereof may be useful in diagnostic and prognostic assays, imaging methodologies (including, particularly, cancer imaging), and therapeutic methods in the management of human cancers characterized by expression of a PC-LECTIN protein, including but not limited to cancer of the prostate. Various immunological assays useful for the detection of PC-LECTIN proteins are contemplated, including but not limited to various types of radioimmunoassays, enzyme-linked immunosorbent assays (ELISA), enzyme-linked immunofluorescent assays (ELIFA), immunocytochemical methods, and the like. Such antibodies may be labeled and used as immunological imaging reagents capable of detecting prostate cells (e.g., in radioscintigraphic imaging methods). PC-LECTIN proteins may also be particularly useful in generating cancer vaccines, as further described below.

PC-LECTIN Proteins

Another aspect of the present invention provides PC-LECTIN proteins and polypeptide fragments thereof. The PC-LECTIN proteins of the invention include those specifically identified herein, as well as allelic variants, conservative substitution variants and homologs to the extent that such variants and homologs can be isolated/generated and characterized without undue experimentation following the methods outlined below. Fusion proteins that combine parts of different PC-LECTIN proteins or fragments thereof, as well as fusion proteins of a PC-LECTIN protein and a heterologous polypeptide, are also included. Such PC-LECTIN proteins will be collectively referred to as the PC-LECTIN proteins, the proteins of the invention, or PC-LECTIN. As used herein, the term "PC-LECTIN polypeptide" refers to a polypeptide fragment or a PC-LECTIN protein of at least 10 amino acids, preferably at least 15 amino acids.

A specific embodiment of a PC-LECTIN protein comprises a polypeptide having the amino acid sequence of human PC-LECTIN as shown in FIG. 1A–D (SEQ ID NO: 2), from amino acid residue number 1 through about amino acid residue number 273 as shown therein. Another specific embodiment of a PC-LECTIN protein comprises a polypeptide having the amino acid sequence of human PC-LECTIN as shown in FIG. 1A–D (SEQ ID NO: 2), from about amino acid residue number 22 through about amino acid residue number 273 as shown therein. A specific embodiment of a PC-LECTIN fragment comprises a peptide selected from the group comprising WIGFTYKTA, ATGEHQAFT, FGNCVELQA, NCVELQASA, and DNHGFGNCV (SEQ ID NO: 6–10, respectively), or from the group comprising GLWRNGDGQTSGAC (SEQ ID NO: 25), GGPY-LYQWNDDRCNM (SEQ ID NO: 26), EARLACESEG-GVLL (SEQ ID NO: 27), and the extracellular domain of PC-LECTIN (amino acids 22–213 of SEQ ID NO: 2). Other specific embodiments include one or both of the type-C lectin domains and/or the transmembrane domain identified in FIG. 1A–D (SEQ ID NO: 2).

In general, naturally occurring allelic variants of human PC-LECTIN will share a high degree of structural identity and homology (e.g., 90% or more identity). Typically, allelic variants of the PC-LECTIN proteins will contain conservative amino acid substitutions within the PC-LECTIN sequences described herein or will contain a substitution of an amino acid from a corresponding position in a PC-LECTIN homologue. One class of PC-LECTIN allelic variants will be proteins that share a high degree of homology with at least a small region of a particular PC-LECTIN amino acid sequence, but will further contain a radical departure from the sequence, such as a non-conservative substitution, truncation insertion or frame shift.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently b interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

PC-LECTIN proteins, including variants, comprise at least one epitope in common with a PC-LECTIN protein having the amino acid sequence of FIG. 1 (SEQ ID NO: 2), such that an antibody that specifically binds to a PC-LECTIN protein will also specifically bind to the PC-LECTIN protein having the amino acid sequence of FIG. 1 (SEQ ID NO: 2). One class of PC-LECTIN protein variants shares 90% or more identity with the amino acid sequence of FIG. 1 (SEQ ID NO: 2). A more specific class of PC-LECTIN protein variants comprises a C-type-lectin domain. Preferred PC-LECTIN protein variants are capable of binding carbohydrate moieties, particularly with specificity for high mannose residues and/or N-acetylglucosamine.

PC-LECTIN proteins may be embodied in many forms, preferably in isolated form. As used herein, a protein is said to be "isolated" when physical, mechanical or chemical methods are employed to remove the PC-LECTIN protein from cellular constituents that are normally associated with the protein. A skilled artisan can readily employ standard purification methods to obtain an isolated PC-LECTIN protein. A purified PC-LECTIN protein molecule will be substantially free of other proteins or molecules that impair the binding of PC-LECTIN to antibody or other ligand. The nature and degree of isolation and purification will depend on the intended use. Embodiments of a PC-LECTIN protein include a purified PC-LECTIN protein and a functional, soluble PC-LECTIN protein. In one form, such functional, soluble PC-LECTIN proteins or fragments thereof retain the ability to bind antibody or other ligand.

The invention also provides PC-LECTIN polypeptides comprising biologically active fragments of the PC-LECTIN amino acid sequence, such as a polypeptide corresponding to part of the amino acid sequences for PC-LECTIN as shown in FIG. 1A–D (SEQ ID NO: 2). Such polypeptides of the invention exhibit properties of the PC-LECTIN protein, such as the ability to elicit the generation of antibodies that specifically bind an epitope associated with the PC-LECTIN protein.

Embodiments of the invention disclosed herein include a wide variety of art accepted variants of PC-LECTIN proteins such as polypeptides having amino acid insertions, deletions and substitutions. PC-LECTIN variants can be made using methods known in the art such as site-directed mutagenesis, alanine scanning, and PCR mutagenesis. Site-directed mutagenesis [Carter et al., *Nucl. Acids Res.,* 13:4331 (1986); Zoller et al., *Nucl. Acids Res.,* 10:6487 (1987)], cassette mutagenesis [Wells et al., Gene, 34:315 (1985)], restriction selection mutagenesis [Wells et al., *Philos. Trans. R. Soc. London SerA,* 317:415 (1986)] or other known techniques can be performed on the cloned DNA to produce the PC-LECTIN variant DNA. Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins,* (W.H. Freeman & Co., New York); Chothia, J. Mol. Biol., 150:1 (1976)]. If alanine substitution does not yield adequate amounts of variant, an isosteric amino acid can be used.

As discussed above, embodiments of the claimed invention include polypeptides containing less than the 273 amino acid sequence of the PC-LECTIN protein shown in FIG. 1A–D (SEQ ID NO: 2). For example, representative embodiments of the invention disclosed herein include polypeptides consisting of about amino acid 1 to about amino acid 10 of the PC-LECTIN protein shown in FIG. 1A–D (SEQ ID NO: 2), polypeptides consisting of about amino acid 20 to about amino acid 30 of the PC-LECTIN protein shown in FIG. 1A–D (SEQ ID NO: 2), polypeptides consisting of about amino acid 30 to about amino acid 40 of the PC-LECTIN protein shown in FIG. 1A–D (SEQ ID NO: 2), polypeptides consisting of about amino acid 40 to about amino acid 50 of the PC-LECTIN protein shown in FIG. 1A–D (SEQ ID NO: 2), polypeptides consisting of about amino acid 50 to about amino acid 60 of the PC-LECTIN protein shown in FIG. 1A–D (SEQ ID NO: 2), polypeptides consisting of about amino acid 60 to about amino acid 70 of the PC-LECTIN protein shown in FIG. 1A–D (SEQ ID NO: 2), polypeptides consisting of about amino acid 70 to about amino acid 80 of the PC-LECTIN protein shown in FIG. 1A–D (SEQ ID NO: 2), polypeptides consisting of about amino acid 80 to about amino acid 90 of the PC-LECTIN protein shown in FIG. 1A–D (SEQ ID NO: 2) and polypeptides consisting of about amino acid 90 to about amino acid 100 of the PC-LECTIN protein shown in FIG. 1A–D (SEQ ID NO: 2), etc. Following this scheme, polypeptides consisting of portions of the amino acid sequence of amino acids 100–273 of the PC-LECTIN protein are typical embodiments of the invention. Polypeptides consisting of larger portions of the PC-LECTIN protein are also contemplated. For example polypeptides consisting of about amino acid 1 (or 20 or 30 or 40 etc.) to about amino acid 20, (or 30, or 40 or 50 etc.) of the PC-LECTIN protein shown in FIG. 1A–D (SEQ ID NO: 2) may be generated by a variety of techniques well known in the art.

Additional illustrative embodiments of the invention disclosed herein include PC-LECTIN polypeptides containing the amino acid residues of one or more of the biological motifs contained within the PC-LECTIN polypeptide sequence as shown in FIG. 1A–D (SEQ ID NO: 2). In one embodiment, typical polypeptides of the invention can contain one or more of the regions of PC-LECTIN that exhibit homology to hamster layilin, and/or one or more of the transmembrane or C-type lectin domains identified in FIG. 1A–D (SEQ ID NO: 2). In another embodiment, typical polypeptides of the invention can contain one or more of the PC-LECTIN N-glycosylation sites such as NLTK (SEQ ID NO: 33) at residues 86–89 (numbering from first amino acid residue shown in FIG. 1), and/or NQST at residues 255–258

(SEQ ID NO: 34). In another embodiment, typical polypeptides of the invention can contain one or more of the PC-LECTIN cAMP/cGMP-dependent protein kinase phosphorylation sites such as RKES at residues 266–269 (SEQ ID NO: 35). In another embodiment, typical polypeptides of the invention can contain one or more of the PC-LECTIN protein kinase C phosphorylation sites such as SSR at residues 49–51, SEK at residues 141–143, STR at residues 264–266, and/or TRK at residues 264–267. In another embodiment, typical polypeptides of the invention can contain one or more of the PC-LECTIN casein kinase II phosphorylation sites such as SFQE at residues 53–56 (SEQ ID NO: 36), SDGD at residues 95–98 (SEQ ID NO: 37), TRKE at residues 265–268 (SEQ ID NO: 38), and/or SGME at residues 269–272 (SEQ ID NO: 39). In another embodiment, typical polypeptides of the invention can contain one or more of the N-myristoylation sites such as GQKVCF at residues 27–32 (SEQ ID NO: 40), GVLLSL at residues 66–71 (SEQ ID NO: 71), GTGISD at residues 91–96 (SEQ ID NO: 42), GISDGD at residues 93–98 (SEQ ID NO: 43), GLWRNG at residues 102–107 (SEQ ID NO: 44), GQTSGA at residues 109–114 (SEQ ID NO: 45), GSEKCV at residues 140–145 (SEQ ID NO: 46), and/or GIIPNL at residues 212–217 (SEQ ID NO: 47). Related embodiments of these inventions include polypeptides containing combinations of the different motifs discussed above with preferable embodiments being those that contain no insertions, deletions or substitutions either within the motifs or the intervening sequences of these polypeptides.

PC-LECTIN polypeptides can be generated using standard peptide synthesis technology or using chemical cleavage methods well known in the art based on the amino acid sequences of the human PC-LECTIN proteins disclosed herein. Alternatively, recombinant methods can be used to generate nucleic acid molecules that encode a polypeptide fragment of a PC-LECTIN protein. In this regard, the PC-LECTIN-encoding nucleic acid molecules described herein provide means for generating defined fragments of PC-LECTIN proteins. PC-LECTIN polypeptides are particularly useful in generating and characterizing domain specific antibodies (e.g., antibodies recognizing an extracellular or intracellular epitope of a PC-LECTIN protein), in identifying agents or cellular factors that bind to PC-LECTIN or a particular structural domain thereof, and in various therapeutic contexts, including but not limited to cancer vaccines. PC-LECTIN polypeptides containing particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments containing such structures are particularly useful in generating subunit specific anti-PC-LECTIN antibodies or in identifying cellular factors that bind to PC-LECTIN.

In a specific embodiment described in the examples that follow, a secreted form of PC-LECTIN may be conveniently expressed in 293T cells transfected with a CMV-driven expression vector encoding PC-LECTIN with a C-terminal 6×His and MYC tag (pcDNA3.1/mycHIS, Invitrogen). The secreted HIS-tagged PSCA in the culture media may be purified using a nickel column using standard techniques. Alternatively, an AP-tag system may be used (see Example 7).

Modifications of PC-LECTIN such as covalent modifications are included within the scope of this invention. One type of covalent modification includes reacting targeted amino acid residues of an PC-LECTIN polypeptide with an organic derivatizing agent that is capable of reacting with selected side chains or the N- or C-terminal residues of the PC-LECTIN. Another type of covalent modification of the PC-LECTIN polypeptide included within the scope of this invention comprises altering the native glycosylation pattern of the polypeptide. "Altering the native glycosylation pattern" is intended for purposes herein to mean deleting one or more carbohydrate moieties found in native sequence PC-LECTIN (either by removing the underlying glycosylation site or by deleting the glycosylation by chemical and/or enzymatic means), and/or adding one or more glycosylation sites that are not present in the native sequence PC-LECTIN. In addition, the phrase includes qualitative changes in the glycosylation of the native proteins, involving a change in the nature and proportions of the various carbohydrate moieties present. Another type of covalent modification of PC-LECTIN comprises linking the PC-LECTIN polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PC-LECTIN of the present invention may also be modified in a way to form a chimeric molecule comprising PC-LECTIN fused to another, heterologous polypeptide or amino acid sequence. In one embodiment, such a chimeric molecule comprises a fusion of the PC-LECTIN with a polyhistidine epitope tag, which provides an epitope to which immobilized nickel can selectively bind. The epitope tag is generally placed at the amino- or carboxyl-terminus of the PC-LECTIN. In an alternative embodiment, the chimeric molecule may comprise a fusion of the PC-LECTIN with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an PC-LECTIN polypeptide in place of at least one variable region within an Ig molecule. In a particularly preferred embodiment, the immunoglobulin fusion includes the hinge, CH2 and CH3, or the hinge, CHI, CH2 and CH3 regions of an IgG1 molecule. For the production of immunoglobulin fusions see also U.S. Pat. No. 5,428,130 issued Jun. 27, 1995.

PC-LECTIN Antibodies

Another aspect of the invention provides antibodies that bind to PC-LECTIN proteins and polypeptides. The most preferred antibodies will selectively bind to a PC-LECTIN protein and will not bind (or will bind weakly) to non-PC-LECTIN proteins and polypeptides. Anti-PC-LECTIN antibodies that are particularly contemplated include monoclonal and polyclonal antibodies as well as fragments containing the antigen-binding domain and/or one or more complementarity determining regions of these antibodies. As used herein, an antibody fragment is defined as at least a portion of the variable region of the immunoglobulin molecule that binds to its target, i.e., the antigen binding region.

For some applications, it may be desirable to generate antibodies that specifically react with a particular PC-LECTIN protein and/or an epitope within a particular structural domain. For example, preferred antibodies useful for cancer therapy and diagnostic imaging purposes are those which react with an epitope in an extracellular region of the PC-LECTIN protein as expressed in cancer cells. Such antibodies may be generated by using the PC-LECTIN proteins described herein, or using peptides derived from predicted extracellular domains thereof, as an immunogen. In this regard, with reference to the PC-LECTIN protein sequence shown in FIG. 1, regions in the sequence amino-terminal to the transmembrane domain may be selected as used to design appropriate immunogens and screening reagents for raising and selecting extracellular-specific PC-LECTIN antibodies.

PC-LECTIN antibodies of the invention may be particularly useful in prostate cancer therapeutic strategies, diagnostic and prognostic assays, and imaging methodologies. Similarly, such antibodies may be useful in the treatment, diagnosis, and/or prognosis of other cancers, to the extent PC-LECTIN is also expressed or overexpressed in other types of cancer. The invention provides various immunological assays useful for the detection and quantification of PC-LECTIN and mutant PC-LECTIN proteins and polypeptides. Such assays generally comprise one or more PC-LECTIN antibodies capable of recognizing and binding a PC-LECTIN or mutant PC-LECTIN protein, as appropriate, and may be performed within various immunological assay formats well known in the art, including but not limited to various types of radioimmunoassays, enzyme-linked immunosorbent assays (ELI SA), enzyme-linked immunofluorescent assays (ELIFA), and the like. In addition, immunological imaging methods capable of detecting prostate cancer are also provided by the invention, including but limited to radioscintigraphic imaging methods using labeled PC-LECTIN antibodies. Such assays may be used clinically in the detection, monitoring, and prognosis of prostate cancer, particularly advanced prostate cancer.

PC-LECTIN antibodies may also be used in methods for purifying PC-LECTIN and mutant PC-LECTIN proteins and polypeptides and for isolating PC-LECTIN homologues and related molecules. For example, in one embodiment, the method of purifying a PC-LECTIN protein comprises incubating a PC-LECTIN antibody, which has been coupled to a solid matrix, with a lysate or other solution containing PC-LECTIN under conditions which permit the PC-LECTIN antibody to bind to PC-LECTIN; washing the solid matrix to eliminate impurities; and eluting the PC-LECTIN from the coupled antibody. Other uses of the PC-LECTIN antibodies of the invention include generating anti-idiotypic antibodies that mimic the PC-LECTIN protein.

PC-LECTIN antibodies may also be used therapeutically by, for example, modulating or inhibiting the biological activity of a PC-LECTIN protein or targeting and destroying prostate cancer cells expressing a PC-LECTIN protein. Antibody therapy of prostate and other cancers is more specifically described in a separate subsection below.

Various methods for the preparation of antibodies are well known in the art. For example, antibodies may be prepared by immunizing a suitable mammalian host using a PC-LECTIN protein, peptide, or fragment, in isolated or immunoconjugated form (Antibodies: A Laboratory Manual, CSH Press, Eds., Harlow, and Lane (1988); Harlow, Antibodies, Cold Spring Harbor Press, New York (1989)). Examples of protein immunogens include recombinant PC-LECTIN (expressed in a baculovirus system, mammalian system, etc.), PC-LECTIN extracellular domain, AP-tagged PC-LECTIN, etc. In addition, fusion proteins of PC-LECTIN may also be used, such as a PC-LECTIN GST-fusion protein. In a particular embodiment, a GST fusion protein comprising all or most of the open reading frame amino acid sequence of FIG. 1A–D (SEQ ID NO: 2) may be produced and used as an immunogen to generate appropriate antibodies. Cells expressing or overexpressing PC-LECTIN may also be used for immunizations. Similarly, any cell engineered to express PC-LECTIN may be used. Such strategies may result in the production of monoclonal antibodies with enhanced capacities for recognizing endogenous PC-LECTIN. Another useful immunogen comprises PC-LECTIN peptides linked to the plasma membrane of sheep red blood cells.

The amino acid sequence of PC-LECTIN as shown in FIG. 1A–D (SEQ ID NO: 2) may be used to select specific regions of the PC-LECTIN protein for generating antibodies. For example, hydrophobicity and hydrophilicity analyses of the PC-LECTIN amino acid sequence may be used to identify hydrophilic regions in the PC-LECTIN structure. Regions of the PC-LECTIN protein that show immunogenic structure, as well as other regions and domains, can readily be identified using various other methods known in the art, such as Chou-Fasman, Garnier Robson, Kyte-Doolittle, Eisenberg, Karplus-Schultz or Jameson-Wolf analysis. Peptides of PC-LECTIN predicted to bind HLA-A2, such as WIGFTYKTA (SEQ ID NO: 6), ATGEHQAFT(SEQ ID NO: 7), FGNCVELQA (SEQ ID NO: 8), NCVELQASA (SEQ ID NO: 9), and DNHGFGNCV (SEQ ID NO: 10), may be selected for the generation of antibodies. As discussed in the examples below, immunogenicity has been demonstrated with the peptides GLWRNGDGQTSGAC (SEQ ID NO: 25), GGPYLYQWNDDRCNM (SEQ ID NO: 26), EARLACESEGGVLL (SEQ ID NO: 27), and the extracellular domain of PC-LECTIN (amino acids 22–213 of SEQ ID NO: 2), which were used to generate polyclonal and monoclonal antibodies using rabbits and mice, respectively.

Methods for preparing a protein or polypeptide for use as an immunogen and for preparing immunogenic conjugates of a protein with a carrier such as BSA, KLH, or other carrier proteins are well known in the art. In some circumstances, direct conjugation using, for example, carbodiimide reagents may be used; in other instances linking reagents such as those supplied by Pierce Chemical Co., Rockford, Ill., may be effective. Administration of a PC-LECTIN immunogen is conducted generally by injection over a suitable period and with use of a suitable adjuvant, as is generally understood in the art. During the immunization schedule, titers of antibodies can be taken to determine adequacy of antibody formation.

PC-LECTIN monoclonal antibodies are preferred and may be produced by various means well known in the art. For example, immortalized cell lines which secrete a desired monoclonal antibody may be prepared using the standard hybridoma technology of Kohler and Milstein or modifications which immortalize producing B cells, a is generally known. The immortalized cell lines secreting the desired antibodies are screened by immunoassay in which the antigen is the PC-LECTIN protein or PC-LECTIN fragment. When the appropriate immortalized cell culture secreting the desired antibody is identified, the cells may be expanded and antibodies produced either from in vitro cultures or from ascites fluid.

The antibodies or fragments may also be produced, using current technology, by recombinant means. Regions that bind specifically to the desired regions of the PC-LECTIN protein can also be proud in the context of chimeric or CDR grafted antibodies of multiple species origin. Humanized or human PC-LECTIN antibodies may also be produced and are preferred for use in therapeutic contexts. Methods for humanizing murine and other non-human antibodies by substituting one or more of the non-human antibody CDRs for corresponding human antibody sequences are well known (see for example, Jones et al., 1986, Nature 321: 522–525; Riechmann et al., 1988, Nature 332: 323–327; Verhoeyen et al., 1988, Science 239:1534–1536). See also, Carter et al., 1993, Proc. Nat'l. Acad. Sci. USA 89: 4285 and Sims et al., 1993, J. Immunol. 151: 2296. Methods for producing fully human monoclonal antibodies include phage display and transgenic animal technologies (for review, see Vaughan et al., 1998, Nature Biotechnology 16: 535–539).

Fully human PC-LECTIN monoclonal antibodies may be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man. Clark, M. (Ed.), Nottingham Academic, pp 45–64 (1993); Burton and Barbas, Human Antibodies from combinatorial libraries. Id., pp 65–82). Fully human PC-LECTIN monoclonal antibodies may also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607–614). This method avoids the in vitro manipulation required with phage display technology and efficiently produces high affinity authentic human antibodies.

Reactivity of PC-LECTIN antibodies with a PC-LECTIN protein may be established by a number of well known means, including western blot, immunoprecipitation, ELISA, and FACS analyses using, as appropriate, PC-LECTIN proteins, peptides, PC-LECTIN expressing cells or extracts thereof.

A PC-LECTIN antibody or fragment thereof of the invention may be labeled with a detectable marker or conjugated to a second molecule, such as a cytotoxic agent, and used for targeting the second molecule to a PC-LECTIN positive cell (Vitetta, E. S. et al., 1993, Immunotoxin therapy, in DeVita, Jr., V. T. et al., eds., Cancer: Principles and Practice of Oncology, 4th ed., J.B. Lippincott Co., Philadelphia, 2624–2636). Examples of cytotoxic agents include, but are not limited to, ricin, ricin A-chain, doxorubicin, daunorubicin, taxol, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, arbrin A chain, modeccin A chain, alpha-sarcin, gelonin, mitogellin, retstrictocin, phenomycin, enomycin, curicin, crotin, calicheamicin, sapaonaria officinalis inhibitor, and glucocorticoid and other chemotherapeutic agents, as well as radioisotopes such as $^{212}$Bi, $^{131}$I, $^{131}$In, $^{90}$Y, and $^{186}$Re. Suitable detectable markers include, but are not limited to, a radioisotope, a fluorescent compound, a bioluminescent compound, chemiluminescent compound, a metal chelator or an enzyme. Antibodies may also be conjugated to an anti-cancer pro-drug activating enzyme capable of converting the pro-drug to its active form. See, for example, U.S. Pat. No. 4,975,287.

Further, bi-specific antibodies specific for two or more PC-LECTIN epitopes may be generated using methods generally known in the art. Further, antibody effector functions may be modified to enhance the therapeutic effect of PC-LECTIN antibodies on cancer cells. For example, cysteine residues may be engineered into the Fc region, permitting the formation of interchain disulfide bonds and the generation of homodimers which may have enhanced capacities for internalization, ADCC and/or complement mediated cell killing (see, for example, Caron et al., 1992, J. Exp. Med. 176: 1191–1195; Shopes, 1992, J. Immunol. 148: 2918–2922). Homodimeric antibodies may also be generated by cross-linking techniques known in the art (e.g., Wolff et al., Cancer Res. 53: 2560–2565).

PC-LECTIN Transgenic Animals

Nucleic acids that encode PC-LECTIN or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA that is integrated into the genome of a cell from which a transgenic animal develops. In one embodiment, cDNA encoding PC-LECTIN can be used to clone genomic DNA encoding PC-LECTIN in accordance with established techniques and the genomic sequences used to generate transgenic animals that contain cells that express DNA encoding PC-LECTIN.

Methods for generating transgenic animals, particularly animals such as mice or rats, have become conventional in the art and are described, for example, in U.S. Pat. Nos. 4,736,866 and 4,870,009. Typically, particular cells would be targeted for PC-LECTIN transgene incorporation with tissue-specific enhancers. Transgenic animals that include a copy of a transgene encoding PC-LECTIN introduced into the germ line of the animal at an embryonic stage can be used to examine the effect of increased expression of DNA encoding PC-LECTIN. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PC-LECTIN can be used to construct a PC-LECTIN "knock out" animal that has a defective or altered gene encoding PC-LECTIN as a result of homologous recombination between the endogenous gene encoding PC-LECTIN and altered genomic DNA encoding PC-LECTIN introduced into an embryonic cell of the animal. For example, cDNA encoding PC-LECTIN can be used to clone genomic DNA encoding PC-LECTIN in accordance with established techniques. A portion of the genomic DNA encoding PC-LECTIN can be deleted or replaced with another gene, such as a gene encoding a selectable marker that can be used to monitor integration.

Typically, several kilobases of unaltered flanking DNA (both at the 5' and 3' ends) are included in the vector (see e.g., Thomas and Capecchi, 1987, Cell 51:503 for a description of homologous recombination vectors). The vector is introduced into an embryonic stem cell line (e.g., by electroporation) and cells in which the introduced DNA has homologously recombined with the endogenous DNA are selected (see e.g., Li et al., 1992, Cell 69:915). The selected cells are then injected into a blastocyst of an animal (e.g., a mouse or rat) to form aggregation chimeras (see e.g., Bradley, in *Teratocarcinomas and Embryonic Stem Cells: A Practical Approach*, E. J. Robertson, ed., IRL, Oxford, 1987, pp. 113–152).

A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the PC-LECTIN polypeptide.

Methods for the Detection of PC-LECTIN

Another aspect of the present invention relates to methods for detecting PC-LECTIN polynucleotides and PC-LECTIN proteins and variants thereof, as well as methods for identifying a cell that expresses PC-LECTIN. PC-LECTIN appears to be expressed in the LAPC xenografts that are derived from lymph-node and bone metastasis of prostate cancer, and the expression profile of PC-LECTIN makes it a potential diagnostic marker for metastasized disease. In this context, the status of PC-LECTIN gene products may provide information useful for predicting a variety of factors including susceptibility to advanced stage disease, rate of progression, and/or tumor aggressiveness. As discussed in detail below, the status of PC-LECTIN gene products in patient samples may be analyzed by a variety protocols that are well known in the art including immunohistochemical analysis, the variety of northern blotting techniques including in situ hybridization, RT-PCR analysis (for example on laser capture micro-dissected samples), western blot analysis and tissue array analysis.

More particularly, the invention provides assays for the detection of PC-LECTIN polynucleotides in a biological sample, such as serum, bone, prostate, and other tissues, urine, semen, cell preparations, and the like. Detectable PC-LECTIN polynucleotides include, for example, a PC-LECTIN gene or fragments thereof, PC-LECTIN mRNA, alternative splice variant PC-LECTIN mRNAs, and recombinant DNA or RNA molecules containing a PC-LECTIN polynucleotide. A number of methods for amplifying and/or detecting the presence of PC-LECTIN polynucleotides are well known in the art and may be employed in the practice of this aspect of the invention.

In one embodiment, a method for detecting a PC-LECTIN mRNA in a biological sample comprises producing cDNA from the sample by reverse transcription using at least one primer; amplifying the cDNA so produced using PC-LECTIN polynucleotides as sense and antisense primers to amplify PC-LECTIN cDNAs therein; and detecting the presence of the amplified PC-LECTIN cDNA. Optionally, the sequence of the amplified PC-LECTIN cDNA can be determined. In another embodiment, a method of detecting a PC-LECTIN gene in a biological sample comprises first isolating genomic DNA from the sample; amplifying the isolated genomic DNA using PC-LECTIN polynucleotides as sense and antisense primers to amplify the PC-LECTIN gene therein; and detecting the presence of the amplified PC-LECTIN gene. Any number of appropriate sense and antisense probe combinations may be designed from the nucleotide sequences provided for the PC-LECTIN (FIG. 1A–D; SEQ ID NO: 1) and used for this purpose.

The invention also provides assays for detecting the presence of a PC-LECTIN protein in a tissue of other biological sample such as serum, bone, prostate, and other tissues, urine, cell preparations, and the like. Methods for detecting a PC-LECTIN protein are also well known and include, for example, immunoprecipitation, immunohistochemical analysis, western blot analysis, molecular binding assays, ELISA, ELIFA and the like. For example, in one embodiment, a method of detecting the presence of a PC-LECTIN protein in a biological sample comprises first contacting the sample with a PC-LECTIN antibody, a PC-LECTIN-reactive fragment thereof, or a recombinant protein containing an antigen binding region of a PC-LECTIN antibody; and then detecting the binding of PC-LECTIN protein in the sample thereto.

Methods for identifying a cell that expresses PC-LECTIN are also provided. In one embodiment, an assay for identifying a cell that expresses a PC-LECTIN gene comprises detecting the presence of PC-LECTIN mRNA in the cell. Methods for the detection of particular mRNAs in cells are well known and include, for example, hybridization assays using complementary DNA probes (such as in situ hybridization using labeled PC-LECTIN riboprobes, northern blot and related techniques) and various nucleic acid amplification assays (such as RT-PCR using complementary primers specific for PC-LECTIN, and other amplification type detection methods, such as, for example, branched DNA, SISBA, TMA and the like). Alternatively, an assay for identifying a cell that expresses a PC-LECTIN gene comprises detecting the presence of PC-LECTIN protein in the cell or secreted by the cell. Various methods for the detection of proteins are well known in the art and may be employed for the detection of PC-LECTIN proteins and PC-LECTIN expressing cells.

PC-LECTIN expression analysis may also be useful as a tool for identifying and evaluating agents that modulate PC-LECTIN gene expression. For example, PC-LECTIN expression is restricted to normal testis, as well as to prostate cancer, and PC-LECTIN may also be expressed in other cancers. Identification of a molecule or biological agent that could inhibit PC-LECTIN expression or over-expression in cancer cells may be of therapeutic value. Such an agent may be identified by using a screen that quantifies PC-LECTIN expression by RT-PCR, nucleic acid hybridization or antibody binding.

Monitoring the Status of PC-LECTIN and its Products

Assays that evaluate the status of the PC-LECTIN gene and PC-LECTIN gene products in an individual may provide information on the growth or oncogenic potential of a biological sample from this individual. For example, because PC-LECTIN mRNA is so highly expressed in prostate cancers, and not in most normal tissue, assays that evaluate the relative levels of PC-LECTIN mRNA transcripts or proteins in a biological sample may be used to diagnose a disease associated with PC-LECTIN dysregulation, such as cancer, and may provide prognostic information useful in defining appropriate therapeutic options. Similarly, assays that evaluate the integrity PC-LECTIN nucleotide and amino acid sequences in a biological sample, may also be used in this context.

The finding that PC-LECTIN mRNA is so highly expressed in prostate cancers, and not in most normal tissue, provides evidence that this gene is associated with dysregulated cell growth and therefore identifies this gene and its products as targets that the skilled artisan can use to evaluate biological samples from individuals suspected of having a disease associated with PC-LECTIN dysregulation. In another example, because the expression of PC-LECTIN is normally restricted to testis, one can also evaluate biological samples taken from other tissues to detect PC-LECTIN expression as an indication of metastasis. In this context, the evaluation of the expression status of PC-LECTIN gene and its products can be used to gain information on the disease potential of a tissue sample. The terms "expression status" in this context is used to broadly refer to the variety of factors involved in the expression, function and regulation of a gene and its products such as the level of mRNA expression, the integrity of the expressed gene products (such as the nucleic and amino acid sequences) and transcriptional and translational modifications to these molecules.

The expression status of PC-LECTIN may provide information useful for predicting susceptibility to particular disease stages, progression, and/or tumor aggressiveness. The invention provides methods and assays for determining PC-LECTIN expression status and diagnosing cancers that express PC-LECTIN, such as cancers of the prostate, breast, bladder, lung, bone, colon, pancreatic, testicular, cervical and ovarian cancers. PC-LECTIN expression status in patient samples may be analyzed by a number of means well known in the art, including without limitation, immunohistochemical analysis, in situ hybridization, RT-PCR analysis on laser capture micro-dissected samples, western blot analysis of clinical samples and cell lines, and tissue array analysis. Typical protocols for evaluating the expression status of the PC-LECTIN gene and gene products can be found, for example in *Current Protocols In Molecular Biology*, Units 2 [Northern Blotting], 4 [Southern Blotting], [Immunoblotting] and 18 [PCR Analysis], Frederick M. Ausubul et al. eds., 1995.

In one aspect, the invention provides methods for monitoring PC-LECTIN gene products by determining the status of PC-LECTIN gene products expressed by cells in a test tissue sample from an individual suspected of having a disease associated with dysregulated cell growth (such as hyperplasia or cancer) and then comparing the status so determined to the status of PC-LECTIN gene products in a corresponding normal sample, the presence of aberrant PC-LECTIN gene products in the test sample relative to the normal sample providing an indication of the presence of dysregulated cell growth within the cells of the individual.

In another aspect, the invention provides assays useful in determining the presence of cancer in an individual, comprising detecting a significant increase in PC-LECTIN mRNA or protein expression in a test cell or tissue sample relative to expression levels in the corresponding normal cell or tissue. The presence of PC-LECTIN mRNA may, for example, be evaluated in tissue samples including but not limited to colon, lung, prostate, pancreas, bladder, breast, ovary, cervix, testis, head and neck, brain, stomach, bone, etc. The presence of significant PC-LECTIN expression in any of these tissues may be useful to indicate the emergence, presence and/or severity of these cancers or a metastasis of cancer originating in another tissue, since the corresponding normal tissues do not express PC-LECTIN mRNA or express it at lower levels.

In a related embodiment, PC-LECTIN expression status may be determined at the protein level rather than at the nucleic acid level. For example, such a method or assay would comprise determining the level of PC-LECTIN protein expressed by cells in a test tissue sample and comparing the level so determined to the level of PC-LECTIN expressed in a corresponding normal sample. In one embodiment, the presence of PC-LECTIN protein is evaluated, for example, using immunohistochemical methods. PC-LECTIN antibodies or binding partners capable of detecting PC-LECTIN protein expression may be used in a variety of assay formats well known in the art for this purpose.

In other related embodiments, one can evaluate the integrity PC-LECTIN nucleotide and amino acid sequences in a biological sample in order to identify perturbations in the structure of these molecules such as insertions, deletions, substitutions and the like. Such embodiments are useful because perturbations in the nucleotide and amino acid sequences are observed in a large number of proteins associated with a growth dysregulated phenotype (see e.g. Marrogi et al., J. Cutan. Pathol. 26(8): 369–378 (1999)). In this context, a wide variety of assays for observing perturbations in nucleotide and amino acid sequences are well known in the art. For example, the size and structure of nucleic acid or amino acid sequences of PC-LECTIN gene products may be observed by the northern, Southern, western, PCR and DNA sequencing protocols discussed herein. In addition, other methods for observing perturbations in nucleotide and amino acid sequences such as single strand conformation polymorphism analysis are well known in the art (see e.g. U.S. Pat. Nos. 5,382,510 and 5,952,170).

In another embodiment, one can examine the methylation status of the PC-LECTIN gene in a biological sample. Aberrant demethylation and/or hypermethylation of CpG islands in gene 5' regulatory regions frequently occurs in immortalized and transformed cells and can result in altered expression of various genes. For example, promoter hypermethylation of the. pi-class glutathione S-transferase (a protein expressed in normal prostate but not expressed in >90% of prostate carcinomas) appears to permanently silence transcription of this gene and is the most frequently detected genomic alteration in prostate carcinomas (De Marzo et al., Am. J. Pathol. 155(6): 1985–1992 (1999)). In addition, this alteration is present in at least 70% of cases of high-grade prostatic intraepithelial neoplasia (PIN) (Brooks et al, Cancer Epidemiol. Biomarkers Prev., 1998, 7:531–536).

In another example, expression of the LAGE-I tumor specific gene (which is not expressed in normal prostate but is expressed in 25–50% of prostate cancers) is induced by deoxy-azacytidine in lymphoblastoid cells, suggesting that tumoral expression is due to demethylation (Lethe et al., 1998, Int. J. Cancer 76(6): 903–908). In this context, a variety of assays for examining methylation status of a gene are well known in the art. For example, one can utilize in Southern hybridization approaches methylation-sensitive restriction enzymes which can not cleave sequences that contain methylated CpG sites in order to assess the overall methylation status of CpG islands.

In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in *Current Protocols In Molecular Biology*, Units 12, Frederick M. Ausubel et al. eds., 1995.

In another related embodiment, the invention provides assays useful in determining the presence of cancer in an individual, comprising detecting a significant change in the PC-LECTIN alternative splice variants expressed in a test cell or tissue sample relative to expression levels in the corresponding normal cell or tissue. The monitoring of alternative splice variants of PC-LECTIN is useful because changes in the alternative splicing of proteins is suggested as one of the steps in a series of events that lead to the progression of cancers (see e.g. Carstens et al., Oncogene 15(250: 3059–3065 (1997)).

Gene amplification provides an additional method of assessing the status of PC-LECTIN. Gene amplification may be measured in a sample directly, for example, by conventional Southern blotting, northern blotting to quantitate the transcription of mRNA [Thomas, *Proc. Natl. Acad. Sci. USA,* 77:5201–5205 (1980)], dot blotting (DNA analysis), or in situ hybridization using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

In addition to the tissues discussed above, peripheral blood may be conveniently assayed for the presence of cancer cells, including but not limited to prostate cancers, using RT-PCR to detect PC-LECTIN expression. The presence of RT-PCR amplifiable PC-LECTIN mRNA provides an indication of the presence of the cancer. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25: 373–384; Ghossein et al., 1995, J. Clin. Oncol. 13: 1195–2000; Heston et al., 1995, Clin. Chem. 41: 1687–1688). RT-PCR assays are well known in the art.

A related aspect of the invention is directed to predicting susceptibility to developing cancer in an individual. In one embodiment, a method for predicting susceptibility to cancer comprises detecting PC-LECTIN mRNA or PC-LECTIN protein in a tissue sample, its presence indicating susceptibility to cancer, wherein the degree of PC-LECTIN mRNA expression present is proportional to the degree of susceptibility. In-a specific embodiment, the presence of PC-LECTIN in prostate tissue is examined, with the presence of PC-LECTIN in the sample providing an indication of prostate cancer susceptibility (or the emergence or existence of a prostate tumor). In a closely related embodiment, one can evaluate the integrity PC-LECTIN nucleotide and amino acid sequences in a biological sample in order to identify perturbations in the structure of these molecules such as insertions, deletions, substitutions and the like, with the presence of one or more perturbations in PC-LECTIN gene products in the sample providing an indication of cancer susceptibility (or the emergence or existence of a tumor).

Yet another related aspect of the invention is directed to methods for gauging tumor aggressiveness. In one embodiment, a method for gauging aggressiveness of a tumor comprises determining the level of PC-LECTIN mRNA or PC-LECTIN protein expressed by cells in a sample of the tumor, comparing the level so determined to the level of PC-LECTIN mRNA or PC-LECTIN protein expressed in a corresponding normal tissue taken from the same individual or a normal tissue reference sample, wherein the degree of PC-LECTIN mRNA or PC-LECTIN protein expression in the tumor sample relative to the normal sample indicates the degree of aggressiveness. In a specific embodiment, aggressiveness of prostate tumors is evaluated by determining the extent to which PC-LECTIN is expressed in the tumor cells, with higher expression levels indicating more aggressive tumors. In a closely related embodiment, one can evaluate the integrity PC-LECTIN nucleotide and amino acid sequences in a biological sample in order to identify perturbations in the structure of these molecules such as insertions, deletions, substitutions and the like, with the presence of one or more perturbations indicating more aggressive tumors.

Yet another related aspect of the invention is directed to methods for observing the progression of a malignancy in an individual over time. In one embodiment, methods for observing the progression of a malignancy in an individual over time comprise determining the level of PC-LECTIN mRNA or PC-LECTIN protein expressed by cells in a sample of the tumor, comparing the level so determined to the level of PC-LECTIN mRNA or PC-LECTIN protein expressed in an equivalent tissue sample taken from the same individual at a different time, wherein the degree of PC-LECTIN mRNA or PC-LECTIN protein expression in the tumor sample over time provides information on the progression of the cancer. In a specific embodiment, the progression of a cancer is evaluated by determining the extent to which PC-LECTIN expression in the tumor cells alters over time, with higher expression levels indicating a progression of the cancer. In a closely related embodiment, one can evaluate the integrity PC-LECTIN nucleotide and amino acid sequences in a biological sample in order to identify perturbations in the structure of these molecules such as insertions, deletions, substitutions and the like, with the presence of one or more perturbations indicating a progression of the cancer.

The above diagnostic approaches may be combined with any one of a wide variety of prognostic and diagnostic protocols known in the art. For example, another embodiment of the invention disclosed herein is directed to methods for observing a coincidence between the expression of PC-LECTIN gene and PC-LECTIN gene products (or perturbations in PC-LECTIN gene and PC-LECTIN gene products) and a factor that is associated with malignancy as a means of diagnosing and prognosticating the status of a tissue sample. In this context, a wide variety of factors associated with malignancy may be utilized such as the expression of genes otherwise associated with malignancy (including PSA, PSCA and PSM expression) as well as gross cytological observations (see e.g. Bocking et al., 1984, Anal. Quant. Cytol. 6(2):74–88; Eptsein, 1995, Hum. Pathol. 1995 Feb;26(2):223–9; Thorson et al., 1998, Mod. Pathol. 11(6):543–51; Baisden et al., 1999, Am. J. Surg. Pathol. 23(8):918–24). Methods for observing a coincidence between the expression of PC-LECTIN gene and PC-LECTIN gene products (or perturbations in PC-LECTIN gene and PC-LECTIN gene products) and an additional factor that is associated with malignancy are useful, for example, because the presence of a set or constellation of specific factors that coincide provides information crucial for diagnosing and prognosticating the status of a tissue sample.

In a typical embodiment, methods for observing a coincidence between the expression of PC-LECTIN gene and PC-LECTIN gene products (or perturbations in PC-LECTIN gene and PC-LECTIN gene products) and a factor that is associated with malignancy entails detecting the overexpression of PC-LECTIN mRNA or protein in a tissue sample, detecting the overexpression of PSA mRNA or protein in a tissue sample, and observing a coincidence of PC-LECTIN mRNA or protein and PSA mRNA or protein overexpression. In a specific embodiment, the expression of PC-LECTIN and PSA mRNA in prostate tissue is examined. In a preferred embodiment, the coincidence of PC-LECTIN and PSA mRNA overexpression in the sample provides an indication of prostate cancer, prostate cancer susceptibility or the emergence or existence of a prostate tumor.

Methods for detecting and quantifying the expression of PC-LECTIN mRNA or protein are described herein and use standard nucleic acid and protein detection and quantification technologies well known in the art. Standard methods for the detection and quantification of PC-LECTIN mRNA include in situ hybridization using labeled PC-LECTIN riboprobes, northern blot and related techniques using PC-LECTIN polynucleotide probes, RT-PCR analysis using primers specific for PC-LECTIN, and other amplification type detection methods, such as, for example, branched DNA, SISBA, TMA and the like. In a specific embodiment, semi-quantitative RT-PCR may be used to detect and quantify PC-LECTIN mRNA expression as described in the Examples that follow. Any number of primers capable of amplifying PC-LECTIN may be used for this purpose, including but not limited to the various primer sets specifically described herein. Standard methods for the detection and quantification of protein may be used for this purpose. In a specific embodiment, polyclonal or monoclonal antibodies specifically reactive with the wild-type PC-LECTIN protein may be used in an immunohistochemical assay of biopsied tissue.

Identifying Molecules that Interact with PC-LECTIN

The PC-LECTIN protein sequences disclosed herein allow the skilled artisan to identify molecules that interact with them via any one of a variety of art accepted protocols. For example one can utilize one of the variety of so-called interaction trap systems (also referred to as the "two-hybrid assay"). In such systems, molecules that interact reconstitute a transcription factor and direct expression of a reporter gene, the expression of which is then assayed. Typical systems identify protein-protein interactions in vivo through reconstitution of a eukaryotic transcriptional activator and are disclosed for example in U.S. Pat. Nos. 5,955,280, 5,925,523, 5,846,722 and 6,004,746.

Alternatively one can identify molecules that interact with PC-LECTIN protein sequences by screening peptide libraries. In such methods, peptides that bind to selected receptor molecules such as PC-LECTIN are identified by screening libraries that encode a random or controlled collection of amino acids. Peptides encoded by the libraries are expressed as fusion proteins of bacteriophage coat proteins, and bacteriophage particles are then screened against the receptors of interest. Peptides having a wide variety of uses, such as therapeutic or diagnostic reagents, may thus be identified without any prior information on the structure of the expected ligand or receptor molecule. Typical peptide libraries and screening methods that can be used to identify molecules that interact with. PC-LECTIN protein sequences are disclosed for example in U.S. Pat. Nos. 5,723,286 and 5,733,731.

Alternatively, cell lines expressing PC-LECTIN can be used to identify protein-protein interactions mediated by PC-LECTIN. This possibility can be examined using immunoprecipitation techniques as shown by others (Hamilton B J, et al. Biochem. Biophys. Res. Commun. 1999, 261:646–51). Typically PC-LECTIN protein can be immunoprecipitated from PC-LECTIN expressing prostate cancer cell lines using anti-PC-LECTIN antibodies. Alternatively, antibodies against His-tag can be used in a cell line engineered to express PC-LECTIN (vectors mentioned above). The immunoprecipitated complex can be examined for protein association by procedures such as western blotting, $^{35}$S-methionine labeling of proteins, protein microsequencing, silver staining and two dimensional gel electrophoresis.

Related embodiments of such screening assays include methods for identifying small molecules that interact with PC-LECTIN. For example, small molecules can be identified that interfere with lectin binding to carbohydrate moieties on other moleucles, such as glycoproteins. Typical methods are discussed for example in U.S. Pat. No. 5,928,868 and include methods for forming hybrid ligands in which at least one ligand is a small molecule. In an illustrative embodiment, the hybrid ligand is introduced into cells that in turn contain a first and a second expression vector. Each expression vector includes DNA for expressing a hybrid protein that encodes a target protein linked to a coding sequence for a transcriptional module. The cells further contains a reporter gene, the expression of which is conditioned on the proximity of the first and second hybrid proteins to each other, an event that occurs only if the hybrid ligand binds to target sites on both hybrid proteins. Those cells that express the reporter gene are selected and the unknown small molecule or the unknown hybrid protein is identified.

A typical embodiment of this invention consists of a method of screening for a molecule that interacts with a PC-LECTIN amino acid sequence shown in FIG. 1A–D (SEQ ID NO: 2), comprising the steps of contacting a population of molecules with the PC-LECTIN amino acid sequence, allowing the population of molecules and the PC-LECTIN amino acid sequence to interact under conditions that facilitate an interaction, determining the presence of a molecule that interacts with the PC-LECTIN amino acid sequence and then separating molecules that do not interact with the PC-LECTIN amino acid sequence from molecules that do interact with the PC-LECTIN amino acid sequence. In a specific embodiment, the method further includes purifying a molecule that interacts with the PC-LECTIN amino acid sequence. In a preferred embodiment, the PC-LECTIN amino acid sequence is contacted with a library of peptides.

Therapeutic Methods and Compositions

The identification of PC-LECTIN as a prostate cancer protein, opens a number of therapeutic approaches to the treatment of prostate cancers. As discussed above, PC-LECTIN binds sugar moieties and may be involved in invasion, adhesion or migration. In addition, PC-LECTIN presents epitopes at the cell surface that can be targeted for therapy.

The expression profile of PC-LECTIN is reminiscent of the MAGEs, PSA and PMSA, which are tissue-specific genes that are up-regulated in melanomas and other cancers (Van den Eynde and Boon, Int J Clin Lab Res. 27:81–86, 1997). Due to their tissue-specific expression and high expression levels in cancer, these molecules are currently being investigated as targets for cancer vaccines (Durrant, Anticancer Drugs 8:727–733, 1997; Reynolds et al., Int J Cancer 72:972–976, 1997). The expression pattern of PC-LECTIN provides evidence that it is likewise an ideal target for a cancer vaccine approach to prostate cancer, as its expression is not detected in most normal tissues. Its structural features as a potential calcium transporter also provides evidence that PC-LECTIN may be a small molecule target, as well as a target for antibody-based therapeutic strategies. The therapeutic strategy can be designed to inhibit the calcium transporter function of the molecule or to target the PC-LECTIN molecule itself.

Accordingly, therapeutic approaches targeting extracellular portions of PC-LECTIN, or aimed at inhibiting the activity of the PC-LECTIN protein, are expected to be useful for patients suffering from prostate cancer and other cancers expressing PC-LECTIN. The therapeutic approaches aimed at inhibiting the activity of the PC-LECTIN protein generally fall into two classes. One class comprises various methods for inhibiting the binding or association of the PC-LECTIN protein with its binding partner or with other proteins. Another class comprises a variety of methods for inhibiting the transcription of the PC-LECTIN gene or translation of PC-LECTIN mRNA.

PC-LECTIN as a Cell Surface Target for Antibody-Based Therapy

The structural features of PC-LECTIN indicate that this molecule is likely a cell surface antigen, providing an attractive target for antibody-based therapeutic strategies. Because PC-LECTIN is expressed on cancer cells and not on most normal cells, systemic administration of PC-LECTIN-immunoreactive compositions would be expected to exhibit excellent sensitivity without toxic, non-specific and/or non-target effects caused by binding of the immunotherapeutic molecule to non-target organs and tissues. Antibodies specifically reactive with extracellular domains of PC-LECTIN can be useful to treat PC-LECTIN-expressing cancers systemically, either as conjugates with a toxin or therapeutic agent, or as naked antibodies capable of inhibiting cell proliferation or function.

PC-LECTIN antibodies can be introduced into a patient such that the antibody binds to PC-LECTIN on the cancer cells and mediates the destruction of the cells and the tumor and/or inhibits the growth of the cells or the tumor. Mechanisms by which such antibodies exert a therapeutic effect may include complement-mediated cytolysis, antibody-dependent cellular cytotoxicity, modulating the physiological function of PC-LECTIN, inhibiting ligand binding or signal transduction pathways, modulating tumor cell differentiation, altering tumor angiogenesis factor profiles, and/or by inducing apoptosis. PC-LECTIN antibodies can be conjugated to toxic or therapeutic agents and used to deliver the toxic or therapeutic agent directly to PC-LECTIN-bearing tumor cells. Examples of toxic agents include, but are not limited to, calchemicin, maytansinoids, radioisotopes such as $^{131}$I, ytrium, and bismuth.

Cancer immunotherapy using anti-PC-LECTIN antibodies may follow the teachings generated from various approaches that have been successfully employed in the treatment of other types of cancer, including but not limited to colon cancer (Arlen et al., 1998, Crit. Rev. Immunol. 18:133–138), multiple myeloma (Ozaki et al., 1997, Blood 90:3179–3186; Tsunenari et al., 1997, Blood 90:2437–2444), gastric cancer (Kasprzyk et al., 1992, Cancer Res. 52:2771–2776), B-cell lymphoma (Funakoshi et al., 1996, J. Immunother. Emphasis Tumor Immunol. 19:93–101), leukemia (Zhong et al., 1996, Leuk. Res. 20:581–589), colorectal cancer (Moun et al., 1994, Cancer Res. 54:6160–6166); Velders et al., 1995, Cancer Res. 55:4398–4403), and breast cancer (Shepard et al., 1991, J. Clin. Immunol. 11:117–127). Some therapeutic approaches involve conjugation of naked antibody to a toxin, such as the conjugation of 131I to anti-CD20 antibodies (e.g., Rituxan™, IDEC Pharmaceuticals Corp.), while others involve co-administration of antibodies and other therapeutic agents, such as Herceptin™ (trastuzumab) with paclitaxel (Genentech, Inc.). For treatment of prostate cancer, for example, PC-LECTIN antibodies can be administered in conjunction with radiation, chemotherapy or hormone ablation.

Although PC-LECTIN antibody therapy may be useful for all stages of cancer, antibody therapy may be particularly appropriate in advanced or metastatic cancers. Treatment with the antibody therapy of the invention may be indicated for patients who have received previously one or more chemotherapy, while combining the antibody therapy of the invention with a chemotherapeutic or radiation regimen may be preferred for patients who have not received chemotherapeutic treatment. Additionally, antibody therapy may enable the use of reduced dosages of concomitant chemotherapy, particularly for patients who do not tolerate the toxicity of the chemotherapeutic agent very well.

It may be desirable for some cancer patients to be evaluated for the presence and level of PC-LECTIN expression, preferably using immunohistochemical assessments of tumor tissue, quantitative PC-LECTIN imaging, or other techniques capable of reliably indicating the presence and degree of PC-LECTIN expression. Immunohistochemical analysis of tumor biopsies or surgical specimens may be preferred for this purpose. Methods for immunohistochemical analysis of tumor tissues are well known in the art.

Anti-PC-LECTIN monoclonal antibodies useful in treating prostate and other cancers include those that are capable of initiating a potent immune response against the tumor and those that are capable of direct cytotoxicity. In this regard, anti-PC-LECTIN monoclonal antibodies (mAbs) may elicit tumor cell lysis by either complement-mediated or antibody-dependent cell cytotoxicity (ADCC) mechanisms, both of which require an intact Fc portion of the immunoglobulin molecule for interaction with effector cell Fc receptor sites or complement proteins. In addition, anti-PC-LECTIN mAbs that exert a direct biological effect on tumor growth are useful in the practice of the invention. Potential mechanisms by which such directly cytotoxic mAbs may act include inhibition of cell growth, modulation of cellular differentiation, modulation of tumor angiogenesis factor profiles, and the induction of apoptosis. The mechanism by which a particular anti-PC-LECTIN mAb exerts an anti-tumor effect may be evaluated using any number of in vitro assays designed to determine ADCC, ADMMC, complement-mediated cell lysis, and so forth, as is generally known in the art.

The use of murine or other non-human monoclonal antibodies, or human/mouse chimeric mAbs may induce moderate to strong immune responses in some patients. In some cases, this will result in clearance of the antibody from circulation and reduced efficacy. In the most severe cases, such an immune response may lead to the extensive formation of immune complexes which, potentially, can cause renal failure. Accordingly, preferred monoclonal antibodies used in the practice of the therapeutic methods of the invention are those that are either fully human or humanized and that bind specifically to the target PC-LECTIN antigen with high affinity but exhibit low or no antigenicity in the patient.

Therapeutic methods of the invention contemplate the administration of single anti-PC-LECTIN mAbs as well as combinations, or cocktails, of different mAbs. Such mAb cocktails may have certain advantages inasmuch as they contain mAbs that target different epitopes, exploit different effector mechanisms or combine directly cytotoxic mAbs with mabs that rely on immune effector functionality. Such mAbs in combination may exhibit synergistic therapeutic effects. In addition, the administration of anti-PC-LECTIN mAbs may be combined with other therapeutic agents, including but not limited to various chemotherapeutic agents, androgen-blockers, and immune modulators (e.g., IL-2, GM-CSF). The anti-PC-LECTIN mAbs may be administered in their "naked" or unconjugated form, or may have therapeutic agents conjugated to them.

The anti-PC-LECTIN antibody formulations may be administered via any route capable of delivering the antibodies to the tumor site. Potentially effective routes of administration include, but are not limited to, intravenous, intraperitoneal, intramuscular, intratumor, intradermal, and the like. Treatment will generally involve the repeated administration of the anti-PC-LECTIN antibody preparation via an acceptable route of administration such as intravenous injection (IV), typically at a dose in the range of about 0.1 to about 10 mg/kg body weight. Doses in the range of 10–500 mg mAb per week may be effective and well tolerated.

Based on clinical experience with the Herceptin mAb in the treatment of metastatic breast cancer, an initial loading dose of approximately 4 mg/kg patient body weight IV followed by weekly doses of about 2 mg/kg IV of the anti-PC-LECTIN mAb preparation may represent an acceptable dosing regimen. Preferably, the initial loading dose is administered as a 90 minute or longer infusion. The periodic maintenance dose may be administered as a 30 minute or longer infusion, provided the initial dose was well tolerated. However, as one of skill in the art will understand, various factors will influence the ideal dose regimen in a particular case. Such factors may include, for example, the binding affinity and half life of the Ab or mAbs used, the degree of PC-LECTIN expression in the patient, the extent of circulating shed PC-LECTIN antigen, the desired steady-state antibody concentration level, frequency of treatment, and the influence of chemotherapeutic agents used in combination with the treatment method of the invention.

Optimally, patients should be evaluated for the level of circulating shed PC-LECTIN antigen in serum in order to assist in the determination of the most effective dosing regimen and related factors. Such evaluations may also be used for monitoring purposes throughout therapy, and may be useful to gauge therapeutic success in combination with evaluating other parameters (such as serum PSA levels in prostate cancer therapy).

Inhibition of PC-LECTIN Protein Function

The invention includes various methods and compositions for inhibiting the binding of PC-LECTIN to its binding partner or ligand, or its association with other protein(s) as well as methods for inhibiting PC-LECTIN function.

Inhibition of PC-LECTIN with Intracellular Antibodies

In one approach, recombinant vectors encoding single chain antibodies that specifically bind to PC-LECTIN may be introduced into PC-LECTIN expressing cells via gene transfer technologies, wherein the encoded single chain anti-PC-LECTIN antibody is expressed intracellularly, binds to PC-LECTIN protein, and thereby inhibits its function. Methods for engineering such intracellular single chain antibodies are well known. Such intracellular antibodies, also known as "intrabodies", may be specifically targeted to a particular compartment within the cell, providing control over where the inhibitory activity of the treatment will be focused. This technology has been successfully applied in the art (for review, see Richardson and Marasco, 1995, TIBTECH vol. 13). Intrabodies have been shown to virtually eliminate the expression of otherwise abundant cell surface receptors. See, for example, Richardson et al., 1995, Proc. Natl. Acad. Sci. USA 92: 3137–3141; Beerli et al., 1994, J. Biol. Chem. 289: 23931–23936; Deshane et al., 1994, Gene Ther. 1: 332–337.

Single chain antibodies comprise the variable domains of the heavy and light chain joined by a flexible linker polypeptide, and are expressed as a single polypeptide. Optionally, single chain antibodies may be expressed as a single chain variable region fragment joined to the light chain constant region. Well known intracellular trafficking signals may be engineered into recombinant polynucleotide vectors encoding such single chain antibodies in order to precisely target the expressed intrabody to the desired intracellular compartment. For example, intrabodies targeted to the endoplasmic reticulum (ER) may be engineered to incorporate a leader peptide and, optionally, a C-terminal ER retention signal, such as the KDEL amino acid motif. Intrabodies intended to exert activity in the nucleus may be engineered to include a nuclear localization signal. Lipid moieties may be joined to intrabodies in order to tether the intrabody to the cytosolic side of the plasma membrane. Intrabodies may also be targeted to exert function in the cytosol. For example, cytosolic intrabodies may be used to sequester factors within the cytosol, thereby preventing them from being transported to their natural cellular destination.

In one embodiment, PC-LECTIN intrabodies are designed to bind specifically to a particular PC-LECTIN domain. For example, cytosolic intrabodies that specifically bind to the PC-LECTIN protein may be used to prevent PC-LECTIN from gaining access to the nucleus, thereby preventing it from exerting any biological activity within the nucleus (e.g., preventing PC-LECTIN from forming transcription complexes with other factors).

In order to specifically direct the expression of such intrabodies to particular tumor cells, the transcription of the intrabody may be placed under the regulatory control of an appropriate tumor-specific promoter and/or enhancer. In order to target intrabody expression specifically to prostate, for example, the PSA promoter and/or promoter/enhancer may be utilized (See, for example, U.S. Pat. No. 5,919,652).

Inhibition of PC-LECTIN with Recombinant Proteins

In another approach, recombinant molecules that are capable of binding to PC-LECTIN thereby preventing PC-LECTIN from accessing/binding to its binding partner (s) or associating with other protein(s) are used to inhibit PC-LECTIN function. Such recombinant molecules may, for example, contain the reactive part(s) of a PC-LECTIN specific antibody molecule. In a particular embodiment, the PC-LECTIN binding domain of a PC-LECTIN binding partner may be engineered into a dimeric fusion protein comprising two PC-LECTIN ligand binding domains linked to the Fc portion of a human IgG, such as human IgG1. Such IgG portion may contain, for example, the $C_H2$ and $C_H3$ domains and the hinge region, but not the $C_H1$ domain. Such dimeric fusion proteins may be administered in soluble form to patients suffering from a cancer associated with the expression of PC-LECTIN, including but not limited to prostate, breast, bladder, lung, bone, colon, pancreatic, testicular, cervical and ovarian cancers, where the dimeric fusion protein specifically binds to PC-LECTIN thereby blocking PC-LECTIN interaction with a binding partner. Such dimeric fusion proteins may be further combined into multimeric proteins using known antibody linking technologies.

Inhibition of PC-LECTIN Transcription or Translation

Within another class of therapeutic approaches, the invention provides various methods and compositions for inhibiting the transcription of the PC-LECTIN gene. Similarly, the invention also provides methods and compositions for inhibiting the translation of PC-LECTIN mRNA into protein.

In one approach, a method of inhibiting the transcription of the PC-LECTIN gene comprises contacting the PC-LECTIN gene with a PC-LECTIN antisense polynucleotide. In another approach, a method of inhibiting PC-LECTIN mRNA translation comprises contacting the PC-LECTIN mRNA with an antisense polynucleotide. In another approach, a PC-LECTIN specific ribozyme may be used to cleave the PC-LECTIN message, thereby inhibiting translation. Such antisense and ribozyme based methods may also be directed to the regulatory regions of the PC-LECTIN gene, such as the PC-LECTIN promoter and/or enhancer elements. Similarly, proteins capable of inhibiting a PC-LECTIN gene transcription factor may be used to inhibit PC-LECTIN mRNA transcription. The various polynucleotides and compositions useful in the aforementioned methods have been described above. The use of antisense and ribozyme molecules to inhibit transcription and translation is well known in the art.

Other factors that inhibit the transcription of PC-LECTIN through interfering with PC-LECTIN transcriptional activation may also be useful for the treatment of cancers expressing PC-LECTIN. Similarly, factors that are capable of interfering with PC-LECTIN processing may be useful for the treatment of cancers expressing PC-LECTIN. Cancer treatment methods utilizing such factors are also within the scope of the invention.

General Considerations for Therapeutic Strategies

Gene transfer and gene therapy technologies may be used for delivering therapeutic polynucleotide molecules to tumor cells synthesizing PC-LECTIN (i.e., antisense, ribozyme, polynucleotides encoding intrabodies and other PC-LECTIN inhibitory molecules). A number of gene therapy approaches are known in the art. Recombinant vectors encoding PC-LECTIN antisense polynucleotides, ribozymes, factors capable of interfering with PC-LECTIN transcription, and so forth, may be delivered to target tumor cells using such gene therapy approaches.

The above therapeutic approaches may be combined with any one of a wide variety of chemotherapy or radiation therapy regimens. These therapeutic approaches may also enable the use of reduced dosages of chemotherapy and/or less frequent administration, particularly in patients that do not tolerate the toxicity of the chemotherapeutic agent well.

The anti-tumor activity of a particular composition (e.g., antisense, ribozyme, intrabody), or a combination of such compositions, may be evaluated using various in vitro and in vivo assay systems. In vitro assays for evaluating therapeutic potential include cell growth assays, soft agar assays and other assays indicative of tumor promoting activity, binding assays capable of determining the extent to which a therapeutic composition will inhibit the binding of PC-LECTIN to a binding partner, etc.

In vivo, the effect of a PC-LECTIN therapeutic composition may be evaluated in a suitable animal model. For example, xenogenic prostate cancer models wherein human prostate cancer explants or passaged xenograft tissues are introduced into immune compromised animals, such as nude or SCID mice, are appropriate in relation to prostate cancer and have been described (Klein et al., 1997, Nature Medicine 3: 402–408). For example, PCT Patent Application WO98/16628, Sawyers et al., published Apr. 23, 1998, describes various xenograft models of human prostate cancer capable of recapitulating the development of primary tumors, micrometastasis, and the formation of osteoblastic metastases characteristic of late stage disease. Efficacy may be predicted using assays that measure inhibition of tumor formation, tumor regression or metastasis, and the like. See, also, the Examples below.

In vivo assays that qualify the promotion of apoptosis may also be useful in evaluating potential therapeutic compositions. In one embodiment, xenografts from bearing mice treated with the therapeutic composition may be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods may be formulated into pharmaceutical compositions comprising a carrier suitable for the desired delivery method. Suitable carriers include any material that when combined with the therapeutic composition retains the anti-tumor function of the therapeutic composition and is non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences $16^{th}$ Edition, A. Osal., Ed., 1980).

Therapeutic formulations may be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations may be lyophilized and stored as sterile powders, preferably under vacuum, and then reconstituted in bacteriostatic water containing, for example, benzyl alcohol preservative, or in sterile water prior to injection.

Dosages and administration protocols for the treatment of cancers using the foregoing methods will vary with the method and the target cancer and will generally depend on a number of other factors appreciated in the art.

Cancer Vaccines

The invention further provides cancer vaccines comprising a PC-LECTIN protein or fragment thereof, as well as DNA based vaccines. In view of the tumor-restricted expression of PC-LECTIN, PC-LECTIN cancer vaccines are expected to be effective at specifically preventing and/or treating PC-LECTIN expressing cancers without creating non-specific effects on non-target tissues. The use of a tumor antigen in a vaccine for generating humoral and cell-mediated immunity for use in anti-cancer therapy is well known in the art and has been employed in prostate cancer using human PSMA and rodent PAP immunogens (Hodge et al., 1995, Int. J. Cancer 63: 231–237; Fong et al., 1997, J. Immunol. 159: 3113–3117). Such methods can be readily practiced by employing a PC-LECTIN protein, or fragment thereof, or a PC-LECTIN-encoding nucleic acid molecule and recombinant vectors capable of expressing and appropriately presenting the PC-LECTIN immunogen.

For example, viral gene delivery systems may be used to deliver a PC-LECTIN-encoding nucleic acid molecule. Various viral gene delivery systems that can be used in the practice of this aspect of the invention include, but are not limited to, vaccinia, fowlpox, canarypox, adenovirus, influenza, poliovirus, adeno-associated virus, lentivirus, and sindbus virus (Restifo, 1996, Curr. Opin. Immunol. 8: 658–663). Non-viral delivery systems may also be employed by using naked DNA encoding a PC-LECTIN protein or fragment thereof introduced into the patient (e.g., intramuscularly) to induce an anti-tumor response. In one embodiment, the full-length human PC-LECTIN cDNA may be employed.

In one embodiment, a PC-LECTIN cancer vaccine is based on the identification of immunogenic peptides within the PC-LECTIN amino acid sequence shown in FIGS. 1A–D (SEQ ID NO: 2). As discussed further in the examples below, specific portions of PC-LECTIN have been shown to induce T and B cell responses. The extracellular domain of PC-LECTIN (amino acids 22–213 of FIGS. 1A–D; SEQ ID NO: 2) has been used to generate an immune response in mice for the production of monoclonal antibodies; and peptides within this domain, GLWRNGDGQTSGAC (SEQ ID NO: 25), GGPYLYQWNDDRCNM (SEQ ID NO: 26), EARLACESEGGVLL (SEQ ID NO: 27), have been used to generate an immune response in rabbits for the production of polyclonal antibodies. Thus, these specific portions of PC-LECTIN, and polynucleotides encoding these portions, may be selected for the production of a cancer vaccine.

In another embodiment, PC-LECTIN nucleic acid molecules encoding specific cytotoxic T lymphocyte (CTL) epitopes may be employed. CTL epitopes can be determined using specific algorithms (e.g., Epimer, Brown University) to identify peptides within a PC-LECTIN protein that are capable of optimally binding to specified HLA alleles. One suitable algorithm is the HLA Peptide Motif Search algorithm available at the Bioinformatics and Molecular Analysis Section (BIMAS) web site (http://bimas.dcrt.nih.gov/). This algorithm is based on binding of specific peptide sequences in the groove of HLA Class I molecules and specifically HLA-A2 (Falk et al., 1991, Nature 351:290–6; Hunt et al., 1992, Science 255:1261–3; Parker et al., 1992, J. Immunol. 149:3580–7; Parker et al., 1994, J. Immunol. 152:163–75). The HLA Peptide Motif Search algorithm allows location and ranking of 8-mer, 9-mer, and 10-mer peptides from a complete protein sequence for predicted binding to HLA-A2 as well as other Class I molecules. Most HLA-A2 binding peptides are 9-mers, favorably containing a leucine at position 2 and a valine or leucine at position 9 (Parker et al., 1992, J. Immunol. 149:3580–7).

As discussed in the Examples below, predicted binding peptides for PC-LECTIN include WIGFTYKTA, ATGEHQAFT, FGNCVELQA, NCVELQASA, and DNHGFGNCV (SEQ ID NO: 6–10, respectively). Actual binding of peptides to HLA-A2 can be evaluated by stabilization of HLA-A2 expression on the antigen processing defective cell line T2 (Xue et al., 1997, Prostate 30:73–8; Peshwa et al., 1998, Prostate 36:129–38). Immunogenicity of specific peptides can be evaluated in vitro by stimulation of CD8+ CTL in the presence of dendritic cells (Xue et al.; Peshwa et al., supra).

Various ex vivo strategies may also be employed. One approach involves the use of dendritic cells to present PC-LECTIN antigen to a patient's immune system. Dendritic cells express MHC class I and II, B7 co-stimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28: 65–69; Murphy et al., 1996, Prostate 29: 371–380). Dendritic cells can be used to present PC-LECTIN peptides to T cells in the context of MHC class I and II molecules. In one embodiment, autologous dendritic cells are pulsed with PC-LECTIN peptides capable of binding to MHC molecules. In another embodiment, dendritic cells are pulsed with the complete PC-LECTIN protein. Yet another embodiment involves engineering the overexpression of the PC-LECTIN gene in dendritic cells using various implementing vectors known in the art, such as adenovirus (Arthur et al., 1997, Cancer Gene Ther. 4: 17–25), retrovirus (Henderson et al., 1996, Cancer Res. 56: 3763–3770), lentivirus, adeno-associated virus, DNA transfection (Ribas et al., 1997, Cancer Res. 57: 2865–2869), and tumor-derived RNA transfection (Ashley et al., 1997, J. Exp. Med. 186: 1177–1182). Cells expressing PC-LECTIN may also be engineered to express immune modulators, such as GM-CSF, and used as immunizing agents.

Anti-idiotypic anti-PC-LECTIN antibodies can also be used in anti-cancer therapy as a vaccine for inducing an immune response to cells expressing a PC-LECTIN protein. Specifically, the generation of anti-idiotypic antibodies is well known in the art and can readily be adapted to generate anti-idiotypic anti-PC-LECTIN antibodies that mimic an epitope on a PC-LECTIN protein (see, for example, Wagner et al., 1997, Hybridoma 16: 33–40; Foon et al., 1995, J Clin Invest 96: 334–342; Herlyn et al., 1996, Cancer Immunol Immunother 43: 65–76). Such an anti-idiotypic antibody can be used in cancer vaccine strategies.

Genetic immunization methods may be employed to generate prophylactic or therapeutic humoral and cellular immune responses directed against cancer cells expressing PC-LECTIN. Constructs comprising DNA encoding a PC-LECTIN protein/immunogen and appropriate regulatory sequences may be injected directly into muscle or skin of an individual, such that the cells of the muscle or skin take-up the construct and express the encoded PC-LECTIN protein/immunogen. Expression of the PC-LECTIN protein immunogen results in the generation of prophylactic or therapeutic humoral and cellular immunity against prostate, breast, bladder, lung, bone, colon, pancreatic, testicular, cervical and ovarian cancers. Various prophylactic and therapeutic genetic immunization techniques known in the art may be used (for review, see information and references published at Internet address www.genweb.com).

Kits

For use in the diagnostic and therapeutic applications described or suggested above, kits are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe that is or can be detectably labeled. Such probe may be an antibody or polynucleotide specific for a PC-LECTIN protein or a PC-LECTIN gene or message, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

The kit of the invention will typically comprise the container described above and one or more other containers comprising materials desirable from a commercial and user standpoint, including buffers, diluents, filters, needles, syringes, and package inserts with instructions for use. A label may be present on the on the container to indicate that the composition is used for a specific therapy or non-therapeutic application, and may also indicate directions for either in vivo or in vitro use, such as those described above.

The PC-LECTIN cDNA was deposited under the terms of the Budapest Treaty on Mar. 10, 1999, with the American Type Culture Collection (ATCC; 10801 University Blvd., Manassas, Va. 20110-2209 USA) as plasmid p58P1D12-2, and has been assigned Accession No. 207152.

EXAMPLES

Various aspects of the invention are further described and illustrated by way of the several examples that follow, none of which are intended to limit the scope of the invention.

Example 1

SSH-Generated Isolation of cDNA Fragment of the PC-LECTIN Gene

Materials and Methods

LAPC Xenografts

LAPC xenografts were obtained from Dr. Charles Sawyers (UCLA) and generated as described (Klein et al, 1997, Nature Med. 3: 402–408; Craft et al., 1999, Cancer Res. 59: 5030–5036). Androgen dependent and independent LAPC-4 xenografts (LAPC-4 AD and AI, respectively) and LAPC-9 xenografts (LAPC-9 AD and AI, respectively) were grown in intact male SCID mice or in castrated males, respectively, and were passaged as small tissue chunks in recipient males. LAPC-4 AI xenografts were derived from LAPC-4 AD tumors and LAPC-9 AI xenografts were derived from LAPC-9 AD tumors. To generate the AI xenografts, male mice bearing LAPC AD tumors were castrated and maintained for 2–3 months. After the LAPC tumors re-grew, the tumors were harvested and passaged in castrated males or in female SCID mice.

Cell Lines

Human cell lines (e.g., HeLa) were obtained from the ATCC and were maintained in DMEM with 10% fetal calf serum.

RNA Isolation

Tumor tissue and cell lines were homogenized in Trizol reagent (Life Technologies, Gibco BRL) using 10 ml/g tissue or 10 ml/$10^8$ cells to isolate total RNA. Poly A RNA was purified from total RNA using Qiagen's Oligotex mRNA Mini and Midi kits. Total and mRNA were quantified by spectrophotometric analysis (O.D. 260/280 nm) and analyzed by gel electrophoresis.

Oligonucleotides

The following HPLC purified oligonucleotides were used.

DPNCDN (cDNA synthesis primer) (SEQ ID NO: 11):
  5'TTTTGATCAAGCTT$_{30}$3'

Adaptor 1 (SEQ ID NO: 12 and 13, respectively):
  5'CTAATACGACTCACTATAGGGCTC-
  GAGCGGCCGCCCGGGCAG3'
  3'GGCCCGTCCTAG5'

Adaptor 2 (SEQ ID NO: 14 and 15, respectively):
  5'GTAATACGACTCACTATAGGGCAGCGTG-
  GTCGCGGCCGAG3'
  3'CGGCTCCTAG5'

PCR primer 1 (SEQ ID NO: 16):
  5'CTAATACGACTCACTATAGGGC3'

Nested primer (NP)1 (SEQ ID NO: 17):
  5TCGAGCGGCCGCCCGGGCAGGA3'

Nested primer (NP)2 (SEQ ID NO: 18):
  5'AGCGTGGTCGCGGCCGAGGA3'

Suppression Subtractive Hybridization

Suppression subtractive hybridization (SSH) was used to identify cDNAs corresponding to genes that may be up-regulated in androgen dependent prostate cancer compared to androgen independent cancer.

Double stranded cDNAs corresponding to the LAPC-9 AD xenograft (tester) and the LAPC-9 AI tissue (driver) were synthesized from 2 μg of poly(A)' RNA isolated from the xenografts, as described above, using CLONTECH's PCR-Select cDNA Subtraction Kit and 1 ng of oligonucleotide DPNCDN as primer. First and second-strand synthesis were carried out as described in the Kit's user manual protocol (CLONTECH Protocol No. PT1117-1, Catalog No. K1804-1). The resulting cDNA was digested with Dpn II for 3 hrs. at 37° C. Digested cDNA was extracted with phenol/chloroform (1:1) and ethanol precipitated.

Driver cDNA (LAPC-9AI) was generated by combining in a 1 to 1 ratio Dpn II digested LAPC-9AI cDNA with a mix of digested cDNAs from BPH tissue and human cell lines HeLa, 293, A431, Colo 205 and mouse liver, in order to ensure that murine genes were subtracted from the tester cDNA (LAPC-9 AD).

Tester cDNA (LAPC-9 AD) was generated by diluting 1 μl of Dpn II digested LAPC-9 AD cDNA (400 ng) in 5 μl of water. The diluted cDNA (2 μl, 160 ng) was then ligated to 2 μl of adaptor 1 and adaptor 2 (10 μM), in separate ligation reactions, in a total volume of 10 μl at 16° C. overnight, using 400 u of T4 DNA ligase (CLONTECH). Ligation was terminated with 1 μl of 0.2 M EDTA and heating at 72° C. for 5 min.

The first hybridization was performed by adding 1.5 μl (600 ng) of driver cDNA to each of two tubes containing 1.5 μl (20 ng) adaptor 1- and adaptor 2-ligated tester cDNA. In a final volume of 4 μl, the samples were overlayed with mineral oil, denatured in an MJ Research thermal cycler at 98° C. for 1.5 minutes, and then were allowed to hybridize for 8 hrs at 68° C. The two hybridizations were then mixed together with an additional 1 μl of fresh denatured driver cDNA and were allowed to hybridize overnight at 68° C. The second hybridization was then diluted in 200 μl of 20 mM Hepes, pH 8.3, 50 mM NaCl, 0.2 mM EDTA, heated at 70° C. for 7 min. and stored at –20° C.

PCR Amplification, Cloning and Sequencing of Gene Fragments Generated from SSH

To amplify gene fragments resulting from SSH reactions, two PCR amplifications were performed. In the primary PCR reaction 1 μl of the diluted final hybridization mix was added to 1 μl of PCR primer 1 (10 μM), 0.5 μl dNTP mix (10 μM), 2.5 μl 10× reaction buffer (CLONTECH) and 0.5 μl 50× Advantage cDNA polymerase Mix (CLONTECH) in a final volume of 25 μl. PCR 1 was conducted using the following conditions: 75° C. for 5 min., 94° C. for 25 sec., then 27 cycles of 94° C. for 10 sec, 66° C. for 30 sec, 72° C. for 1.5 min. Five separate primary PCR reactions were performed for each experiment. The products were pooled and diluted 1:10 with water. For the secondary PCR reaction, 1 μl from the pooled and diluted primary PCR reaction was added to the same reaction mix as used for PCR 1, except that primers NP1 and NP2 (10 μM) were used instead of PCR primer 1. PCR 2 was performed using 10–12 cycles of 94° C. for 10 sec, 68° C. for 30 sec, 72° C. for 1.5 minutes. The PCR products were analyzed using 2% agarose gel electrophoresis.

The PCR products were inserted into pCR2.1 using the T/A vector cloning kit (Invitrogen). Transformed *E. coli* were subjected to blue/white and ampicillin selection. White colonies were picked and arrayed into 96 well plates and were grown in liquid! culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analysis

First strand cDNAs were generated from 1 μg of mRNA with oligo (dT)12–18 priming using the Gibco-BRL Superscript Preamplification system. The manufacturers protocol was used and included an incubation for 50 min at 42° C. with reverse transcriptase followed by RNAse H treatment at 37° C. for 20 min. After completing the reaction, the volume was increased to 200 µl with water prior to normalization. First strand cDNAs from 16 different normal human tissues were obtained from Clontech.

Normalization of the first strand cDNAs from multiple tissues was performed by using the primers 5'atatcgccgcgctcgtcgtcgacaa3' (SEQ ID NO: 19) and 5'agccacacgcagctcattgtagaagg 3' (SEQ ID NO: 20) to amplify β-actin. First strand cDNA (5 µl) was amplified in a total volume of 50 µl containing 0.4 µM primers, 0.2 µM each dNTPs, 1×PCR buffer (Clontech, 10 mM Tris-HCL, 1.5 mM MgCl$_2$, 50 mM KCl, pH8.3) and 1× Klentaq DNA polymerase (Clontech). Five µl of the PCR reaction was removed at 18, 20, and 22 cycles and used for a0arose gel electrophoresis. PCR was performed using an MJ Research thermal cycler under the following conditions: initial denaturation was at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 bp β-actin bands from multiple tissues were compared by visual inspection. Dilution factors for the first strand cDNAs were calculated to result in equal β-actin band intensities in all tissues after 22 cycles of PCR. Three rounds of normalization were required to achieve equal band intensities in all tissues after 22 cycles of PCR.

To determine expression levels of the PC-LECTIN gene, 5 µl of normalized first strand cDNA was analyzed by PCR using 25, 30, and 35 cycles of amplification using the following primer pairs, which were designed with the assistance of (MIT; for details, see, www.genome.wi.mit.edu) (SEQ ID NO: 21 and 22, respectively):

58P1D12.1 5' CCTGCTTCAGTAACAACCACATTCT 3'

58P1D12.2 5' CTTTACCAGTGGAATGATGACAGG 3'

Semi quantitative expression analysis was achieved by comparing the PCR products at cycle numbers that give light band intensities.

Results

Several SSH experiments were conduced as described in the Materials and Methods, supra, and led to the isolation of numerous candidate gene fragment clones. All candidate clones were sequenced and subjected to homology analysis against all sequences in the major public gene and EST databases in order to provide information on the identity of the corresponding gene and to help guide the derision to analyze a particular gene for differential expression. In general, gene fragments which had no homology to any known sequence in any of the searched databases, and thus considered to represent novel genes, as well as gene fragments showing homology to previously sequenced expressed sequence tags (ESTs), were subjected to differential expression analysis by RT-PCR and/or northern analysis.

One of the cDNA clones, designated 58P1D12, was 427 bp in length and showed weak homology to an EST derived from pig muscle as well as significant homology to hamster layilin, a cell surface molecule with homology to C-type lectins. The SSH fragment contained an ORF of 129 amino acids, which showed significant homology to layilin. The ORF of this fragment corresponds to the central region of layilin and contains the transmembrane domain. The full length cDNA encoding the 58P1D12 gene was subsequently isolated using this cDNA and structurally analyzed (Example 2, below) and re-named PC-LECTIN.

Figure 4B:
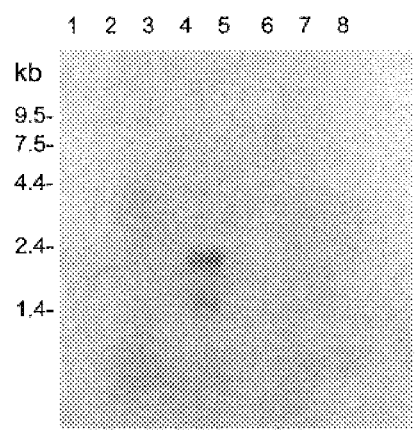
FIG. 4B. Northern blot analyses of PC-LECTIN expression in various normal human tissues, showing testis-specific expression of PC-LECTIN in normal tissues. Lane 1 is spleen; lane 2 is thymus; lane 3 is prostate; lane 4 is testis; lane 5 is ovary; lane 6 is small intestine; lane 7 is colon; and lane 8 is leukocytes.
Figure 4C:
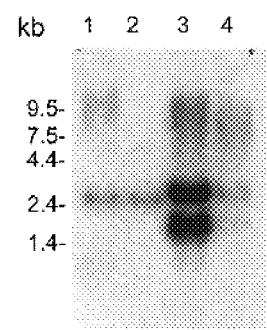
FIG. 4C. Northern blot analyses of PC-LECTIN expression in prostate cancer xenografts, showing high level expression in all prostate cancer xenografts, with extremely high level expression in the advanced metastatic prostate tumor xenograft LAPC-9 AD. Lane 1 is LAPC-4 AD; lane 2 is LAPC-4 AI; lane 3 is LAPC-9 AD; and lane 4 is LAPC-9 AI.

Differential expression analysis by RT-PCR using primers derived from the PC-LECTIN SSH clone showed that the 58P1D12/PC-LECTIN gene is essentially expressed in normal testis and in the prostate tumor xenografts examined (FIG. 3). At higher cycles of amplification (i.e., 30+), lower level expression was detected in prostate, spleen and placenta. Northern blot analysis using the full length PC-LECTIN cDNA as a probe (see Example 3, below) showed expression of 1.8 and 3.0 kb transcripts only in normal testis and in LAPC9 AD RNA (FIG. 4). Lower expression levels are detected in LAPC-4AD, LAPC-4AI and LAPC-9 AI.

Example 2

Isolation of Full Length PC-LECTIN Encoding cDNA

The 427 bp 58P1D12/PC-LECTIN gene fragment (Example 1) was used to isolate 30 additional cDNAs encoding the PC-LECTIN gene. A full length cDNA clone for PC-LECTIN was isolated from an LAPC-9 AD library. The cDNA (clone 2) is 25510 bp in length and encodes a 273 amino acid ORF. Analysis of the ORF identifies an N-terminal signal sequence and a transmembrane domain that indicate PC-LECTIN to be a type la transmembrane protein with the N-terminus on the outside and a cytoplasmic C-terminus. The full length PC-LECTIN cDNA has been deposited with the American Type Culture Collection ("ATCC") (Mannassas, Va.) as plasmid p58P1D12-2 on Mar. 10, 1999 as ATCC Accession Number 207152. The PC-LECTIN cDNA clone therein can be excised therefrom using EcoRIIXbaI double digest (EcoRI at the 5' end, XbaI at the 3' end).

Amino acid alignment of the PC-LECTIN sequence with hamster layilin indicates a relationship to layilin (FIG. 2A). However, PC-LECTIN does not exhibit the talin association domain, suggesting that PC-LECTIN does not interact with the cytoskeleton in the same manner as layilin. Other structural differences are also apparent (FIG. 2A). Alignment of the 2550 bp PC-LECTIN cDNA with the 1747 bp cDNA of hamster layilin cDNA shows homology over a 591 bp region (FIG. 2B). The rest of the PC-LECTIN region is significantly different from layilin, which is reflected in the differences in the amino acid sequence of the C-terminal half of the extracellular domain and the entire cytoplasmic domain. This suggests that while PC-LECTIN and layilin are related and probably constitute a sub-family of lectins, PC-LECTIN is unlikely to be the human form of layilin.

Example 3

PC-LECTIN Gene Expression Analysis

Initial analysis of PC-LECTIN mRNA expression in normal human tissues was conducted by northern blotting two multiple tissue blots obtained from Clontech (Palo Alto, Calif.), comprising a total of 16 different normal human tissues using labeled PC-LECTIN cDNA as a probe. RNA samples were quantitatively normalized with a β-actin probe. The results are shown in FIG. 4 (Panels A and B). Expression was only detected in normal testis. These northern blots showed two transcripts of approximately 1.8 kb and 3.0 kb.

Figure 14:
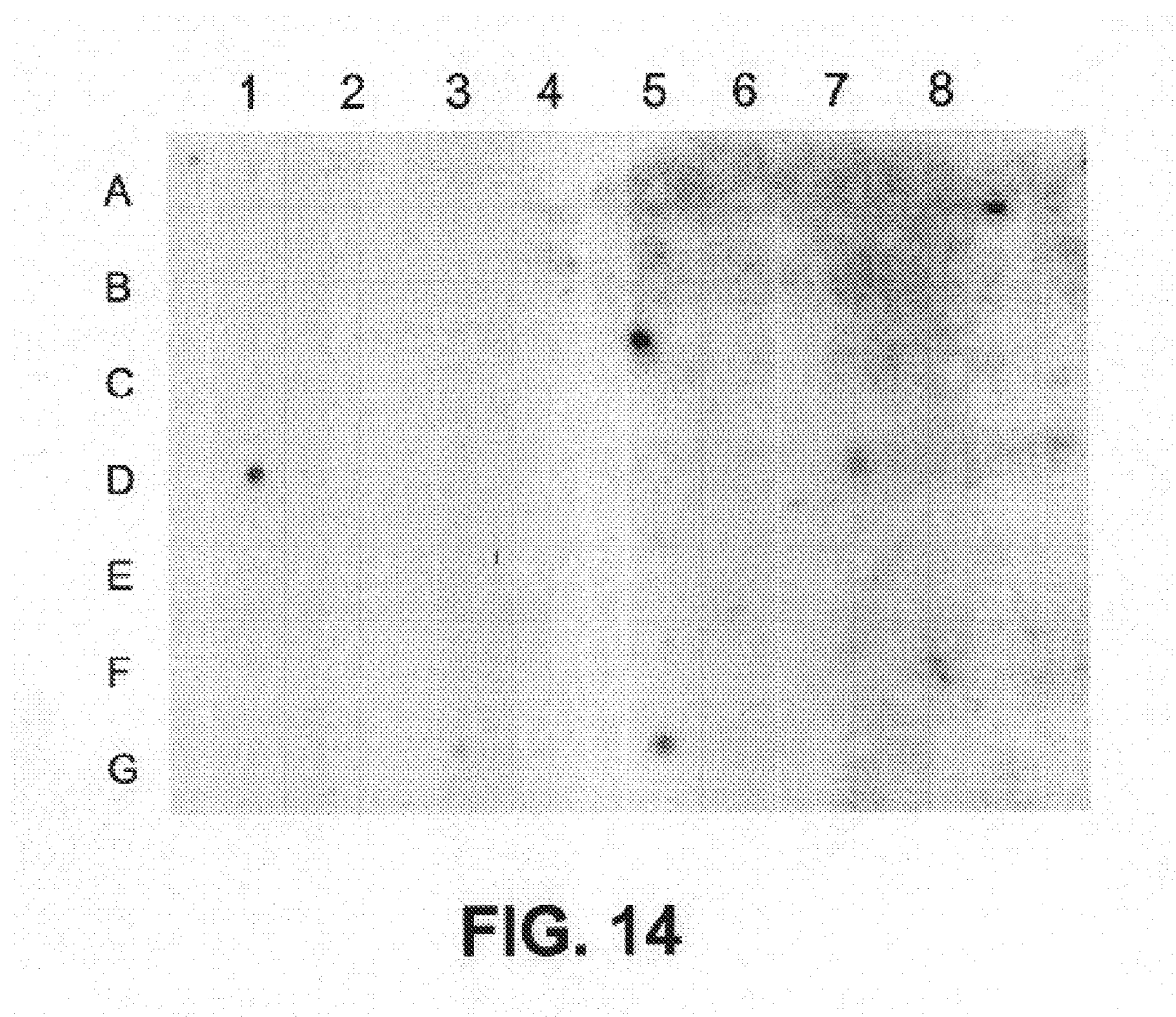
FIG. 14. Expression of PC-LECTIN analyzed using a multi-tissue RNA dot blot (50 samples). The results show significant expression of 58P1D12 only in testis. Lower expression was also detected in salivary gland, fetal kidney and fetal spleen. The blot also shows extraneous signals in other areas, which are likely to be non-specific since they fall in between the rows and columns of the specific signals. Positions represent the following tissues: A1 brain; A2 amygdala; A3 caudate nucleus; A4 cerebellum; A5 cerebral cortex; A6 frontal lobe; A7 hippocampus; A8 medulla oblongata; B1 occipital lobe; B2 putamen; B3 substantia nigra; B4 temporal lobe; B5 thalamus; B6 sub-thalamic nucleus; B7 spinal cord; C1 heart; C2 aorta; C3 skeletal muscle; C4 colon; C5 bladder; C6 uterus; C7 prostate; C8 stomach; D1 testis; D2 ovary; D3 pancreas; D4 pituitary gland; D5 adrenal gland; D6 thyroid gland; D7 salivary gland; D8 mammary gland; E1 kidney; E2 liver; E3 small intestine; E4 spleen; E5 thymus; E6 peripheral leukocytes; E7 lymph node; E8 bone marrow; F1 appendix; F2 lung; F3 trachea; F4 placenta; G1 fetal brain; G2 fetal heart; G3 fetal kidney; G4 fetal liver; G5 fetal spleen; G6 fetal thymus; G7 fetal lung.

This initial analysis was extended by using the PC-LECTIN probe to analyze an RNA dot blot matrix of 50 normal human tissues (Clontech, Palo Alto, Calif., Human Master Blot™). The results show strong PC-LECTIN expression only in testis and fetal spleen (FIG. 14). Lower levels of expression were detected in salivary gland and fetal kidney. No expression was detected in the following tissues:

brain, amygdala, caudate nucleus, cerebellum, cerebral cortex, frontal lobe, hippocampus, medulla oblongata, occipital lobe, putamen, substantia nigra, temporal lobe, thalamus, sub-thalamic nucleus, spinal cord, heart, aorta, skeletal muscle, colon, bladder, uterus, prostate, stomach, ovary, pancreas, pituitary gland, adrenal gland, thyroid gland, mammary gland, kidney, liver, small intestine, spleen, thymus, peripheral leukocytes, lymph node, bone marrow, appendix, lung, trachea, placenta, fetal brain, fetal heart, fetal liver, fetal thymus fetal lung.

To analyze PC-LECTIN expression in human prostate cancer tissues, RNAs derived from human prostate cancer xenografts were also analyzed. All RNA samples were quantitatively normalized by ethiduim bromide staining and subsequent analysis with a labeled β-actin probe. The results (FIG. 4C) show high level PC-LECTIN expression, particularly in the LAPC-9 AD xenograft, with lower but significant level expression detected in the remaining xenografts.

Figure 5:
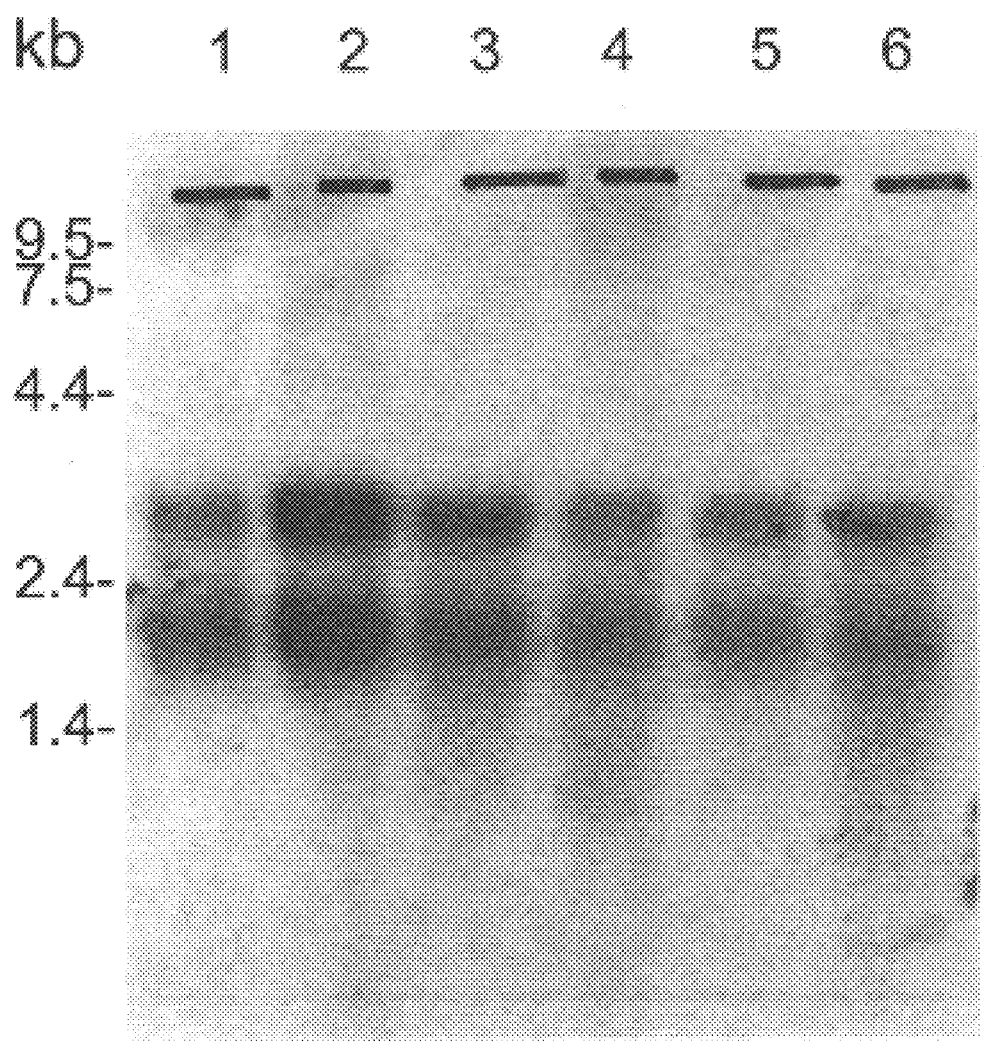
FIG. 5. Northern blot analysis of PC-LECTIN in prostate cancer xenografts using an SSH fragment probe. The results show that PC-LECTIN is highly expressed in tumors that are grown either subcutaneously (sc) or intratibially (it) within the mouse bone. Lanes 1–3 are LAPC-9 AD sc; lanes 4–6 are LAPC-9AD it.
Figure 6:
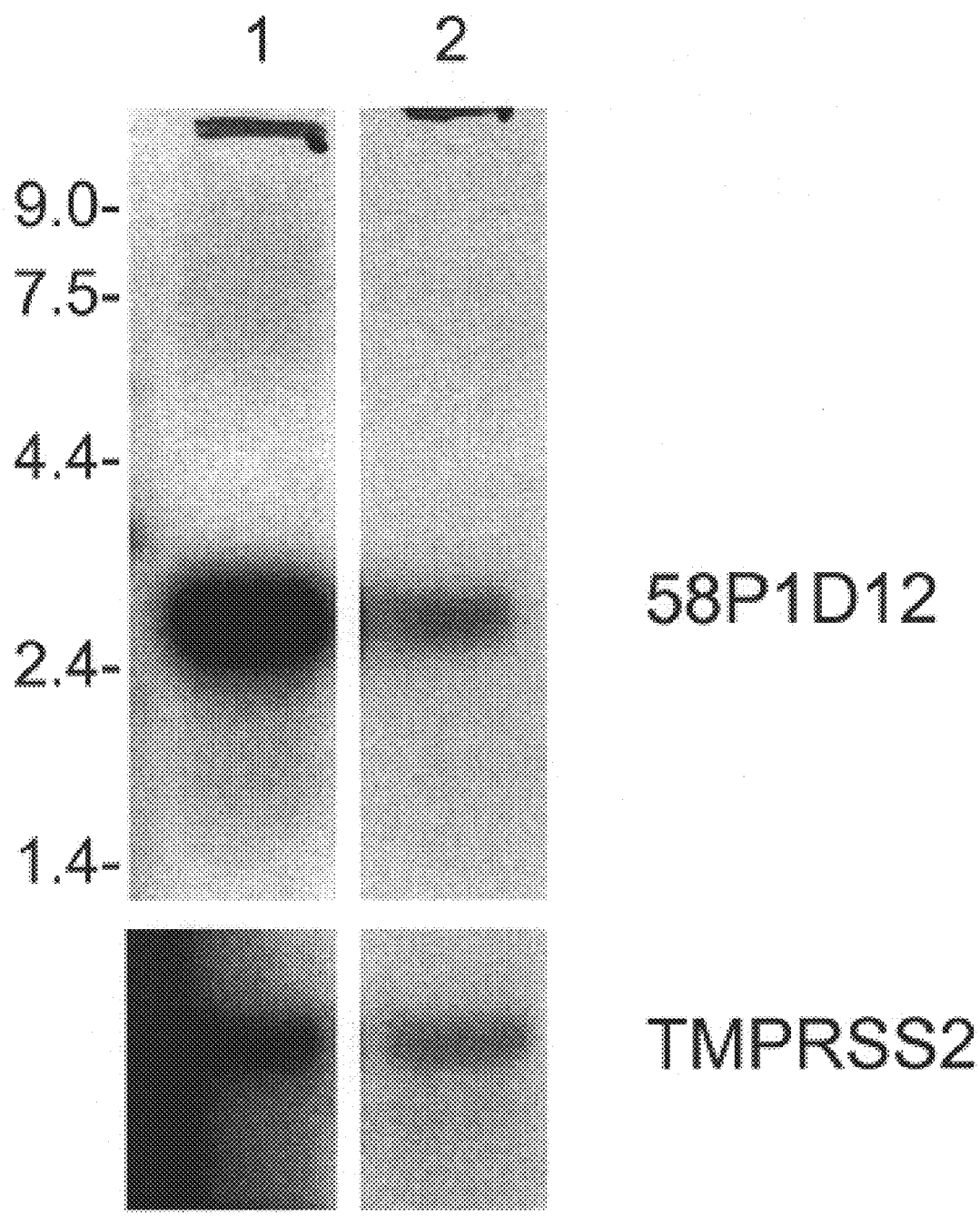
FIG. 6. Northern expression analysis of PC-LECTIN/58P1D12 in tumors of 28 day-post castrated males (lane 2) was compared to the expression in tumors of intact males (lane 1). Expression is dramatically reduced in tumors from castrated males. As a control, expression of a known androgen-regulated gene, TMPRSS2, was also shown to be down-regulated after castration. These data suggest that PC-LECTIN expression in prostate tumors is dependent on the presence of androgen.

Northern blot analysis using a PC-LECTIN SSH fragment probe shows that PC-LECTIN is highly expressed in tumors that are grown either subcutaneously (sc; FIG. 5; Lane 2) or intratibially (it; FIG. 5; Lane 1) within the mouse bone. To investigate whether PC-LECTIN expression is dependent on the presence of androgen, LAPC-9 AD tumors were grown in male SCID mice. The mice were castrated and tumors were harvested 28 days later. The expression of PC-LECTIN in tumors of 28 day-post castrated males was compared to the expression in tumors of intact males. The results show that PC-LECTIN expression is dramatically reduced in tumors from castrated males (FIG. 6). As a control, expression of a known androgen-regulated gene, TMPRSS2 (See WO99/62942), was also shown to be down-regulated after castration (FIG. 6). These data suggest that PC-LECTIN expression in prostate tumors is dependent on the presence of androgen.

In addition, RT-PCR can be used to analyze expression of PC-LECTIN in various tissues, including patient-derived cancers. First strand cDNAs are generated from 1 µg of mRNA with oligo (dT)12–18 priming using the Gibco-BRL Superscript Preamplification system. The manufacturers protocol can be used and includes an incubation for 50 min at 42° C. with reverse transcriptase followed by RNAse H treatment at 37° C. for 20 min. After completing the reaction, the volume is increased to 200 µl with water prior to normalization. First strand cDNAs are prepared from various tissues of interest. Normalization can be performed by PCR using primers to actin and GAPDH. Semi-quantitative PCR is performed using primers to PC-LECTIN.

Example 4

Biochemical Characterization of PC-LECTIN Protein

Figure 7:
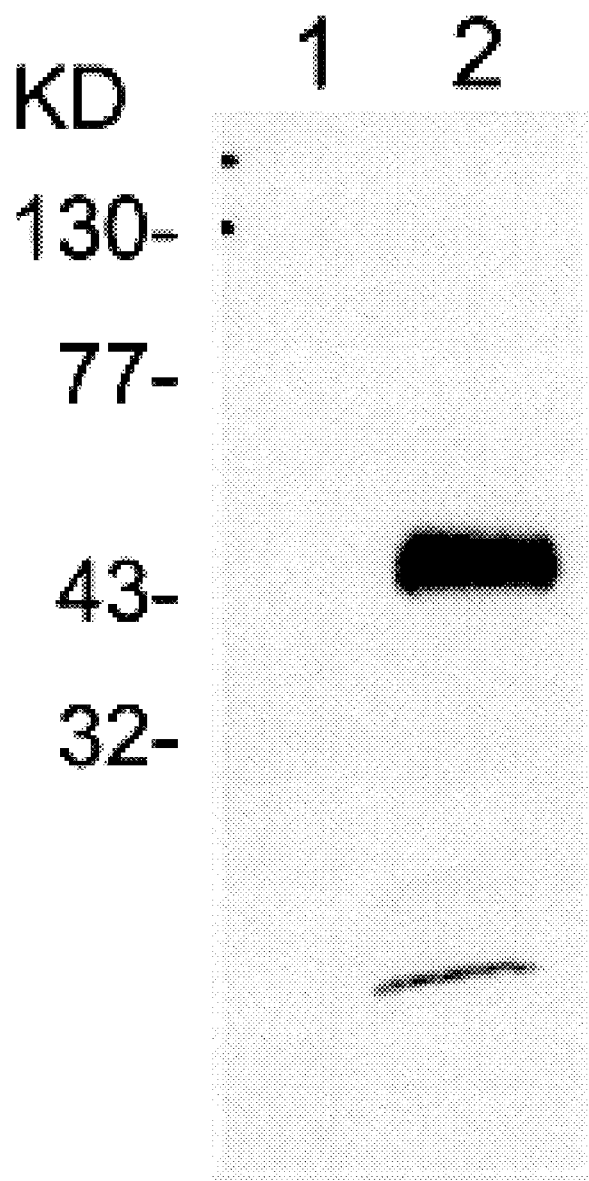
FIG. 7. Cell surface localization of PC-LECTIN antigen. Shown is a photograph of an exposed western blot of streptavidin-sepharose purified cell surface biotinylated 293T cells transfected with vector containing cDNA encoding 6His-tagged PC-LECTIN (lane 2) using an anti-His monoclonal antibody. The PC-LECTIN protein was not detected in streptavidin precipitates from non-biotinylated cells transfected with the same vector (lane 1). Molecular weight markers are indicated in kilodaltons (kD).

To initially characterize the PC-LECTIN protein, PC-LECTIN cDNA was cloned into the pcDNA 3.1 Myc-His plasmid (Invitrogen), which encodes a 6His tag at the carboxyl terminus, transfected into 293T cells, and labeled with a water soluble biotinylation reagent that is excluded from live cells. Biotinylated cell surface proteins were affinity purified with streptavidin-sepharose and probed with anti-His antibodies. Western blotting of streptavidin purified proteins clearly show cell surface biotinylation of PC-LECTIN in transfected 293T cells (FIG. 7). PC-LECTIN protein was not detected in streptavidin precipitates from non-biotinylated transfected cells (FIG. 7).

Example 5

Expression of Recombinant PC-LECTIN Protein in Mammalian Systems

For mammalian expression, PC-LECTIN may be cloned into several vectors, including pcDNA 3.1 myc-His-tag (Invitrogen) and the retroviral expression vector pSRαtkneo (Muller et al., 1991, MCB 11:1785). Using these expression vectors, PC-LECTIN may be expressed in several cell lines, including PC-3, NIH 3T3, mouse L cell fibroblasts and 293T.

Recombinant retrovirus encoding the PC-LECTIN protein was generated in human 293T cells (Pear et al., 1993, PNAS 90:8392–8396) and was used to infect NIH 3T3 cells, which were selected in G418 for two weeks to generate stable lines. Expression of PC-LECTIN was confirmed by northern blotting using a PC-LECTIN cDNA probe.

The mammalian cell lines expressing PC-LECTIN may be used in several in vitro and in vivo assays, including cell proliferation in tissue culture, activation of apoptotic signals, tumor formation in SCID mice, and in vitro invasion using a membrane invasion culture system (MICS) (Welch et al., Int. J. Cancer 43: 449–457).

Example 6

Production of Recombinant PC-LECTIN in a Baculovirus System

To generate a recombinant PC-LECTIN protein in a baculovirus expression system, the PC-LECTIN cDNA is cloned into the baculovirus transfer vector pBlueBac 4.5 (Invitrogen), which provides a His-tag at the N-terminus Specifically, pBlueBac—PC-LECTIN is co-transfected with helper plasmid pBac-N-Blue (Invitrogen) into SF9 (Spodoptera frugiperda) insect cells to generate recombinant baculovirus (see Invitrogen instruction manual for details). Baculovirus is then collected from cell supernatant and purified by plaque assay.

Recombinant PC-LECTIN protein is then generated by infection of HighFive insect cells (InVitrogen) with the purified baculovirus. Recombinant PC-LECTIN protein may be detected using anti-PC-LECTIN antibody. PC-LECTIN protein may be purified and used in various cell based assays or as immunogen to generate polyclonal and monoclonal antibodies specific for PC-LECTIN.

Example 7

Generation of a Secreted Recombinant PC-LECTIN-Alkaline Phosphatase Fusion Protein The identification of proteins interacting with PC-LECTIN could help assign function and may identify novel therapeutic targets and diagnostic markers for prostate cancer. The construction of an alkaline phosphatase-PC-LECTIN fusion protein may be used to detect and clone proteins interacting with PC-LECTIN while also generating an immunogen for monoclonal antibody and polyclonal antibody production.

The AP-TAG system from GenHunter Corporation (Nashville, Tenn. cat# Q202) was utilized to make the fusion protein and for detection of PC-LECTIN binding. The PC-LECTIN cDNA (FIGS. 1A–D; SEQ ID NO: 1), without the signal sequence, was cloned into pAPtag-5 (GenHunter Corp. Nashville, Tenn.). The PC-LECTIN.HindIII and PC-LECTIN.BamH1 primers shown below were used to amplify the PC-LECTIN open reading frame from amino acids 22 to 213 from the plasmid template PC-LECTIN clone 2. The HindIII and BamH1 digested PCR product was ligated into Hindlll and BglII digested pAPtag-5, while keeping the IgGK signal sequence, PC-LECTIN ORF, and alkaline phosphatase all in frame. The PC-LECTIN-AP fusion protein contains an IgGK signal sequence to promote secretion along with myc/His tags at the carboxy terminus of alkaline phosphatase.

PC-LECTIN.HINDIII Primer (SEQ ID NO: 23):

GTGTAAGCTTCCCGCCGCGTGGTCAGCGGC

PC-LECTIN.BAMHI Primer (SEQ ID NO: 24):

CACAGGATCCTATACCTGCTTCAGTAAC

Figures 8A, 8B:
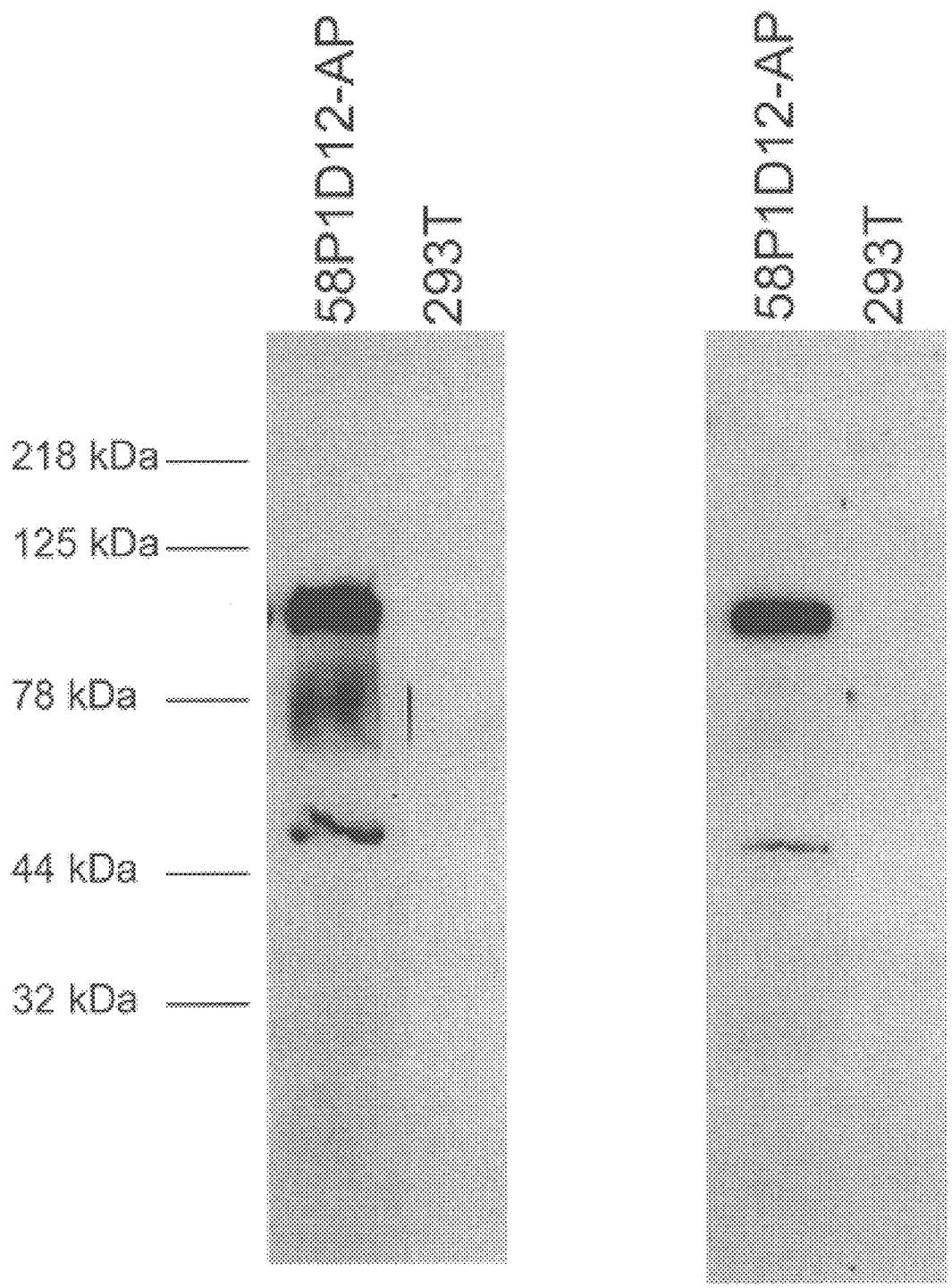
FIG. 8A. Western blot showing that anti-HIS antibodies recognize secreted recombinant PC-LECTIN/58P1D12-AP fusion protein in conditioned media. The lanes contain 20 μl conditioned media from unmodified 293T cells or 293T cells transfected with PC-LECTIN/58P1D12-AP collected 4 hours after media change.
FIG. 8B. Western blot showing that anti-alkaline phosphatase antibodies also recognize secreted recombinant PC-LECTIN/58P1D12-AP fusion protein in conditioned media. The lanes contain 20 μl conditioned media from unmodified 293T cells 293T is transfected with PC-LECTIN/58P1D12-AP collected 4 hours after media change, as in FIG. 8A.

This PC-LECTIN-AP fusion protein construct was used to transfect 293T cells, and the presence of secreted fusion protein into the culture media was monitored by western blot using anti-alkaline phosphatase and anti-HIS antibodies. The results of this analysis, shown in FIG. 8, show detection of an approximately 100 kDa fusion protein in conditioned media of transfected 293T cells.

Amino acids 22 to 213 were also cloned into the pAPTag-5 vector using PCR with primers containing restriction enzymes HindIII and XhoI to produce a IgGK signal sequence fusion at the N-terminus and the myc/His tags at the C-terminus of PC-LECTIN extracellular domain. This construct is similar to 58P1D12pAPtag above but without the AP fusion.

The entire coding sequence of PC-LECTIN (aa 1–273) was cloned into pSRa. Primers encoding the ORF and the restriction sites EcoRI and XbaI amplified the insert from PC-LECTIN clone 2 (pBK.CMV). The insert was ligated to pSRa after digestion of both with EcoRI and XbaI. This construct was used to generate virus and make cell lines stably expressing PC-LECTIN protein.

The entire coding sequence of PC-LECTIN (aa 1–273) was cloned into pcDNA3.1/myc-HIS (Invitrogen). Primers encoding the ORF and the restriction sites EcoRI and XbaI amplified the insert from PC-LECTIN clone 2 (pBK.CMV). The insert was ligated to pcDNA3.1/myc-HIS (Invitrogen) after digestion of both with EcoR1 and XbaI. Western blot analysis confirmed expression PC-LECTIN protein when 293T cells were transfected with this construct.

Example 8

Detection and Cloning of PC-LECTIN Binding Partner

PC-LECTIN is a transmembrane protein with lectin C-type domains that may interact with a binding partner protein. To detect PC-LECTIN receptor binding, several cell lines, tissues, and plates coated with glycoprotein (e.g., human or mouse IgG, bovine RNase, ovalbumin, human transferrin, fetuin glycophorin, sialogylcophorin) are incubated with the PC-LECTIN-AP fusion protein using procedures in Cheng and Flanagan, 1994, Cell 79:157–168. After washing the cells and adding the AP substrate BCIP, which forms an insoluble blue precipitate upon dephosphorylation, PC-LECTIN binding to cell surface receptor can be detected using a microscope to look for cells staining blue. The cell lines that may be screened include LNCaP, PC-3, DU145, TSUPR, PREC, LAPC4, 293T, NIH 3T3, and other cancer cell lines. Tissues may also be screened such as the LAPC xenografts, prostate tissue and prostate carcinoma. Once PC-LECTIN-AP cell surface binding is observed, an equilibrium dissociation rate constant can be calculated to evaluate the strength of the binding interaction. In addition, the number of cell surface receptors per cell can be determined. The cell line or tissue with the highest binding capacity for PC-LECTIN may then be used to clone the receptor. Binding of PC-LECTIN to a specific carbohydrate moiety can be confirmed by demonstrating binding inhibition by low concentrations of specific related monosaccharide.

Expression cloning strategies such as those described in Tartaglia et al., 1995, Cell 83: 12631271, Cheng and Flanagan and others may be used to clone the receptor for PC-LECTIN. In one approach, an expression library is constructed from the cells showing PC-LECTIN-AP binding. The library is made as pools of approximately 1000 clones and is screened by a sib selection procedure. Transient transfection of COS cells with DNA from each pool and subsequent screening with PC-LECTIN-AP binding, washing, and staining for AP activity identifies cells binding PC-LECTIN and consequently expression of PC-LECTIN receptors. After successive rounds of pool subdivision and screening, single colonies binding to PC-LECTIN-AP are identified.

Alternatively, an expression library is generated in phage using standard technology (Stone J. in Current Protocols in Molecular Biology (1997): 20.3.1–20.3.9). Membrane lifts are probed using the PC-LECTIN-AP fusion protein according to Example 6 and a BCIP alkaline phosphatase assay is used for detection. Plaques binding PC-LECTIN-AP and producing a blue precipitate are picked and plasmids containing the gene for the receptor are excised. An important advantage of this approach is that cytoplasmic or secreted proteins interacting with PC-LECTIN are also identified.

Example 9

Figure 9A:
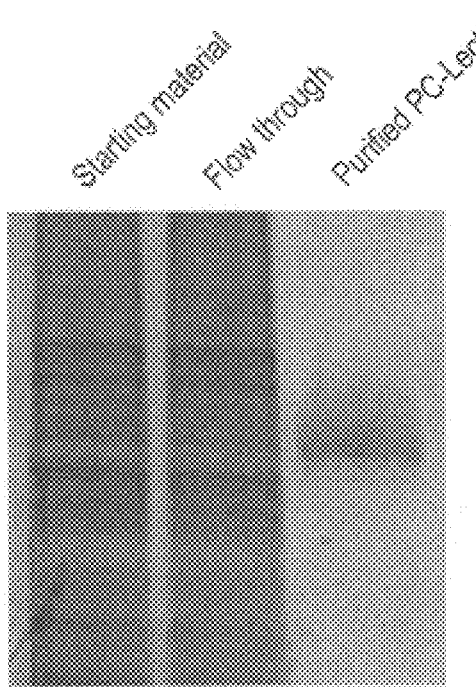
FIG. 9A. Expression and purification of the extracellular domain of PC-LECTIN. 293T cells were transfected with a Tag5 secretion expression vector encoding the extracellular domain of PC-LECTIN with a C-terminal 6× His tag. Conditioned medium was subjected to immobilized metal affinity chromatography using Ni-NTA agarose (Qiagen). The starting conditioned medium, the flow through, and the eluted purified material was run on a 10–20% SDS-PAGE gel and silver stained.
Figure 9B:
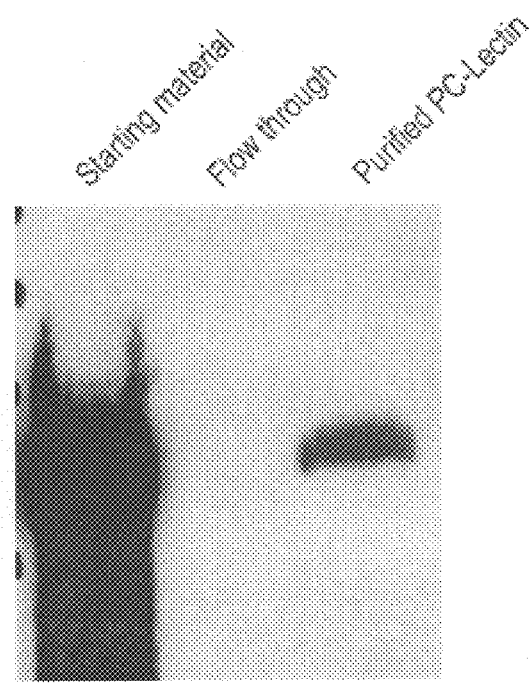
FIG. 9B. Conditioned medium from 293T cells transfected as described for FIG. 9A was run on a 10–20% SDS-PAGE gel and transferred to nitrocellulose and subjected to western blotting using an anti-His pAb.

Expression and Purification of PC-LECTIN Extracellular Domain 293T cells were transfected with a Tag5 secretion expression vector encoding the extracellular domain (amino acids 22–213) of PC-LECTIN with a C-terminal 6× His tag. A stable cell line was then generated by zeocin selection. The cell line was grown in spinner culture in 293 SFMII serum free medium (Gibco) and conditioned medium was collected for purification. Conditioned medium was concentrated and buffer exchanged into binding buffer (50 mM sodium phosphate buffer pH 8.0, 500 mM NaCl, and 10 mM imidazole) and subjected to immobilized metal affinity chromatography using Ni-NTA agarose (Qiagen). The starting conditioned medium, the flow through, and the eluted purified material was run on a 10–20% SDS-PAGE gel and silver stained (FIG. 9A) or transferred to nitrocellulose and subjected to western blotting using an anti-His pAb (FIG. 9B).

Example 10

Polyclonal and Monoclonal Antibodies to PC-LECTIN

To generate polyclonal antibodies towards PC-LECTIN, three different peptides were generated towards the extracellular domain of PC-LECTIN. The peptide sequences are:

GLWRNGDGQTSGAC (14mer; SEQ ID NO: 25),

GGPYLYQWNDDRCNM (15mer; SEQ ID NO: 26), and

EARLACESEGGVLL (14mer; SEQ ID NO: 27).

The peptides were conjugated to KLH keyhole limpet hemocyanin) and were used to immunize rabbits. Serum from the rabbits was tested for reactivity towards PC-LECTIN protein using western blotting of cell lysates and using FACS on whole cells (See Example 11 below).

Titer was monitored by ELISA to the peptide and by western blotting using recombinant cell lines expressing the PC-LECTIN cDNA. Subsequent experiments were performed with antibodies generated from amino acids 204–217 of the PC-LECTIN protein (GLWRNGDGQTSGAC; SEQ ID NO: 25).

To generate monoclonal antibodies, the extracellular domain of PC-LECTIN was efficiently expressed and purified from conditioned media of 293T cells expressing the Tag5 PC-LECTIN secretion vector as described in Example 9 above. The purified protein was used to immunize BalbC mice. Mice were initially injected intraperitoneally with 50 µg of protein in complete Freund's adjuvant and then boosted 3 weeks later with 50 µg protein in incomplete Freund's adjuvant. Boosts then continued on a 2 week immunization schedule and titers of immunized mouse serum were monitored by ELISA using Tag5 PC-LECTIN as target and specificity by western blot analysis of cell lines and tissue lysates.

Example 11

PC-LECTIN Expression in Recombinant Cell Lines and Testis

The immunized mouse serum was used to analyze PC-LECTIN expression by western blot and immunoprecipitation using cell lysates of recombinant cell lines and normal testis. In addition, PC-LECTIN expression on the cell surface of Rat1-PC-LECTIN cells was analyzed by flow cytometry using the immunized mouse serum.

Rat1 cells stably infected with either neo control virus or virus encoding PC-LECTIN were lysed in RIPA buffer (25 mM Tris pH 7.5, 150. mM NaCl, 1% Triton X-100, 0.5% sodium deoxycholate, 0.1% SDS, 2 mM EDTA, 100 µg/ml PMSF, and 2 µM leupeptin). 200 µg of lysates were then subjected to immunoprecipitation with serum from mice immunized with purified Tag5-PC-LECTIN protein. Briefly, 3 µl of serum was incubated with lysates (200 µg protein in 1 ml) and incubated overnight at 4° C. 50 µl of a 50% slurry of Protein G beads in RIPA buffer was then added and further incubated for 1 hour at room temperature. Immunoprecipitates were washed 4× with RIPA buffer and solubilized in 40 µl of 3× SDS-PAGE sample buffer and heated at 100° C. 25 µl of solubilized immunoprecipitates or 25 µg of the indicated RIPA lysates were separated on a 10–20% SDS-PAGE gel and transferred to nitrocellulose.

Western blot analysis was then carried out with either an affinity purified rabbit anti-PC-LECTIN peptide pAb (2 µg/ml, FIG. 10A) or with a 1:1000 dilution of immunized mouse serum diluted into Tris buffered saline containing 0.15% Tween-20 (TBS-T, pH 7.5) and 1% nonfat milk (FIG. 10B). Blots were incubated for 2 hours at room temperature with serum and then washed 3× with TBS-T. Immunoreactive bands were then developed by incubation with either anti-rabbit Ig or anti-mouse IgG HRP-conjugated secondary Abs and visualized by incubation with enhanced chemiluminescence substrate (ECL, Amersham) and exposure to autoradiographic film.

Figure 11:
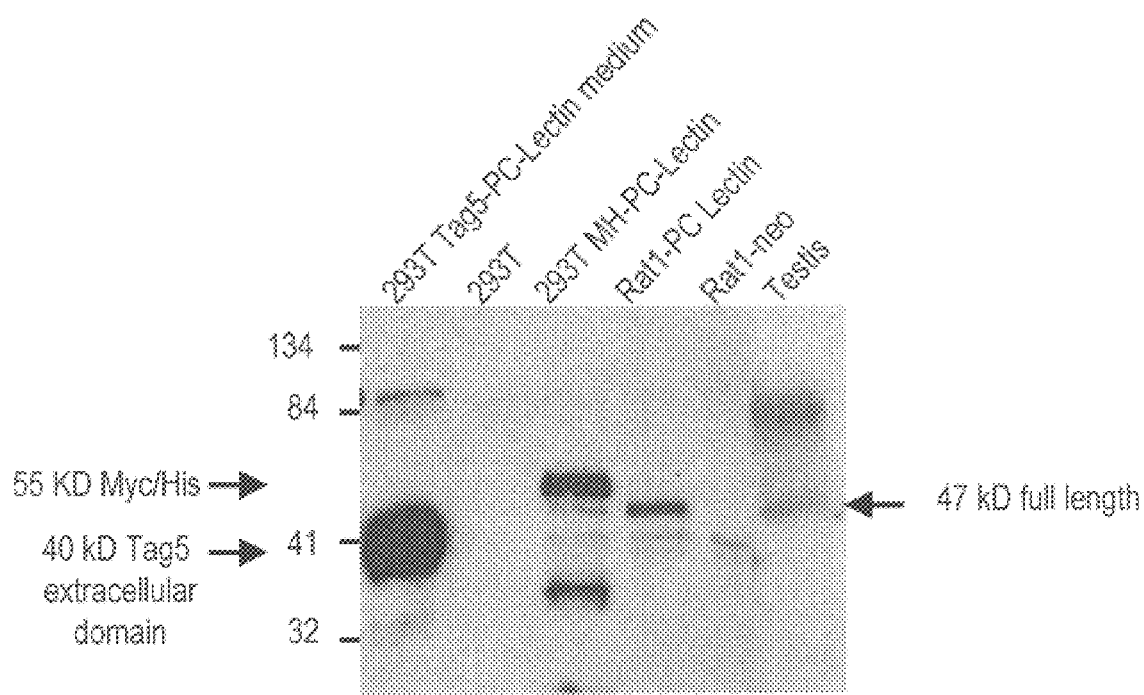
FIG. 11. Expression of PC-LECTIN in recombinant cell lines and testis. Cell lysates of 293T cells transiently transfected with either pCDNA3.1 Myc/His PC-LECTIN or empty vector and of Rat1 cells stably infected with either neo control or PC-LECTIN retrovirus and of normal testis were separated by SDS-PAGE and transferred to nitrocellulose for western analysis. Indicated with arrows are the 47 kD band representing full length PC-LECTIN, the 40 kD extracellular domain, and the 55 kD Myc/His tagged protein.

Cell lysates of 293T cells transiently transfected with either pCDNA3.1 Myc/His PC-LECTIN or empty vector and of Rat1 cells stably infected with either neo control or PC-LECTIN retrovirus and of normal testis were separated by SDS-PAGE and transferred to nitrocellulose. Western analysis was then carried out as described above. The results are shown in FIG. 11. Indicated with arrows are the 47 kD band representing full length PC-LECTIN, the 40 kD extracellular domain, and the 55 kD Myc/His tagged protein.

Figure 12:
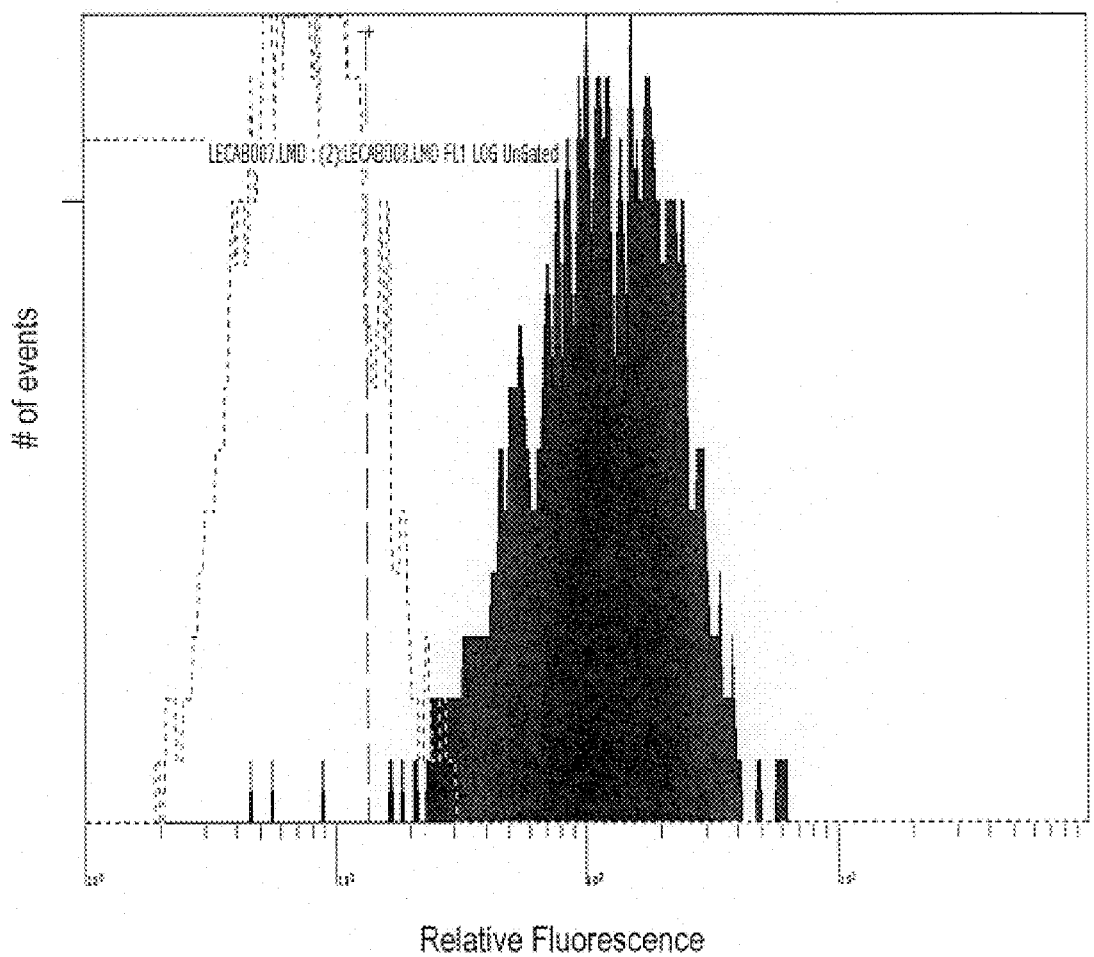
FIG. 12. Cell surface recognition of PC-LECTIN on Rat1 cells with Tag5 PC-LECTIN immunized mouse serum using flow cytometry. Either Rat1-neo (open area) or Rat1-PC-LECTIN cells ($5\times10^5$; shaded area) were incubated with a 1:2000 dilution of Tag5 PC-LECTIN immunized mouse serum. 3,000 cells from each sample were analyzed by flow cytometry for cell surface staining of PC-LECTIN. Number of events is plotted as a function of relative fluorescence.

Cell surface recognition of PC-LECTIN on Rat1 cells with Tag5 PC-LECTIN immunized mouse serum was analyzed by flow cytometry. Either Rat1-neo or Rat1-PC-LECTIN cells ($5 \times 10^5$) were incubated with a 1:2000 dilution of Tag5 PC-LECTIN immunized mouse serum in PBS containing 1% FBS and 0.02% NaN3 (flow buffer) for 1 hour on ice. Cells were washed 2× with ice cold flow buffer and then incubated with a 1:200 dilution of anti-mouse IgG-FITC conjugate on ice for 30 minutes. Cells were washed 2× with flow buffer and resuspended in PBS containing 1% paraformaldehyde. 3,000 cells from each sample were then analyzed by flow cytometry for cell surface staining of PC-LECTIN. Results are shown in FIG. 12.

Figure 13:
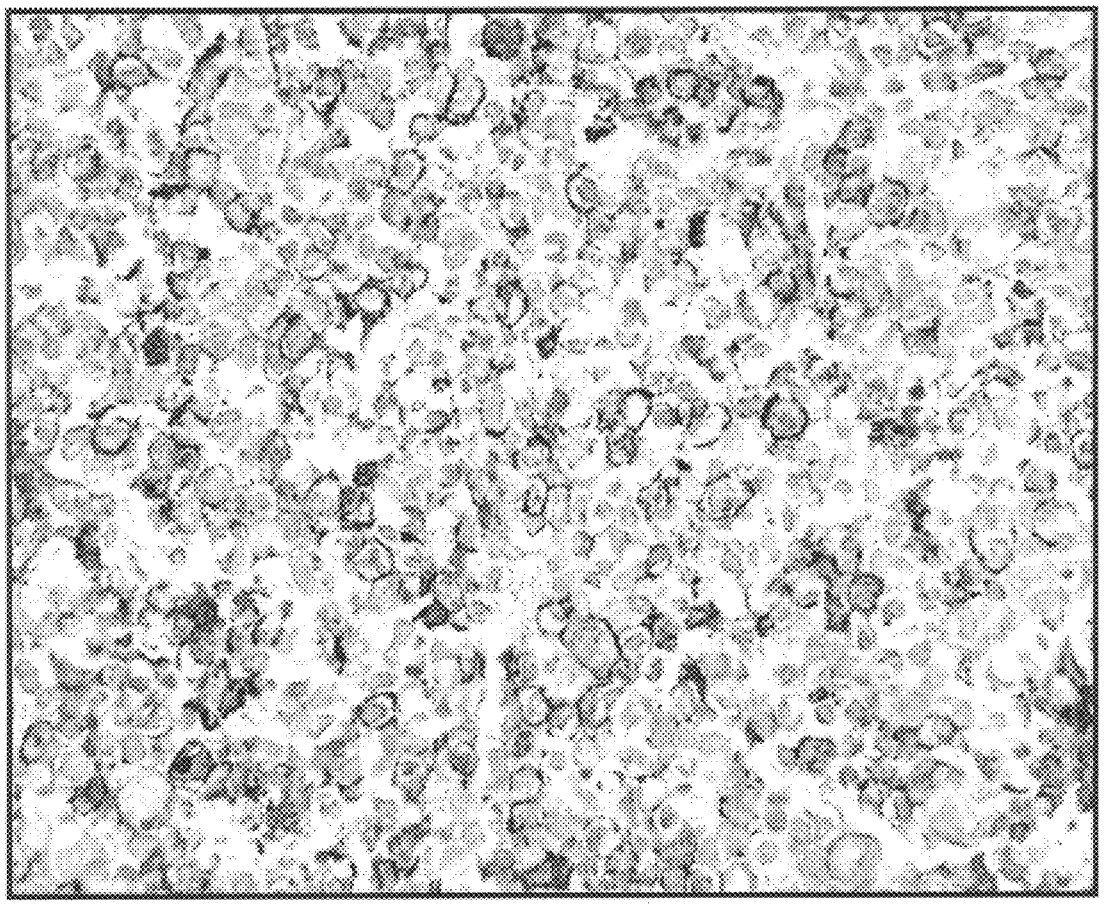
FIG. 13. Immunohistochemical analysis of PC-LECTIN-transfected293T cells labeled with rabbit polyclonal antibody, showing cell surface expression of PC-LECTIN. The antibody did not stain parental 293T cells.

Cell surface expression of PC-LECTIN was further analyzed using immunohistochemical analysis of formalin-fixed, paraffin-embedded cell pellets. The PC-LECTIN-transfected 293T cells were labeled with rabbit polyclonal antibody at 7.5 µg/ml (SHIER II pretreatment). Cell surface expression of PC-LECTIN was detected as shown in FIG. 13. The antibody did not stain parental 293T cells.

Example 12

Carbohydrate Binding Specificity of PC-LECTIN

PC-LECTIN was analyzed for carbohydrate binding specificity using a 96-well microassay employing the Tag5 extracellular domain of PC-LECTIN purified from conditioned medium. Analysis of the ability of PC-LECTIN to bind to a variety of carbohydrate moieties on purified protein preparations demonstrates a specificity for high mannose residues as well as N-acetylglucosamine. This specificity is similar to that seen for the lectin Concanavalin A.

The wells of a 96-well microtiter plate were coated with the appropriate glycoprotein at 1 ug/well in PBS and incubated overnight at 37° C. The wells were washed once with 1× Tris-Buffered Saline(TBS) and then blocked with 3% BSA (Sigma) in PBS for 1 hour with rocking. The wells were incubated with either buffer control, or 50 ng of PC-LECTIN or 50 ng of Concanavalin A (ConA) in 1×TBS supplemented with 2 mM $CaCl_2$. The plates were then incubated for 2 hours at room temperature with rocking. The plates were then washed 3× with TBS, 2 mM $CaCl_2$, 0.05% Tween-20, and once with TBS, 2 mM $CaCl_2$. The wells were then incubated for 1 hour at room temperature with either an anti-His6 rabbit pAb (for PC-LECTIN detection, Santa Cruz Biotechnology) or an anti-ConA rabbit pAb (for ConA detection, Vector Laboratories) each diluted 1/1000 in TBS, 2 mM $CaCl_2$ plus 1% BSA. The wells were washed as before. The wells were then incubated with anti-rabbit Ig HRP conjugate diluted 1/3,000 with TBS, 2 mM $CaC_2$ plus 1% BSA. The wells were washed again and then developed using TMB ELISA (GIBCO-BRL) according to the manufacturer's guidelines, and the optical density was measured at 450 nM. Data are shown in Table 1, and represent the means of duplicate determinations.

TABLE 1

PC-LECTIN carbohydrate binding specificity

| Glycoprotein | Sugar Type | PC-LECTIN OD 450 | ConA OD450 |
|---|---|---|---|
| Chicken Egg Albumin | High Mannose | 0.962 | 3.12 |
| Avidin | High Mannose | 1.104 | 3.361 |
| Chorionic Gonadotropin | N-Acetylneuraminic acid | 0.013 | — |

TABLE 1-continued

PC-LECTIN carbohydrate binding specificity

| Glycoprotein | Sugar Type | PC-LECTIN OD 450 | ConA OD450 |
|---|---|---|---|
| Chicken Egg conalbumin | Bisecting GlcNAc | 0.663 | 3.1 |
| Thyrogolobulin, Bovine | Mannose -6-phosphate | 0.979 | — |
| Laminin, Human | tri-mannose core, GlcNAc | 0.389 | — |
| C-7913 | 1 | 0.038 | — |
| T antigen | galacto-N-biose, GalB1, 3GalNAc | — | 0.015 |

—: not examined
Con A: concanavalin A
1: C-7913 carboxyethylthioethyl 2-acetoamido-2-deoxy-4-o-B-s-galactopyranosyl-b-d-glucopyranoside BSA
GlcNAc: N-acetyl glucosamine
GalNAc: N-acetyl galactosamine
GalB1: galactose beta 1 linkage Example 13

Predicted Binding of PC-LECTIN Peptides to HLA-A2

To identify PC-LECTIN peptides predicted to bind to the human MHC class I molecule HLA-A2, the complete amino acid sequence of the 58P1D12(PC-LECTIN)-F3C4 family member protein was entered into the HLA Peptide Motif Search algorithm found in the Bioinformatics and Molecular Analysis Section (BIMAS) Web site (http://bimas.dcrt.nih.gov/). The results of 58P1D12-F3C4 predicted binding peptides are shown in Table 2. The top 5 ranking candidates are shown along with their location, the amino acid sequence of each specific peptide, and an estimated binding score. The binding score corresponds to the estimated half-time of dissociation of complexes containing the peptide at 37° C. at pH 6.5. Peptides with the highest binding score are predicted to be the most tightly bound to HLA Class I on the cell surface and thus represent the best immunogenic targets for T-cell recognition. Actual binding of peptides to HLA-A2 can be evaluated by stabilization of HLA-A2 expression on the antigen-processing defective cell line T2 (Xue et al., 1997, Prostate 30:73–8; Peshwa et al., 1998, Prostate 36:129–38). Immunogenicity of specific peptides can be evaluated in vitro by stimulation of CD8+ cytotoxic T lymphocytes (CTL) in the presence of dendritic cells (Xue et al., 1997, Prostate 30:73–8; Peshwa et al., 1998, Prostate 36:129–38).

TABLE 2

Predicted Peptide Binding Scores

| Rank | Start Position | Subsequence Residue Listing | Score (Estimate of half time of disassociation) |
|---|---|---|---|
| 1 | 6 | WIGFTYKTA (SEQ ID NO: 28) | 4.7 |
| 2 | 21 | ATGEHQAFT (SEQ ID NO: 29) | 2.3 |
| 3 | 41 | FGNCVELQA (SEQ ID NO: 30) | 0.2 |
| 4 | 43 | NCVELQASA (SEQ ID NO: 31) | 0.1 |
| 5 | 37 | DNHGFGNCV (SEQ ID NO: 32) | 0.1 |

Example 14

Identification of Potential Signal Transduction Pathways

To determine whether PC-LECTIN directly or indirectly activates known signal transduction pathways in cells, luciferase (luc) based transcriptional reporter assays are carried out in cells expressing PC-LECTIN. These transcriptional reporters contain consensus binding sites for known transcription factors that lie downstream of well characterized signal transduction pathways. The reporters and examples of their associated transcription factors, signal transduction pathways, and activation stimuli are listed below.

1. NFkB-luc, NFkB/Rel; Ik-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis
5. p53-luc, p53; SAPK; growth/differentiation/apoptosis
6. CRE-luc, CREB/ATF2; PKA/p38; growth/apoptosis/stress PC-LECTIN-mediated effects may be assayed in cells showing mRNA expression. Luciferase reporter plasmids may be introduced by lipid mediated transfection (TFX-50, Promega). Luciferase activity, an indicator of relative transcriptional activity, is measured by incubation of cells extracts with luciferin substrate and luminescence of the reaction is monitored in a luminometer.

Example 15

In Vitro Assays of PC-LECTIN Function

The expression of PC-LECTIN in prostate cancer provides evidence that this gene has a functional role in tumor progression and/or tumor initiation. It is possible that PC-LECTIN functions as a receptor involved in activating proliferation signals. PC-LECTIN function can be assessed in mammalian cells using in vitro approaches. For mammalian expressio, PC-LECTIN can be cloned into a number of appropriate vectors, including pcDNA 3.1 myc-His-tag and the retroviral vector pSRαtkneo (Muller et al., 1991, MCB 11:1785). Using such expression vectors, PC-LECTIN can be expressed in several cell lines, including PC-3, NIH 3T3, LNCaP and 293T. Expression of PC-LECTIN can be monitored using anti-PC-LECTIN antibodies and northern blot analysis.

Mammalian cell lines expressing PC-LECTIN can be tested in several in vitro and in vivo assays, including cell proliferation in tissue culture, activation of apoptotic signals, tumor formation in SCID mice, and in vitro invasion using a membrane invasion culture system (MICS; Welch et al., Int. J. Cancer 43: 449–457). PC-LECTIN cell phenotype is compared to the phenotype of cells that lack expression of PC-LECTIN.

Cell lines expressing PC-LECTIN can also be assayed for alteration of invasive and migratory properties by measuring passage of cells through a matrigel coated porous membrane chamber (Becton Dickinson). Passage of cells through the membrane to the opposite side is monitored using a fluorescent assay (Becton Dickinson Technical Bulletin #428) using calcein-Am (Molecular Probes) loaded indicator cells.

Cell lines analyzed include parental and PC-LECTIN over-expressing PC3, NIH 3T3 and LNCaP cells. To determine whether PC-LECTIN-expressing cells have chemoattractant properties, indicator cells are monitored for passage through the porous membrane toward a gradient of PC-LECTIN conditioned media compared to control media. This assay may also be used to qualify and quantify specific neutralization of the PC-LECTIN induced effect by candidate cancer therapeutic compositions.

The function of PC-LECTIN can be evaluated using anti-sense RNA technology coupled to the various functional assays described above, e.g. growth, invasion and migration. Anti-sense RNA oligonucleotides can be introduced into PC-LECTIN expressing cells, thereby preventing the expression of PC-LECTIN. Control and anti-sense containing cells can be analyzed for proliferation, invasion, migration, apoptotic and transcriptional potential. The local as well as systemic effect of the loss of PC-LECTIN expression can be evaluated.

Example 16

In Vivo Assay for PC-LECTIN Tumor Growth Promotion

The effect of the PC-LECTIN protein on tumor cell growth may be evaluated in vivo by gene overexpression in tumor-bearing mice. For example, SCID mice can be injected subcutaneously on each flank with $1 \times 10^6$ of either PC3, TSUPR1, or DU145 cells containing tkNeo empty vector or PC-LECTIN. At least two strategies may be used: (1) Constitutive PC-LECTIN expression under regulation of a promoter such as a constitutive promoter obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), or from heterologous mammalian promoters, e.g., the actin promoter or an immunoglobulin promoter, provided such promoters are compatible with the host cell systems, and (2) Regulated expression under control of an inducible vector system, such as ecdysone, tet, etc., provided such promoters are compatible with the host cell systems. Tumor volume is then monitored at the appearance of palpable tumors and followed over time to determine if PC-LECTIN expressing cells grow at a faster rate and whether tumors produced by PC-LECTIN-expressing cells demonstrate characteristics of altered aggressiveness (e.g. enhanced metastasis, vascularization, reduced responsiveness to chemotherapeutic drugs). Additionally, mice may be implanted with $1 \times 10^5$ of the same cells orthotopically to determine if PC-LECTIN has an effect on local growth in the prostate or on the ability of the cells to metastasize, specifically to lungs, lymph nodes, and bone marrow.

The assay is also useful to determine the PC-LECTIN inhibitory effect of candidate therapeutic compositions, such as for example, PC-LECTIN intrabodies, PC-LECTIN anti-sense molecules and ribozymes.

Example 17

Western Analysis of PC-LECTIN Expression in Subcellular Fractions

Sequence analysis of PC-LECTIN revealed the presence of two type-C lectin domains and a transmembrane domain. The cellular location of PC-LECTIN can be assessed further using subcellular fractionation techniques widely used in cellular biology (Storrie B, et al. Methods Enzymol. 1990;182:203–25). Prostate cell lines can be separated into nuclear, cytosolic and membrane fractions. The expression of PC-LECTIN in the different fractions can be tested using western blotting techniques.

Alternatively, to determine the subcellular localization of PC-LECTIN, 293T cells can be transfected with an expression vector encoding HIS-tagged PC-LECTIN (PCDNA 3.1 MYC/HIS, Invitrogen). The transfected cells can be harvested and subjected to a differential subcellular fractionation protocol as previously described (Pemberton, P. A. et al, 1997, J of Histochemistry and Cytochemistry, 45:1697–1706.) This protocol separates the cell into fractions enriched for nuclei, heavy membranes (lysosomes, peroxisomes, and mitochondria), light membranes (plasma membrane and endoplasmic reticulum), and soluble proteins.

Throughout this application, various publications are referenced. The disclosures of these publications are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

What is claimed is:

1. A method to inhibit growth of or inhibit metastases of cancer cells that express PC-LECTIN, which method comprises contacting said cells with an antibody or fragment thereof that specifically binds to PC-LECTIN, wherein said PC-LECTIN has the amino acid sequence shown herein as SEQ. ID. NO: 2.

2. The method of claim 1, wherein said contacting is external to said cells, and the antibody or fragment binds an extracellular region of said PC-LECTIN.

3. The method of claim 1, wherein said antibody or fragment is a monoclonal antibody or fragment thereof.

4. The process of claim 3, wherein said antibody or fragment is humanized.

5. The process of claim 3, wherein said antibody or fragment is human.

6. The process of claim 3, wherein said antibody or fragment is a single chain antibody.

7. The method of claim 1, wherein said antibody or fragment is coupled to a toxin or to a detectable marker.

8. A method to treat a subject for a cancer that expresses PC-LECTIN, which method comprises administering to said subject an antibody or fragment thereof that binds specifically to PC-LECTIN or a nucleic acid molecule comprising nucleotide sequence encoding said antibody or fragment, wherein said PC-LECTIN has the amino acid sequence shown herein as SEQ. ID. NO: 2.

9. The method of claim 8, wherein said antibody or fragment is a monoclonal antibody or fragment thereof.

10. The process of claim 9, wherein said antibody or fragment is humanized.

11. The process of claim 9, wherein said antibody or fragment is human.

12. The process of claim 9, wherein said antibody or fragment is a single chain antibody.

13. The method of claim 8, wherein said antibody or fragment is coupled to a toxin or a detectable marker.

* * * * *